(12) United States Patent
Takakura et al.

(10) Patent No.: US 6,261,822 B1
(45) Date of Patent: Jul. 17, 2001

(54) ULTRATHERMOSTABLE PROTEASE GENES

(75) Inventors: Hikaru Takakura; Mio Morishita; Katsuhiko Yamamoto, all of Otsu; Masanori Mitta, Kyotanabe; Kiyozo Asada, Shiga; Susumu Tsunasawa, Otsu; Ikunoshin Kato, Uji, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 08/894,818

(22) PCT Filed: Nov. 7, 1996

(86) PCT No.: PCT/JP96/03253

§ 371 Date: Aug. 29, 1997

§ 102(e) Date: Aug. 29, 1997

(87) PCT Pub. No.: WO97/21823

PCT Pub. Date: Jun. 19, 1997

(30) Foreign Application Priority Data

Dec. 12, 1995 (JP) .................................................. 7-323285

(51) Int. Cl.[7] .............................. C12P 21/06; C12N 9/52; C12N 1/20
(52) U.S. Cl. ..................... 435/220; 435/69.1; 435/252.3; 536/23.2
(58) Field of Search .................. 435/220, 69.1, 435/320.1, 252.3; 536/23.2

(56) References Cited

U.S. PATENT DOCUMENTS 5,242,817 9/1993 Kelly et al. ........................... 435/220
5,756,339 * 5/1998 Mitta et al. ........................... 435/220

FOREIGN PATENT DOCUMENTS

| 6-197770 | 7/1993 | (JP) . |
| 9534645 | 12/1995 | (WO) . |
| 8807578 | 10/1998 | (WO) . |

OTHER PUBLICATIONS

Ngo et al., "Computational Complexity, Protein Structure Prediction, and the Levinthal Paradox," in The Protein Folding Problem and Tertiary Structure Prediction, Merz, Jr., Ed., Birkhauser Boston, pp. 492–494, 1994.*

Thornton et al., "Protein engineering," Cur. Opinion Biotech., vol. 6, No. 4, pp. 367–369, Aug. 1995.*

Rudinger, p. 6 of Peptide Hormones, Parsons, Ed., University Park Press, Jun. 1976.*

Robinson et al., "A gene from the hyperthermophile *Pyrococcus furiosus* whose deduced product is homologous to member of the prolyl oligopeptidase family of proteases", Elsevier Science B.V., 152:103–106, (1995).

* cited by examiner

Primary Examiner—Rebecca E. Prouty
Assistant Examiner—Manjunath N. Rao
(74) Attorney, Agent, or Firm—Browdy & Neimark

(57) ABSTRACT

There are provided hyperthermostable proteases having an amino acid sequences represented by SEQ ID Nos. 1, 3 and 5 of the Sequence Listing or functional equivalents thereof and hyperthermostable protease genes encoding those hyperthermostable protease. There is also disclosed a process for preparation of a hyperthermostable protease by culturing a transformant containing the gene.

5 Claims, 24 Drawing Sheets

Fig. 2

```
              170                 175                 180
     Asp Gly Ser Gly Val Val Val Ala Val Leu Asp Thr Gly Val
  5'-GAT GGT AGT GGT GTT GTT GTT GCA GTA CTT GAC ACG GGA GTT-3'

PRO-1F   5'-GGW WSD RRT GTT RRH GTH GCD GTD MTY GAC ACB GG-3'
```

Fig. 3

```
              365                 370                 375
     His Gly His Gly Thr His Val Ala Gly Thr Val Ala Gly Tyr
  5'-CAC GGT CAC GGA ACT CAC GTA GCT GGA ACT GTT GCT GGT TAC-3'

PRO-2F   5'-KST CAC GGA ACT CAC GTD GCB GGH ACD GTT GC-3'
PRO-2R       3'-GTG CCT TGA GTG CAH CGV CCK TGH CAA CGM CSA-5'
```

Fig. 4

```
              590                 595
     Ser Gly Thr Ser Met Ala Thr Pro His Val Ser Gly Val Val
  5'-TCT GGA ACT TCG ATG GCT ACT CCA CAT GTC AGC GGT GTC GTT-3'

PRO-4R   3'-CCD TGV AGB TAC CGD WGA GGB GTR CAV YSG CCH C-5'
```

Fig. 11

```
                    10          20          30          40          50
PFUL         MNKKGLTVLF  IAIMLLSVVP  VHFVSAETPP  VSSENSTTSI  LPNQQVVTKE
TCES                                MKRLGAVV    LALVLVGLLA  GTALAAPVKP  VVRNNAVQQK
SUBTILISIN                                                              MRGKKVWISL 60          70          80          90         100
PFUL         VSQAALNAIM  KGQPNMVLII  KTKEGKLEEA  KTELEKLGAE  ILDENRVLNM
TCES         NYGLLTPGLF  KKVQRMNWNQ  EVDTVIMFGS  YGDRDRAVKV  LRLMGAQVKY
SUBTILISIN   LFALALIFTM  AFGSTSSAQA  AGKSNGEKKY  IVGFKQTMST  MSAAKKKDVI 110         120         130         140         150
PFUL         LLVKIKPEKV  KELNYISSLE  KAWLNREVKL  SPPIVEKDVK  TKEPSLEPKM
TCES         SYKIIPAVAV  KIKARDLLLI  AGMIDTGYFG  NTRVSGIKFI  QEDYKVQVDD
SUBTILISIN   SEKGGKVQKQ  FKYVDAASAT  LNEKAVKELK  KDPSVAYVEE  DHVAHAYAQS 160         170         180         190         200
PFUL         YNSTWVINAL  QFIQEF GYDG  SGVVVAVIDT  GVDPNHPFLS  ITPDGRRKII
TCES         ATSVSQIGAD  TVWNSL GYDG  SGVVVAIVDT  GIDANHPDLK  GKVIGWYDAV
SUBTILISIN   VPYGVSQIKA  PALHSQ GYTG  SNVKVAVIDS  GIDSSHPDLK  VAGGASMVPS 210         220         230         240         250
PFUL         EWKDFTDEGF  VDTSFSFSKV  VNGTLIINTT  FQVASGLTLN  ESTGLMEYVV
TCES         NGRSTPYDDQ  ---------   ---------   ---------   ---------
SUBTILISIN   ETNPFQDNN-  ---------   ---------   ---------   ---------

260         270         280         290         300
PFUL         KTVYVSNVTI  GNITSANGIY  HFGLLPERYF  DLNFDGDQED  FYPVLLVNST
TCES         ---------   ---------   ---------   ---------   ---------
SUBTILISIN   ---------   ---------   ---------   ---------   ---------
```

Fig. 11(Cont'd)

```
                    310        320        330        340        350
PFUL         GNGYDIAYVD TDLDYDFTDE VPLGQYNVTY DVAVFSYYYG PLNYVLAEID
TCES         ---------- ---------- ---------- ---------- ----------
SUBTILISIN   ---------- ---------- ---------- ---------- ----------

360        370        380        390        400
PFUL         PNGEYAVFGW DGHGHGTHVA GTVAGYDSNN DAWDWLSMYS GEWEVFSRLY
TCES         ---------- --GHGTHVA  GIVACTGSVN SQ-------- ----------
SUBTILISIN   ---------- SHGTHVA    GTVAA--LNN SI-------- ----------

410        420        430        440        450
PFUL         GWDYTNVTTD TVQGVAPGAQ IMAIRVLRSD GRGSMWDIIE GMTYAATHGA
TCES         ---------- -YIGVAPGAK LVGVKVLGAD GSGSVSTIIA GVDWVQNKD
SUBTILISIN   ---------- GVLGVAPSAS LYAVKVLGAD GSGQYSWIIN GIEWAIANNM 460        470        480        490        500
PFUL         ---DVISMS  LGGNAPYLDG TDPESVAVDE LTEKYGVVFV IAAGNEGPGI
TCES         KYGIRVINLS LGSSQSS-DG TDSLSQAVNN AWDA-GIVVC VAAGNSGPNT
SUBTILISIN   ---DVINMS  LGGP----SG SAALKAAVDK AVAS-GVVVV AAAGNEGTSG 510        520        530        540        550
PFUL         ---IVGSPGV ATKATTVGAA AVPINVGVYV SQALGYPDYY GFYYFPAYTN
TCES         Y---TVGSPAA ASKVITVGAV DSNDN----- ---------- ----------
SUBTILISIN   SSSTVGYPGK YPSVIAVGAV DSSNQ----- ---------- ----------

560        570        580        590        600
PFUL         VRIAFFSSRG PRIDGEIKPN VVAPGYGIYS SLEMWIGGAD F-----MS
TCES         --IASFSSRG PTADCRLKPE VVAPGVDIIA PRASGTSMGT PINDYYTKAS
SUBTILISIN   --RASFSSVG PELD------ VMAPGVSIQS TLPGNKYGA- ------YN
```

Fig. 12

```
            610         620         630         640         650
PFUL        GTSMATPHVS  GVVATLISGA  KAEGIYYNPD  IIKKVLESGA  TWLEGDPYTG
TCES        GTSMATPHVS  GVAALILQAH  PSWTPDKVKT  ----ALIETA  DIVAPKEIAD
SUBTILISIN  GTSMASPHVA  GAAALILSKH  PNWTNTQVRS  ----SLENTT  TKL-GDS---

660         670         680         690         700
PFUL        QKYTELDQGH  GLVNVTKSWE  ILKAINGTTL  PIVDHWADKS  YSDFAEYLGV
TCES        ----IAYGA   GRVNVYKAIK  YDDYAKLTFT  GSVADKGSAT  HTFDVSGATF
SUBTILISIN  ----FYYGK   GLINVQAAAQ  *

710         720         730         740         750
PFUL        DVIRGLYARN  SIPDIVEWHI  KYVGDTEYRT  FEIYATEPWI  KPFVSGSVIL
TCES        VTATLYWDTG  SSDIDLYLYD  PNGNEVDYSY  TAYYGFEKVG  YYNPTAGTWT 760         770         780         790         800
PFUL        ENNTEFVLRV  KYDVEGLEPG  LYVGRIIIDD  PTTPVIEDEI  LNTIVIPEKF
TCES        VKVVSYKGAA  NYQVDVVSDG  SLSQSGGGNP  NPNPNPNPTP  TTDTQTFFGS 810         820         830         840         850
PFUL        TPENNYTLTW  YDINGPEMVT  HHFFTVPEGV  DVLYAMTTYW  DYGLYRPDGM
TCES        VNDYWDTSDT  FTMNVNSGAT  KITGDLTFDT  SYNDLDLYLY  DPNGNLVDRS 860         870         880         890         900
PFUL        FVFPYQLDYL  PAAVSNPMPG  NWELVWTGFN  FAPLYESGFL  VRIYGVEITP
TCES        TSSNSYEHVE  YANPAPGTWT  FLVYAYRTYG  WADYQLKAVV  YYG*

910         920         930         940         950
PFUL        SVWYINRTYL  DTNTEFSIEF  NITNIYAPIN  ATLIPIGLGT  YNASVESVGD
```

Fig. 12(Cont'd)

```
              960        970        980        990        1000
PFUL   GEFFIKGIEV PEGTAELKIR IGNPSVPNSD LDLYLYDSKG NLVALDGNPT
              1010       1020       1030       1040       1050
PFUL   AEEEVVVEYP KPGVYSIVVH GYSVRDENGN PTTTTFDLVV QMTLDNGNIK
              1060       1070       1080       1090       1100
PFUL   LDKDSIILGS NESVVVTANI TIDRDHPTGV YSGIIEIRDN EVYQDTNTSI
              1110       1120       1130       1140       1150
PFUL   AKIPITLVID KADFAVGLTP AEGVLGEARN YTLIVKHALT LEPVPNATVI
              1160       1170       1180       1190       1200
PFUL   IGNYTYLTDE NGTVTFTYAP TKLGSDEITV IVKKENFNTL EKTFQITVSE
              1210       1220       1230       1240       1250
PFUL   PEITEEDINE PKLAMSSPEA NATIVSVEME SEGGVKKTVT VEITINGTAN
              1260       1270       1280       1290       1300
PFUL   ETATIVVPVP KKAENIEVSG DHVISYSIEE GEYAKYVIIT VKFASPVTVT
              1310       1320       1330       1340       1350
PFUL   VTYTIYAGPR VSILTLNFLG YSWYRLYSQK FDELYQKALE LGVDNETLAL
              1360       1370       1380       1390       1400
PFUL   ALSYHEKAKE YYEKALELSE GNIIQYLGDI RLLPPLRQAY INEMKAVKIL
              1410
PFUL   EKAIEELEGE E*
```

—○— Sodium acetate buffer

······▲······ Sodium phosphate buffer

----●---- Sodium borate buffer

----■---- Sodium phosphate-sodium hydroxide buffer

—○— Sodium acetate buffer

·····▲····· Potassium phosphate buffer

----●---- Sodium borate buffer

----■---- Sodium phosphate-sodium hydroxide buffer

ULTRATHERMOSTABLE PROTEASE GENES

TECHNICAL FIELD

The present invention relates to a hyperthermostable protease useful as an industrial enzyme, a gene encoding the same and a method for preparation of the enzyme by the genetic engineering.

BACKGROUND ART

The proteases are the enzymes which cleave peptide bonds in the proteins, and a number of the proteases have been found in animals, plants and microorganisms. They are used not only as reagents for research works and medical supplies, but also in industrial fields such as additives for detergents, food processing and chemical synthesis utilizing the reverse reactions, and it can be said that they are very important enzymes from an industrial viewpoint. For proteases to be used in industrial fields, since very high physical and chemical stabilities are required, in particular, enzymes having high thermostabilities are preferred to use. At present, proteases predominantly used in industrial fields are those produced by bacteria of the genus Bacillus because they have relatively high thermostability.

However, enzymes having further superior properties are desired and activities have been attempted to obtain enzymes from microorganisms which grow at high temperature, for example, thermophiles of the genus Bacillus.

On the other hand, a group of microorganisms, named as hyperthermophiles, are well adapted themselves to high temperature environments and therefor they are expected to be a source supplying various thermostable enzymes. It has been known that one of these hyperthermophiles, *Pyrococcus furiosus*, produces proteases [Appl. Environ. Microbiol., volume 56, page 1992–1998 (1990), FEMS Microbiol. Letters, volume 71, page 17–20 (1990), J. Gen. Microbiol., volume 137, page 1193–1199 (1991)].

A hyperthermophile belonging to the genus Pyrococcus, Pyrococcus sp. Strain KOD1 is reported to produce a thiol protease (cysteine protease) [Appl. Environ. Microbiol., volume 60, page 4559–4566 (1994)]. Bacteria belonging to the genus Thermococcus, Staphylothermus and Thermobacteroides, which are also hyperthermophiles, are known to produce a protease [Appl. Microbiol. Biotechnol., volume 34, page 715–719 (1991)].

OBJECTS OF THE INVENTION

As the proteases produced by these hyperthermophiles have high thermostabilities, they are expected to be applicable to new applications to which any known enzymes has not been utilized. However, the above publication merely teach that thermostable protease activities present in cell-free extract or crude enzyme solution obtained from culture supernatant, and there is no disclosure about properties of isolated and purified enzymes and the like. Only a protease produced by strain KOD1 is obtained as the purified form. However, since a cysteine protease has the defect that it easily loses the activity by oxidation, it is disadvantageous in the industrial use. In addition, since a cultivation of microorganisms at high temperature is required to obtain enzymes from these hyperthermophiles, there is a problem in industrial production of the enzymes.

In order to solve the above problems, an object of the present invention is to provide a protease of the hyperthermophiles which is advantageous in the industrial use, to isolate a gene encoding a protease of the hyperthermophiles, and to provide a method for preparation of a hyperthermostable protease using the gene by the genetic engineering.

DISCLOSURE OF THE INVENTION

In order to obtain a hyperthermostable protease gene, the present inventors originally tried to purify a protease from microbial cells and a culture supernatant of *Pyrococcus furiosus* DSM3638 so as to determine a partial amino acid sequence of the enzyme. However, purification of the protease was very difficult in either cases of using the microbial cells or the culture supernatant, and the present inventors failed to obtain such an enzyme sample having sufficient purity for determination of its partial amino acid sequence.

As a method for cloning a gene for an objective enzyme without any information about a primary structure of the enzyme protein, there is an expression cloning method. For example, a pullulanase gene originating in *Pyrococcus woesei* (WO92/02614) has been obtained according to this method. However, in an expression cloning method, a plasmid vector is generally used and, in such case, it is necessary to use restriction enzymes which can cleave an objective gene into relatively small DNA fragments so that the fragments can be inserted into the plasmid vector without cleavage of any internal portion of the objective gene. Therefore, the expression cloning method is not always applicable to cloning of all kind of enzyme genes. Furthermore, it is necessary to test for an enzyme activity of a large number of clones and this operation is complicated.

The present inventors have attempted to isolate a protease gene by using a cosmid vector which can maintain a larger DNA fragment (30–50 kb) instead of a plasmid vector to prepare a cosmid library of *Pyrococcus furiosus* genome and investigating cosmid clone in the library to find out a clone expressing a protease activity. By using the cosmid vector, the number of transformants to be screened can be reduced in addition to lowering of possibilities of cleavage of a internal portion of the enzyme gene. On the other hand, since the copy number of a cosmid vector in a host cell is not higher than that of a plasmid vector, it may be that an amount of the enzyme expressed is too small to detect it.

In view of high thermostability of the objective enzyme, firstly, the present inventors have cultured respective transformants in a cosmid library, separately, and have combined this step with a step for preparing lysates containing only thermostable proteins from the microbial cells thus obtained, and used these lysates for detecting the enzyme activity. Further, the use of the gelatin-containing SDS-polyacrylamide gel electrophoresis for detecting the protease activity allowed the detection of a trace amount of the enzyme activity.

Thus, the present inventors obtained several cosmid clones expressing the protease activity from the cosmid library of *Pyrococcus furiosus* and successfully isolated a gene encoding a protease from the inserted DNA fragment contained in the clones. In addition, the present inventors confirmed that a protease encoded by the gene has the extremely high thermostability.

By comparing an amino acid sequence of the hyperthermostable protease deduced from the nucleotide sequence of the gene with amino acid sequences of known proteases originating in microorganisms, homology of the amino acid sequence of the front half portion of the hyperthermostable protease with those of a group of alkaline serine proteases, a representative of which is subtilisin, has been shown. In particular, the extremely high homology has been found at each region around the four amino acid residues which are known to be important for the catalytic activity of the enzyme. Thus, since the protease produced by *Pyrococcus furiosus*, which is active at such a high temperature that proteases originating in mesophiles are readily inactivated, has been shown to retain a structure similar to those of enzymes from mesophiles, it has been suggested that similar proteases would also be produced by hyperthermophiles other than *Pyrococcus furiosus*.

Then, the present inventors have noted possibilities that, in the nucleotide sequence of the hyperthermostable protease gene obtained, the nucleotide sequence encoding regions showing high homology with subtilisin and the like can be used as a probe for detecting hyperthermostable protease gene, and have attempted to detect protease genes originating in hyperthermophiles by PCR using synthetic DNAs designed based on the nucleotide sequences as primers so as to clone the gene. As a result, it was found that a fragment of gene having the homology with the above gene existed in a hyperthermophile, *Thermococcus celer* DSM2476. The cloning of the full length of the gene was difficult and this was thought to be due to that the product derived from the gene was harmful to the host.

The present inventors used *Bacillus subtilis* as a host for cloning and found that harbouring of the full length gene was possible and the expressed protease was extracellularly secreted, further revealed that the expressed protease showed the protease activity at 95° C. and had the high thermostability. Upon this, the molecular weight of a protease encoded by the gene was found to be less than half of that of the high-molecular protease derived from the *Pyrococcus furiosus* described above.

In addition, by hybridization using a fragment of the gene as a probe, we found that the second protease gene different from that of the high-molecular protease was present in *Pyrococcus furiosus*. The gene encodes a protease having a similar molecular weight to that of the hyperthermostable protease derived from *Thermococcus celer*, and the gene was isolated and introduced into *Bacillus subtilis* and, thereby, a product expressed from the gene was extracellularly secreted. The expressed protease showed the enzyme activity at 95 ° C. and had the high thermostability. In addition, the amino acid sequence of a mature protease produced by processing of the protease was revealed.

As these two kinds of proteases are extracellularly secreted without any special procedures, it is thought that a signal peptide encoded by the gene itself functions in *Bacillus subtilis*. The amount of expressed both proteases per culture is remarkably higher as compared with the high-molecular protease derived from *Pyrococcus furiosus* which is expressed in *Escherichia coli* or *Bacillus subtilis*. In addition, when the gene is expressed by utilizing a promoter of the subtilisin gene and a signal sequence, the amount of the expressed protease was further increased.

Furthermore, the present inventors prepared a hybrid gene encoding a hybrid protease, i.e. a fusion protein from both proteases, and confirmed that an enzyme expressed by the hybrid gene showed protease activity at high temperature like the above hyperthermostable protease.

SUMMARY OF THE INVENTION

The first aspect of the present invention provides a hyperthermostable protease having the amino acid sequence described in SEQ ID No. 1 of the Sequence Listing or functional equivalents thereof as well as a hyperthermostable protease gene encoding the hyperthermostable proteases, inter alia, a hyperthermostable protease gene having the nucleotide sequence described in SEQ ID No. 2 of the Sequence Listing. Further, a gene which hybridizes with this hyperthermostable protease gene and encodes a hyperthermostable protease is also provided.

In addition, the second aspect of the present invention provides a hyperthermostable protease having the amino acid sequence described in SEQ ID No. 3 of the Sequence Listing or functional equivalents thereof as well as a hyperthermostable protease gene encoding the hyperthermostable proteases, inter alia, a hyperthermostable protease gene having the nucleotide sequence described in SEQ ID No. 4 of the Sequence Listing. Further, a gene which hybridizes with this hyperthermostable protease gene and encodes a hyperthermostable protease is also provided.

In addition, the third aspect of the present invention provides a hyperthermostable protease having the amino acid sequence described in SEQ ID No. 5 of the Sequence Listing or functional equivalents thereof as well as a hyperthermostable protease gene encoding the hyperthermostable proteases, inter alia, a hyperthermostable protease gene having the nucleotide sequence described in SEQ ID No. 6 of the Sequence Listing. Further, a gene which hybridizes with this hyperthermostable protease gene and encodes a hyperthermostable protease is also provided.

Further, the present invention provides a method for preparation of the hyperthermostable protease which comprises cultivating a transformant containing the hyperthermostable protease gene of the present invention, and collecting the hyperthermostable protease from the culture.

As used herein, the term "functional equivalents" means as follows:

It is known that although, among naturally-occurring proteins, a mutation such as deletion, addition, substitution and the like of one or a few (for example, up to 5% of the whole amino acids) amino acid(s) can occur in the amino acid sequence thereof due to the modification reaction and the like of the produced proteins in the living body or during purification besides the polymorphism or mutation of the genes encoding them, there are proteins, in spite of the mutation described above, showing the substantially equivalent physiological or biological activity to that of the proteins having no mutation. When the proteins have the slight difference in the structures and, nevertheless, the great difference in the functions thereof is not recognized, they are called functional equivalents. This is true when the above mutations are artificially introduced into the amino acid sequence of the proteins and, in this case, further a more variety of mutants can be made. For example, a polypeptide where a certain cysteine residue is replaced with serine residue in the amino acid sequence of human interleukin-2 (IL-2) shows the interleukin-2 activity [Science, volume 224, page 1431 (1984)].

A product of the gene which is transcribed and translated from the hyperthermostable protease gene of the present invention is an enzyme precursor (preproenzyme) containing two regions, one of them is a signal peptide necessary for extracellular secretion and the other is a propeptide which is removed upon expression of the activity. When a transformant to which the above gene has been transferred can cleave this signal peptide, an enzyme precursor (proenzyme) from which the signal peptide has been removed is extracellularly secreted. Further, an active form enzyme from which the propeptide has been removed is produced by the self-digestion reaction between proenzymes. All of the preproenzyme, proenzyme and active form enzyme thus obtained from the gene of the present invention are proteins which finally have the equivalent function and fall within the scope of "functional equivalents".

As apparent to those skilled in the art, an appropriate signal peptide may be selected depending upon a host used for the expression of a gene of interest. The signal peptide may be removed when the extracellular secretion is not desired. Therefore, among hyperthermostable protease genes disclosed herein, the genes from which a portion encoding a signal peptide has been removed, and the genes where the portion is replaced with other nucleotide sequence are also within the scope of the present invention in the context that they encode the proteases showing the essentially equivalent activity.

As used herein, a gene which "hybridizes to a hyperthermostable protease gene" refers to a gene which hybridizes with the hyperthermostable protease gene under the stringent conditions, that is, those where incubation is carried out at 50 ° C. for 12 to 20 hours in 6×SSC (1×SSC represents 0.15M NaCl, 0.015M sodium citrate, pH7.0) containing 0.5% SDS, 0.1% bovine serum albumin (BSA), 0.1% polyvinylpyrrolidone, 0.1% Ficoll 400 and 0.01% denatured salmon sperm DNA.

BRIEF DESCRIPTION OF DRAWINGS

FIG. 2 is a figure showing a design of the oligonucleotide PRO-1F.

FIG. 3 is a figure showing a design of the oligonucleotide PRO-2F and PRO-2R.

FIG. 4 is s figure showing a design of the oligonucleotide PRO-4R.

FIG. 11 is s figure comparing the amino acid sequences of the various proteases.

FIG. 12 is a continuation of FIG. 11.

PREFERRED EMBODIMENTS OF THE INVENTION

Figure 1:
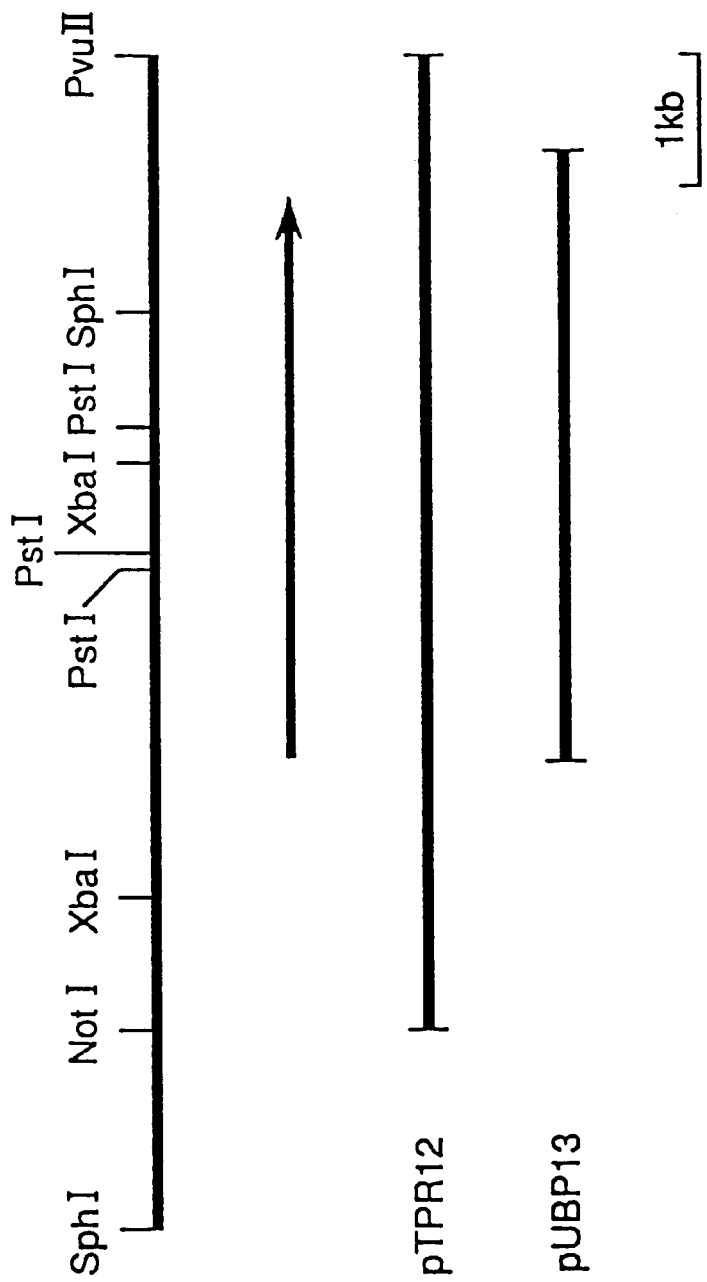
FIG. 1 is a figure showing a restriction map of a DNA fragment derived from *Pyrococcus furiosus* contained in the plasmid pTPR12 and the plasmid pUBP13.

The hyperthermostable protease gene of the present invention can be obtained by screening the gene library of hyperthermophiles. As the hyperthermophile, bacteria belonging to the genus Pyrococcus can be used and the gene of interest can be obtained by screening a cosmid library of *Pyrococcus furiosus* genome.

For example, *Pyrococcus furiosus* DSM3638 can be used as *Pyrococcus furiosus*, and the strain is available from Deutsche Sammlung von Mikroorganismen und Zellkulturen GmbH.

One example of the cosmid libraries of *Pyrococcus furiosus* genome can be obtained by ligating DNA fragments which are obtained by partial digestion of the genomic DNA of *Pyrococcus furiosus* DSM3638 with a restriction enzyme Sau3Al (manufactured by Takara Shuzo Co., Ltd.), with the triple helix cosmid vector (manufactured by Stratagene), and packaging the ligated product into a lambda phage particle according to the in vitro packaging method. Then, the library is transduced into the suitable *Escherichia coli*, for example, *Escherichia coli* DH5αMCR (manufactured by BRL) to obtain the transformants, followed by cultivation them, collecting the microbial cells, subjecting them to heat treatment (for example, 100° C. for 10 minutes), sonicating and subjecting them to heat treatment (for example, 100° C. for 10 minutes) again. The presence or absence of the protease activity in the resulting lysate can be screened by utilizing the gelatin—containing SDS-polyacrylamide gel electrophoresis.

In this manner, a cosmid clone containing a hyperthermostable protease gene expressing a protease which is resistant to the above heat treatment can be obtained.

Further, the cosmid DNA prepared from the cosmid clone thus obtained can be digested into fragments with a suitable restriction enzyme to obtain a recombinant plasmid with each fragment incorporated. Then, a suitable microorganism is transformed with the plasmid, and the protease activity expressed by the resulting transformant can be examined to obtain a recombinant plasmid containing a hyperthermostable protease gene of interest.

That is, the cosmid prepared from one of the above cosmid clones is digested with NotI and PvuII (both manufactured by Takara Shuzo Co., Ltd.) to give an about 7.5 kb DNA fragment which can be isolated and inserted between the NotI site and the SmaI site of the plasmid vector pUC19 (manufactured by Takara Shuzo Co., Ltd.) into which the NotI linker (manufactured by Takara Shuzo Co., Ltd.) has been introduced. The plasmid was designated the plasmid pTPR12 and *Escherichia coli* JM109 transformed with the plasmid was designated *Escherichia coli* JM109/pTPR12 and has been deposited at National Institute of Bioscience and Human-Technology at 1-1-3. Higashi, Tsukuba-shi, Ibaraki-ken, Japan since May 24, 1994 (original deposit date) as the accession number FERM BP-5103 under Budapest Treaty.

The lysate of the *Escherichia coli* JM109/pTPR12 shows the similar protease activity to that of the above cosmid clone on the gelatin-containing SDS-polyacrylamide gel.

The nucleotide sequence of the DNA fragment, derived from *Pyrococcus furiosus*, which was inserted into the plasmid pTPR12 can be determined by a conventional method, for example, the dideoxy method. The nucleotide sequence of the 4.8 kb portion flanked by two DraI sites within the DNA fragment inserted into the plasmid pTPR12 is shown in SEQ ID No. 7 of the Sequence Listing. The amino acid sequence of a gene product deduced from the nucleotide sequence is shown in SEQ ID No. 8 of the Sequence Listing. Thus, a hyperthermostable protease, the nucleotide sequence and the amino acid sequence of which were revealed, derived from *Pyrococcus furiosus* was designated the protease PFUL. As shown in SEQ ID No. 8 of the Sequence Listing, the protease PFUL is a protease consisting of 1398 residues and having a high-molecular weight of more than 150 thousands.

The protease PFUL gene can be expressed using *Bacillus subtilis* as a host. As *Bacillus subtilis*, *Bacillus subtilis* DB104 can be used and the strain is the known one described in Gene, volume 83, page 215–233 (1989). As a cloning vector, the plasmid pUB18-P43 can be used and the plasmid was gifted from Dr. Sui-Lam Wong at Calgary University. The plasmid contains the kanamycin resistant gene as a selectable marker.

There is the plasmid pUBP13 where an about 4.8 kb DNA fragment obtained by digestion of the plasmid pTPR13 with DraI has been inserted into the SmaI site of the plasmid vector pUB18-P43. In the plasmid, the protease PFUL gene is located downstream of the P43 promoter [J. Biol. Chem., volume 259, page 8619–8625 (1984)] which functions in *Bacillus subtilis*. *Bacillus subtilis* DB104 transformed with the plasmid was designated *Bacillus subtilis* DB104/pUBP13. The lysate of the transformant shows the similar protease activity to that of the *Escherichia coli* JM109/pTPR12.

However, only a trace amount of the protease activity is detected in a culture supernatant of the transformant. This is thought to be due to that a molecular weight of the protease PFUL is extremely high and it is not translated effectively in *Bacillus subtilis*, and that a signal sequence encoded by the protease PFUL gene dose not function well in *Bacillus subtilis*. There is a possibility that the protease PFUL is a membrane-bound type protease, and the peptide chain on the C-terminal side of the protease PFUL may be a region for binding to the cell membrane.

FIG. 1 shows a restriction map around the protease PFUL gene on the *Pyrococcus furiosus* chromosome, as well as a DNA fragment inserted into the plasmid pTPR12 and that inserted into the plasmid pUBP13. In addition, an arrow in FIG. 1 shows the open reading frame encoding the protease PFUL.

By comparing the amino acid sequence of the protease PFUL represented by SEQ ID. No. 8 of the Sequence Listing with that of a protease derived from the known microorganism, it is seen that there is the homology between the amino acid sequence of the front half portion of the protease PFUL and that of a group of alkaline serine proteases, a representative of which is subtilisin [Protein Engineering, volume 4, page 719–737 (1991)], and that there is the extremely high homology around four amino acid residues which are considered to be important for catalytic activity of the proteases.

As it was revealed that regions commonly present in the proteases derived from a mesophile are conserved in the amino acid sequence of the protease PFUL produced by the hyperthermophile *Pyrococcus furiosus*, it is expected that these regions are present in the same kind of proteases produced by the hyperthermophiles other than *Pyrococcus furiosus*.

That is, a DNA having the suitable length can be prepared based on the sequence of a portion encoding the amino acid sequence of a region having the high homology with that of subtilisin and the like, and the DNA can be used as a probe for hybridization or as a primer for gene amplification such as PCR and the like to screen a hyperthermostable protease gene similar to the present enzyme present in various hyperthermophiles.

In the above method, a DNA fragment containing only a portion of the gene of interest is obtained in some cases. Upon this, the nucleotide sequence of the resulting DNA fragment is investigated and confirmed that it is a portion of the gene of interest and, thereafter, hybridization can be carried out using the DNA fragment or a part thereof as a probe or PCR can be carried out using a primer synthesized based on the nucleotide sequence of the DNA fragment to obtain the whole gene of interest.

The above hybridization can be carried out under the following conditions. That is, a membrane to which a DNA is fixed is incubated with a probe suitably labeled at 50° C. for 12 to 20 hours in 6×SSC (1×SSC represents 0.15M NaCl, 0.015M sodium citrate, pH 7.0) containing 0.5% SDS, 0.1% bovine serum albumin (BSA), 0.1% polyvinylpyrrolidone, 0.1% Ficoll 400 and 0.01% denatured salmon sperm DNA. After the completion of incubation, the membrane is washed, beginning with washing at 37° C. in 2×SSC containing 0.5% SDS, varying the SSC concentration in a range of to 0.1× and a temperature in a range of to 50 ° C., until a signal from a probe hybridized to the fixed DNA can be discriminated from the background.

In addition, it is apparent to those skilled in the art that a probe and a primer can be made based on the thus obtained new hyperthermostable gene to obtain another hyperthermostable protease gene according to the similar method.

FIGS. 2, 3 and 4 show the relationship among the amino acid sequences of regions in the amino acid sequence of the protease PFUL which have high homology with those of subtilisin and the like, the nucleotide sequence of the protease PFUL gene encoding the region, and the nucleotide sequences of the oligonucleotides PRO-1F , PRO-2F, PRO-2R and PRO-4R which were synthesized based thereon. Further, SEQ ID Nos. 9, 10, 11 and 12 of the Sequence Listing show the nucleotide sequences of the oligonucleotides PRO-1F , PRO-2F, PRO-2F and PRO-4R. That is, SEQ ID Nos. 9–12 are the nucleotide sequences of one example of the oligonucleotides used for screening the hyperthermostable protease gene of the present invention.

By using a combination of the oligonucleotides as primer, a protease gene can be detected by PCR using a chromosomal DNA of the various hyperthermophiles as a template.

As the hyperthermophiles, the bacteria belonging to the genus Pyrococcus, genus Thermococcus, genus Staphylothermus, genus Thermobacteroides and the like can be used. As the bacteria belonging to genus Thermococcus, for example, *Thermococcus celer* DSM2476 can be used and the strain can be obtained from Deutsche Sammlung von Mikroorganismen und Zellkulturen GmbH. When PCR is carried out using a chromosomal DNA of *Thermococcus celer* DSM2476 as a template and using a combination of the oligonucleotides PRO-1F and PRO-2R or a combination of the oligonucleotides PRO-2F and PRO-4R as a primer, the specific amplification of a DNA fragment is observed and the presence of a protease gene can be identified. In addition, the amino acid sequence encoded by the DNA fragment can be estimated by inserting the DNA fragments into a suitable plasmid vector to make a recombinant plasmid and, thereafter, determining the nucleotide sequence of the inserted DNA fragment by the dideoxy method.

A DNA fragments of about 150 bp amplified using the oligonucleotides PRO-1F and PRO-2R and DNA fragment of about 550 bp DNA amplified using the oligonucleotides PRO-2F and PRO-4R are inserted into the HincII site of the plasmid vector pUC18 (manufactured by Takara Shuzo Co., Ltd.). The recombinant plasmids are designated the plasmid p1F-2R(2) and the plasmid p2F-4R, respectively. SEQ ID No. 13 of the Sequence Listing shows the nucleotide sequence of the inserted DNA fragment in the plasmid p1F-2R(2) and the amino acid sequence deduced therefrom and SEQ ID No. 14 of the Sequence Listing shows the nucleotide sequence of the inserted DNA fragment in the plasmid p2F-4R and the amino acid sequence deduced therefrom. In the SEQ ID No. 13 of the Sequence Listing, the nucleotide sequence from the 1st to the 21st nucleotides and that from the 113rd to he 145th nucleotides and, In the SEQ ID No. 14 of the Sequence Listing, the nucleotide sequence from the 1st to the 32nd nucleotides and that from the 532nd to the 564th nucleoti des are the nucleotide sequence derived from the oligonucleotides used in PCR as primers (each corresponding to the oligonucleotides PRO-1F , PRO-2R, PRO-2F and PRO-4R, respectively). The amino acid sequences having the homology with that of the protease PFUL and the alkaline serine proteases derived from the various microorganisms are present in the amino acid sequences represented by SEQ ID Nos. 13 and 14 of the Sequence Listing, indicating that the above PCR-amplified DNA fragments were amplified with the protease gene as a template.

Figure 5:
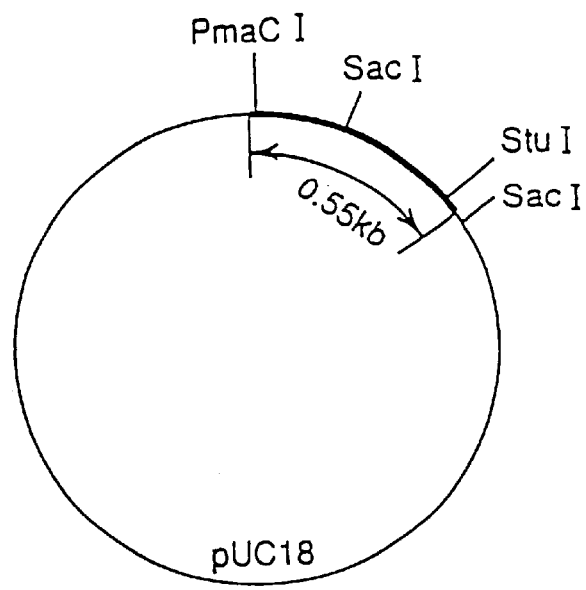
FIG. 5 is a restriction map of the plasmid p2F-4R.

A restriction map of the plasmid p2F-4R is shown in FIG. 5. In FIG. 5, a thick solid line indicates the DNA fragment inserted into the plasmid vector pUC18.

Then, a hyperthermostable protease gene, for example, a gene of the hyperthermostable protease produced by *Thermococcus celer* can be obtained by screening the gene library of hyperthermostable bacteria using above oligonucleotides or the amplified DNA fragments obtained by the above PCR as a probe.

One example of the gene libraries of *Thermococcus celer*, there is a library prepared by partially digesting a chromosomal DNA of *Thermococcus celer* DSM2476 with the restriction enzyme Sau3AI to obtain a DNA fragment, ligating the fragment with lambda GEM-11 vector (manufactured by Promega) and packaged it into the lambda phage particle using the in vitro packaging method. Then, the library can be transduced into suitable *Escherichia coli*, for example, *Escherichia coli* LE392 (manufactured by Promega) to allow to form the plaques on a plate, and plaque hybridization can be carried out using an amplified DNA fragment obtained by the above PCR as a probe to obtain phage clones containing a gene of interest.

Further, a phage DNA prepared from the phage clones thus obtained can be digested with a suitable restriction enzyme, and southern hybridization can be carried out using the above probe to detect a DNA fragment containing a protease gene.

Figure 6:
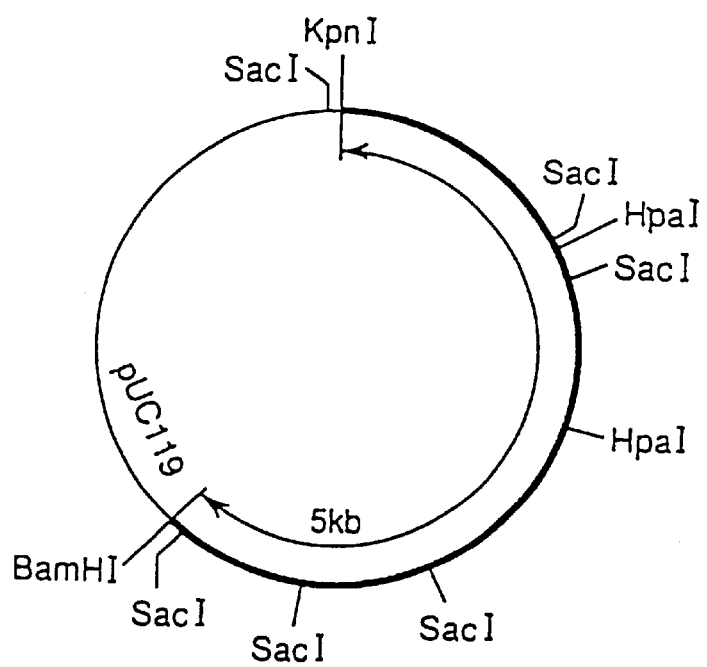
FIG. 6 is a restriction map of the plasmid pTC3.

When the phage DNA prepared from the phage clones obtained by the plaque hybridization is digested with KpnI and BamHI (both manufactured by Takara Shuzo Co., Ltd.), an about 5 kb DNA fragment is hybridized to the probe, and the about 5 kb DNA fragment can be isolated and inserted between the KpnI site and the BamHI site of the plasmid vector pUC119 (manufactured by Takara Shuzo Co., Ltd.) to obtain a recombinant plasmid. The plasmid was designated the plasmid pTC3 and *Escherichia coli* JM109 transformed with the plasmid was designated *Escherichia coli* JM109/pTC3. A restriction map of the plasmid pTC3 is shown in FIG. 6. In FIG. 6, a thick solid line designates the DNA fragment inserted into the plasmid vector pUC119.

Figure 7:
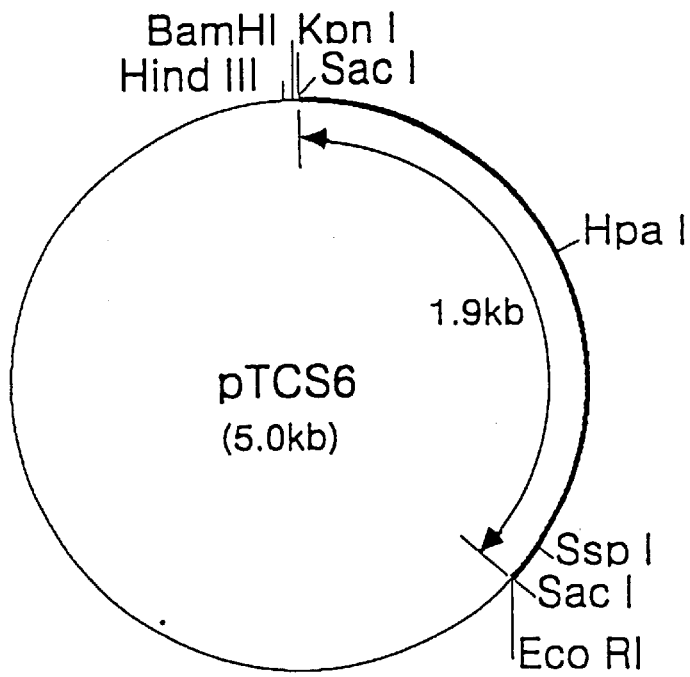
FIG. 7 is a restriction map of the plasmid pTCS6.

A DNA fragment which does not contain the protease gene within the DNA fragment inserted into the plasmid pTC3 can be removed according to the following procedures. That is, after the plasmid pTC3 is digested with SacI (manufactured by Takara Shuzo Co., Ltd.), southern hybridization is carried out according to the similar procedures described above and it is found that an about 1.9 kb DNA fragment hybridizes to the probe. Then, the about 1.9 kb DNA fragment can be isolated and inserted into the SacI site of the plasmid vector pUC118 (manufactured by Takara Shuzo Co., Ltd.) to make a recombinant vector. The plasmid was designated the plasmid pTCS6 and *Escherichia coli* JM109 transformed with the plasmid was designated *Escherichia coli* JM109/pTCS6. A restriction map of the plasmid pTCS6 is shown in FIG. 7. In FIG. 7, a thick solid line designates the DNA fragment inserted into the plasmid vector pUC118. By determining the nucleotide sequence of the DNA fragment inserted into the plasmid pTCS6 by the dideoxy method, it can be confirmed that a protease gene is present in the DNA fragment. SEQ ID No. 15 of the Sequence Listing shows the nucleotide sequence of the fragment. By comparing the nucleotide sequence with that of the DNA fragment inserted into the plasmid p1F-2R (2) or that of the plasmid p2F-4R represented by SEQ ID No. 13 or 14 of the Sequence Listing, it is seen that the DNA fragment inserted into the plasmid pTCS6 contains the DNA fragment which is also shared by the plasmid p2F-4R but lacks a 5' region of the protease gene.

Like this, the hyperthermostable protease gene, derived from *Thermococcus celer*, contained in the plasmid pTCS6 lacks a portion thereof. However, as apparent to those skilled in the art, a DNA fragment covering the full length hyperthermostable protease gene can be obtained by (1) screening the gene library once more, (2) conducting southern hybridization using a chromosomal DNA, or (3) obtaining a DNA fragment of a 5' upstream region by PCR using a cassette and a cassette primer (Takara Shuzo Co., Ltd., Genetic Engineering Products Guidance, 1994–1995 edition, page 250–251).

Figure 8:
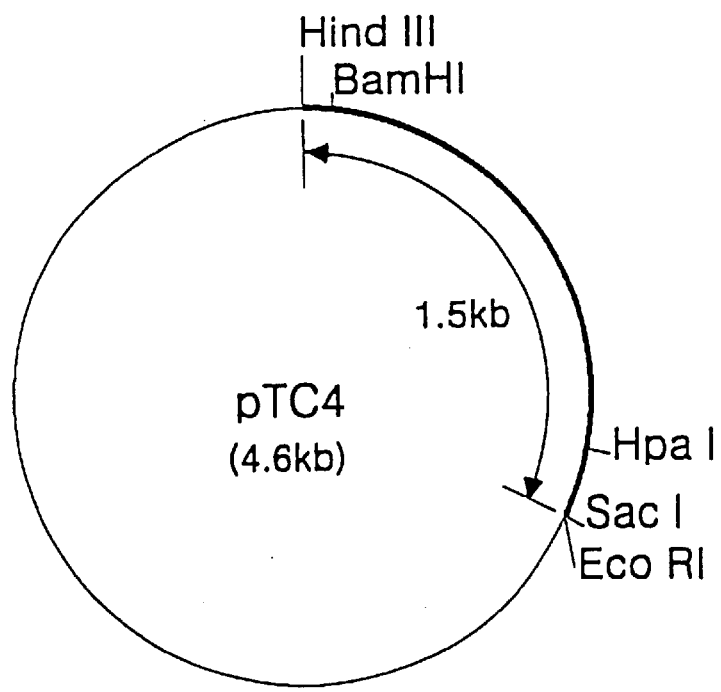
FIG. 8 is a restriction map of the plasmid pTC4.

The present inventors selected the method (3). That is, a chromosomal DNA of the *Thermococcus celer* is completely digested with a few restriction enzymes, followed by ligation with a cassette (manufactured by Takara Shuzo Co., Ltd.) which corresponds to the restriction enzyme used. PCR is carried out using this ligation product as a template and the primer TCE6R (SEQ ID No. 16 of the Sequence Listing shows the nucleotide sequence of the primer TCE6R) and the cassette primer C1 (manufactured by Takara Shuzo Co., Ltd.) as primers. When the above procedures are carried out using the restriction enzyme HindIII (manufactured by Takara Shuzo Co., Ltd.), an about 1.8 kb DNA fragment is amplified, and a DNA fragment of about 1.5 kb which is obtained by digesting above amplified fragment with HindIII and SacI can be inserted into between the HindIII site and the SacI site of the plasmid vector pUC119 to obtain a recombinant plasmid. The plasmid was designated the plasmid pTC4 and *Escherichia coli* JM109 transformed with the plasmid was designated *Escherichia coli* JM109/pTC4. A restriction map of the plasmid pTC4 is shown in FIG. 8. In FIG. 8, a thick solid line designates the DNA fragment inserted into the plasmid vector pUC119.

By determining the nucleotide sequence of the DNA fragment inserted into the plasmid pTC4 by the dideoxy method, it can be confirmed that a protease gene is present in the DNA fragment. SEQ ID No. 17 of the Sequence Listing shows the nucleotide sequence of the fragment. By comparing the amino acid sequence deduced from the nucleotide sequence with those of the various proteases, it is found that the DNA fragment inserted into the plasmid pTC4 covers the 5' region of the hyperthermostable protease gene which the plasmid pTCS6 lacks. By combining the nucleotide sequence with that of the DNA fragment inserted into the plasmid pTCS6 represented by SEQ ID No. 15 of the Sequence Listing, the nucleotide sequence of the full length hyperthermostable gene derived from *Thermococcus celer* can be identified. The nucleotide sequence of the open reading frame present in the obtained nucleotide sequence is shown in SEQ ID No. 2 of the Sequence Listing and the amino acid sequence deduced from the nucleotide sequence is shown in SEQ ID No. 1, respectively. Thus, the hyperthermostable protease derived from *Thermococcus celer*, with the nucleotide sequence encoding it and the amino acid sequence thereof revealed was designated the protease TCES. The full length of the protease TCES gene can be reconstituted by combining the inserted DNA fragment of the plasmid pTC4 and that of the plasmid pTCS6.

It is contemplated that the protease activity expressed by the gene can be confirmed by reconstituting the full length protease TCES gene from two DNA fragments contained in pTC4 and pTCS6, and inserting this downstream of the lac promoter of a plasmid to give an expression plasmid which is introduced into *Escherichia coli*. However, this method affords no transformants into which the expression vector of interest has been introduced, and it is predicted that the production of a product expressed from the gene is harmful or lethal to *Escherichia coli*. It is contemplated that, in such as case, for example, a protease is extracellularly secreted using *Bacillus subtilis* as a host to confirm the activity.

As a host for expressing the protease TCES gene in *Bacillus subtilis*, the *Bacillus subtilis* DB104 can be used and, as a cloning vector, the plasmid pUB18-P43 can be used.

However, since the host-vector system for *Escherichia coli* has the advantages that it contains various kind of vectors and transformation can be carried out simply and highly effectively, as many as possible procedures for constructing an expression vector are desirably, if possible, carried out by using *Escherichia coli*. That is, in *Escherichia coli*, an optional nucleotide sequence containing a termination codon is inserted between two protease gene fragments derived from the plasmid pTC4 and the plasmid pTCS6 so that the full length protease TCES gene is not reconstituted, thus, making expression of the gene product impossible and, therefore, the construction of a plasmid can be carried out. Then, this inserted sequence can be removed at the final stage to make the expression plasmid pSTC3 of interest shown in FIG. 10.

Figure 9:
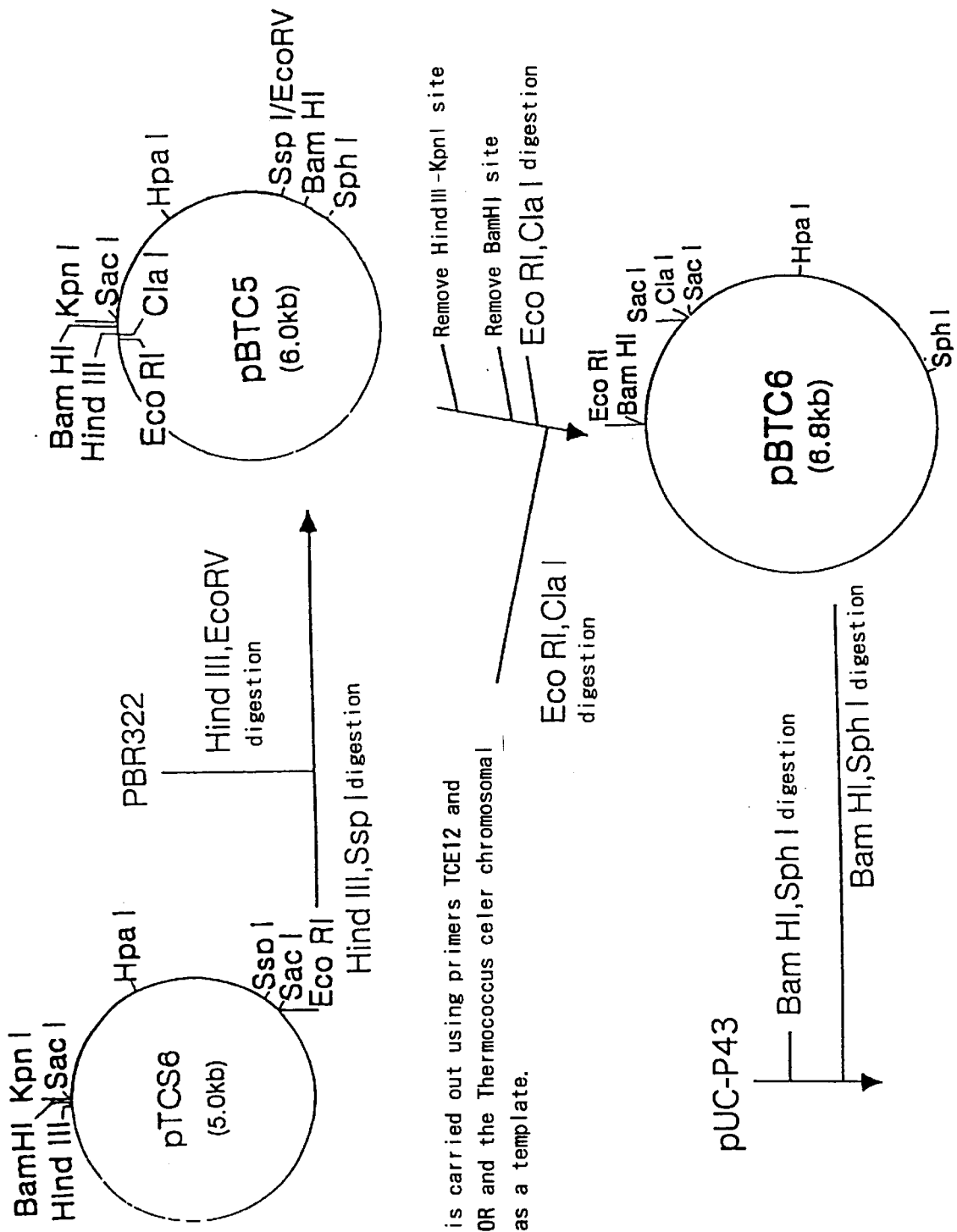
FIG. 9 is a figure showing the procedures for constructing the plasmid pSTC3.
Figure 9:
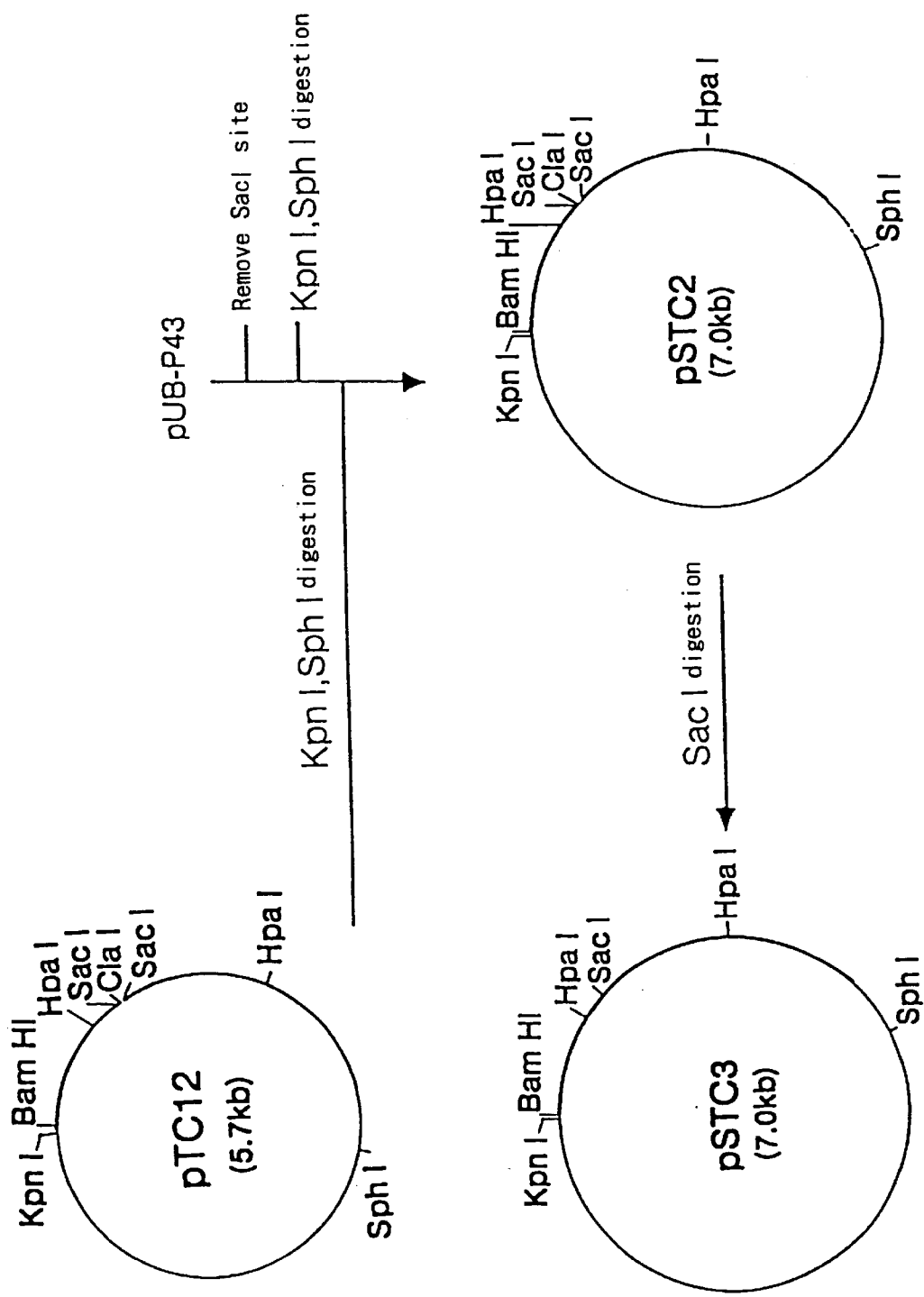

The procedures for constructing the plasmid pSTC3 shown in FIG. 9 are explained below.

First, the about 1.8 kb HindIII-SspI fragment inserted into the plasmid pTCS6 is inserted between the HindIII site and the EcoRV site of the plasmid vector pBR322 (manufactured by Takara Shuzo Co., Ltd.) to make the recombinant plasmid pBTC5 and, from this plasmid, the DNA fragment between the HindIII site and the KpnI site derived from a multicloning site of the plasmid vector pUC118 and the BamHI site present on the plasmid vector pBR322 are removed to make the plasmid pBTC5HKB.

Then, based on the nucleotide sequence of the protease TCES gene, the primer TCE12 which can introduce the EcoRI site and the BamHI site in front of an initiation codon of the protease TCES, and the primer TCE20R which can introduce the ClaI site and a termination codon on the 3' side of only one SacI site present in the nucleotide sequence are synthesized. SEQ ID Nos. 18 and 19 of the Sequence Listing show the nucleotide sequences of the primer TCE12 and the primer TCE20R, respectively.

An about 0.9 kb DNA fragment which has been amplified by PCR using a chromosomal DNA of *Thermococcus celer* as a template and using these two primers is digested with EcoRI and ClaI (manufactured by Takara Shuzo Co., Ltd.), and inserted into between the EcoRI site and the ClaI site of the plasmid pBTC5HKB to obtain the plasmid pBTC6, which has a mutant gene where the nucleotide sequence of 69 bp long including a termination codon is inserted into the SacI site of the protease TCES gene.

A ribosome binding site derived from the *Bacillus subtilis* P43 promoter [J. Biol. Chem., volume 259, page 8619–8625 (1984)] is introduced between the KpnI site and the BamHI site of the plasmid vector pUC18 to make the plasmid pUC-P43. The nucleotide sequences of the synthetic oligonucleotides BS1 and BS2 are shown in SEQ ID Nos. 20 and 21 of the Sequence Listing, respectively. Then, the plasmid pBTC6 is digested with BamHI and SphI (both manufactured by Takara Shuzo Co., Ltd.) to obtain an about 3 kb DNA fragment containing a mutant gene of the protease TCES, which is inserted between the BamHI site and the SphI site of the plasmid pUC-P43 to construct the plasmid pTC12.

All the above procedures for constructing a plasmid can be carried out using *Escherichia coli* as a host.

The SacI site present in the plasmid vector pUC18-P43 used for cloning into *Bacillus subtilis* is previously removed, and an about 3 kb KpnI-SphI DNA fragment obtained from the pTC12 can be inserted into between the KpnI site and the SphI site to make the plasmid pSTC2 using *Bacillus subtilis* DB104 as a host. The plasmid contains a mutant gene of the protease TCES having the P43 promoter and a ribosome binding site sequence on its 5' side. After the plasmid pSTC2 is digested with SacI, and intramolecular ligation is carried out to obtain a recombinant plasmid, from which the inserted sequence contained in the SacI site of the above mutant gene has been removed. The recombinant plasmid was designated the plasmid pSTC3, and *Bacillus subtilis* DB104 transformed with the plasmid was designated *Bacillus subtilis* DB104/pSTC3 and has been deposited at National Institute of Bioscience and Human-Technology at 1-1-3, Higashi, Tsukuba-shi, Ibaraki-ken, Japan under accession number FERM BP-5635 since Dec. 1, 1995 (original deposit date)

according to Budapest Treaty. The transformant is cultured, and a culture supernatant and an extract from the cells were investigated for the protease activity. As a result, the thermostable protease activity is found in both samples.

Figure 10:
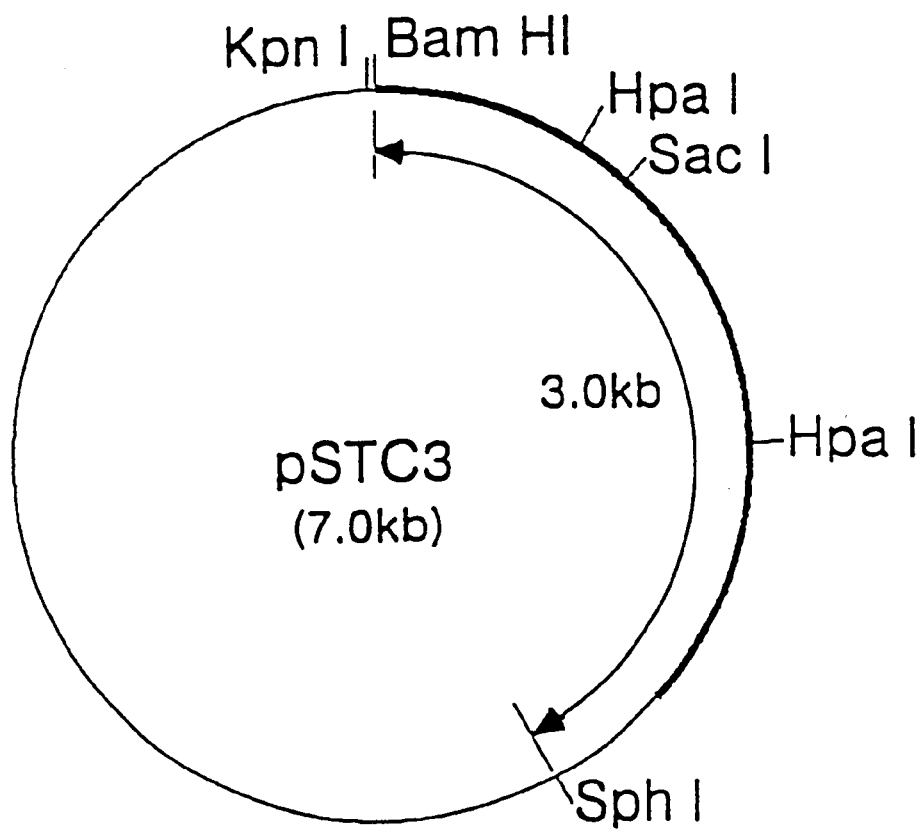
FIG. 10 is a restriction map of the plasmid pSTC3.

FIG. 10 shows a restriction map of the plasmid pSTC3. In FIG. 10, a thick solid line designates the DNA fragment inserted into the plasmid vector pUB18-P43.

When the amino acid sequences of the protease PFUL, the protease TCES and subtilisin are aligned so that the regions having the homology coincide with each other as shown in FIGS. 11 and 12, it is seen that the protease PFUL has the regions which is not homologous with the sequence of the protease TCES and that of subtilisin at the C-terminal side thereof as well as between the regions having the homology. From this, it is contemplated that, besides the protease PFUL, a protease having a smaller molecular weight than that of the protease PFUL, such as the protease TCES or subtilisin may be present in *Pyrococcus furiosus*. In order to search a gene encoding such a protease, southern hybridization can be carried out using a chromosomal DNA prepared from *Pyrococcus furiosus* as a target, and using a DNA fragment containing the nucleotide sequence within the protease TCES gene, which encoding the amino acid sequence which is well conserved in three proteases, for example, the about 150 bp DNA fragment inserted into the plasmid p1F-2R (2), as a probe. Although, since the DNA fragment used for a probe has also the homology with the protease PFUL gene, the gene fragment is detected as a signal depending upon the hybridization conditions, the position of the signal derived from the gene can be previously estimated on each restriction enzyme used for cutting a chromosomal DNA, from the informations on the nucleotide sequence of the protease PFUL gene and the restriction map. When some enzymes are used, in addition to the position predicted on the protease PFUL gene, an another signal is detected as almost the same level, suggesting the possibility that at least one protease is present in *Pyrococcus furiosus* in addition to the protease PFUL.

For isolating a gene corresponding to the above new signal, a portion of the gene is first cloned so as to prevent the failure of isolation of the gene, as in a case of the protease TCES, resulted from the expression of the gene product which is harmful or lethal to *Escherichia coli*. For example, when a chromosomal DNA of *Pyrococcus furiosus* is digested with the restriction enzymes SacI and SpeI (both manufactured by Takara Shuzo Co., Ltd.) and the digestion products are used to conduct southern hybridization as described above using a fragment of the protease TCES gene as a probe, it was revealed that a new signal corresponding to about 0.6 kb, derived from the new gene, was observed replacing with a signal corresponding to about 3 kb which was observed in a case of digestion with only SacI. This about 0.6 kb SpeI-SacI fragment encodes the amino acid sequence of at maximum around 200 residues and it can not be contemplated to express a protease having the activity. A *Pyrococcus furiosus* chromosomal DNA digested with SacI and SpeI is subjected to agarose gel electrophoresis to recover a DNA fragment corresponding to about 0.6 kb from the gel.

Then, the fragment is inserted between the SpeI site and the SacI site of the plasmid vector pBluescript SK(−) (manufactured by Stratagene) and the resulting recombinant plasmid is used to transform *Escherichia coli* JM109. From this transformant, a clone with a fragment of interest incorporated can be obtained by colony hybridization using the same probe as that used for the above southern hybridization. Whether a plasmid contained in the resulting clone has the sequence encoding a protease or not can be confirmed by conducting PCR using the primers 1FP1, 1FP2, 2RP1 and 2RP2 (the nucleotide sequences of the primers 1FP1, 1FP2, 2RP1 and 2RP2 are shown in SEQ ID Nos. 22, 23, 24, and 25 of the Sequence Listing) made based on the amino acid sequence common to the above various proteases, or by determining the nucleotide sequence of a DNA fragment inserted into the plasmid prepared from the clone. The plasmid in which the existence of a protease gene is confirmed in this manner was designated the plasmid pSS3. The nucleotide sequence of a DNA fragment inserted in the plasmid, and the amino acid sequence deduced therefrom are shown in SEQ ID No. 26 of the Sequence Listing.

The amino acid sequence deduced from the nucleotide sequence of the DNA fragment inserted into the plasmid pSS3 is shown to have the homology with the sequences of subtilisin, the protease PFUL, the protease TCES and the like. A product of a protease gene different from the protease PFUL, a portion of which was obtained newly from *Pyrococcus furiosus*, was designated the protease PFUS. A region encoding a N-terminal side part of the protease, that is, a region 5' of the SpeI site, and a region encoding a C-terminal side part, that is, a gene fragment 3' of the above SacI site can be obtained by the inverse PCR method. If the restriction enzyme sites in the protease PFUS gene and the vicinity thereof in a chromosome are revealed in advance, the inverse PCR can be carried out using an appropriate restriction enzyme. The restriction enzyme sites can be revealed by cutting a chromosomal DNA of *Pyrococcus furiosus* with various restriction enzymes, and conducting southern hybridization using a DNA fragment inserted into the plasmid pSS3 as a probe. Consequently, it is shown that the SacI site is located on about 3 kb distant 5' side of the SpeI site and the XbaI site is located on about 5 kb distant 3' side of the SacI site.

A primer used for the inverse PCR can be design to anneal at around an end of the SpeI-SacI fragment contained in the plasmid pSS3. The primers designed to anneal at around the SacI site are designated NPF-1 and NPF-2 and a primer designed to anneal at around the SpeI site is designated NPR-3. The nucleotide sequences thereof are shown in SEQ ID Nos. 27, 28 and 29 of the Sequence Listing, respectively.

Figure 13:
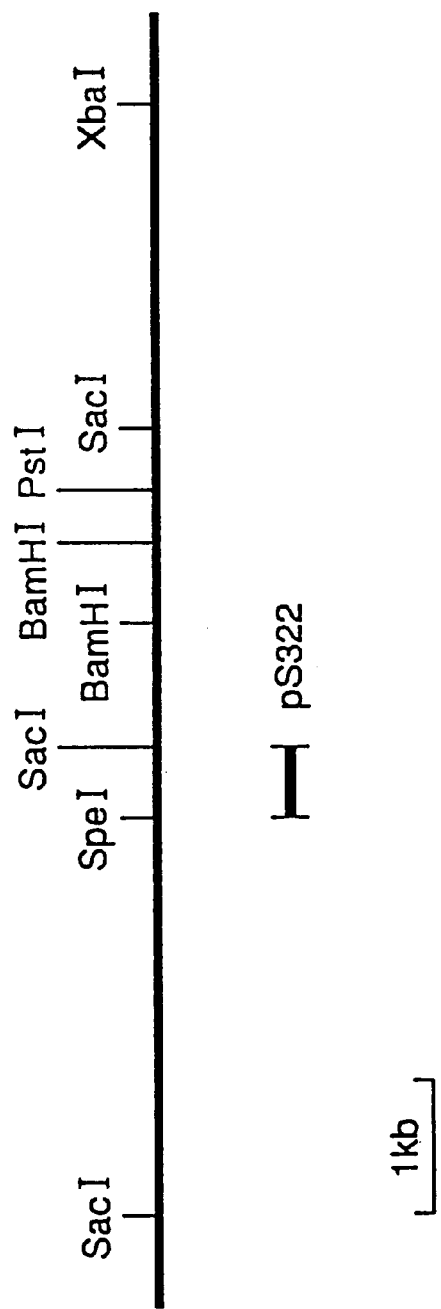
FIG. 13 is a figure showing a restriction map around the protease PFUS gene on the *Pyrococcus furiosus* chromosomal DNA.

A chromosomal DNA of *Pyrococcus furiosus* is digested with SacI or XbaI (both manufactured by Takara Shuzo Co., Ltd.), respectively, which is allowed to intramolecullarly ligate, and this reaction mixture can be used as a template for the inverse PCR. When a chromosomal DNA is digested with SacI, an about 3 kb fragment is amplified by the inverse PCR, which is inserted into the plasmid vector pT7BlueT (manufactured by Novagen) to obtain a recombinant plasmid which was designated the plasmid pS322. On the other hand, in a case of a chromosomal DNA digested with XbaI, an about 9 kb fragment is amplified. The amplified fragment is digested with XbaI to obtain an about 5 kb fragment which is recovered and inserted into the plasmid vector pBluescript SK(−) to obtain a recombinant plasmid, which was designated the plasmid pSKX5. By combining the results of southern hybridization performed using the SpeI-SacI fragment contained in the plasmid pSS3 as a probe, and those of analysis on the plasmids pS322 and pSKX5 with the restriction enzymes, a restriction map of the protease PFUS gene and the vicinity thereof in a chromosome can be obtained. The restriction map is shown in FIG. 13.

In addition, by analyzing the nucleotide sequence on a 5' fragment inserted into the plasmid pS322 in a 5' direction starting from the SpeI site, the amino acid sequence of an enzyme protein encoded by the region can be deduced. The resulting nucleotide sequence and the amino acid sequence deduced therefrom are shown in SEQ ID No. 30 of the Sequence Listing. Since the amino acid sequence of this region has the homology with that of a protease such as subtilisin or the like, an initiation codon of the protease PFUS can be presumed based on this homology and, thus, primer NPF-4 which can introduce the BamHI site in front of the initiation codon of the protease PFUS can be designed. On the other hand, the nucleotide sequence determined by analyzing the nucleotide sequence of a 3' fragment of the protease PFUS gene inserted into the plasmid pSKX5 in a 5' direction starting from the XbaI site is shown in SEQ ID No. 31 of the Sequence Listing. Based on the nucleotide sequence, the primer NPR-4 which can insert the SphI site into the vicinity of the XbaI site can be designed. The nucleotide sequences of the primers NPF-4 and NPR-4 are shown in SEQ ID Nos. 32 and 33 of the Sequence Listing, respectively. The full length protease PFUS gene can be amplified by using these two primers and using a chromosomal DNA of *Pyrococcus furiosus* as a template.

Figure 14:
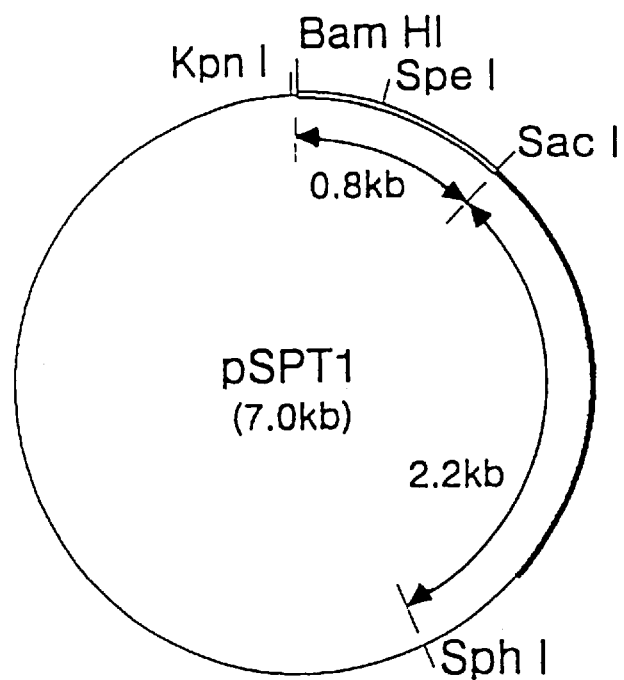
FIG. 14 is a restriction map of the plasmid pSPT1.

The protease PFUS can be expressed in the *Bacillus subtilis* system, as in a case of the protease TCES. A plasmid for expressing the protease PFUS can be constructed based on the expression plasmid pSTC3 for the protease TCES. First, a DNA fragment containing the full length protease PFUS gene which can be amplified by the PCR is digested with BamHI and SacI to recover an about 0.8 kb fragment encoding a N-terminal part of the enzyme. And this fragment is replaced with the BamHI-SacI fragment, also encoding a N-terminal part of the protease TCES, of the plasmid pSTC3. The resulting expression plasmid encoding a hybrid protein of the protease TCES and the protease PFUS gene was designated the plasmid pSPT1. FIG. 14 shows a restriction map of the plasmid pSPT1.

Figure 15:
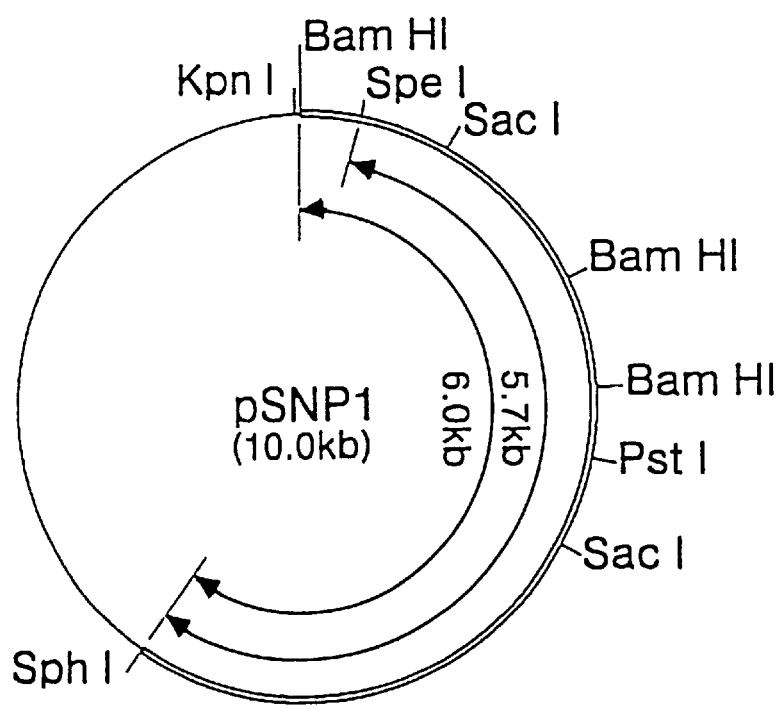
FIG. 15 is a restriction map of the plasmid pSNP1.

Then, the above PCR-amplified DNA fragment is digested with SpeI and SphI to give an about 5.7 kb fragment which is isolated and replaced with the SpeI-SphI fragment encoding a C-terminal part of the protease TCES in the plasmid pSPT1. The expression plasmid thus constructed was designated the plasmid pSNP1, and *Bacillus subtilis* DB104 transformed with the plasmid was designated *Bacillus subtilis* DB104/pSNP1 and has been deposited at National Institute of Bioscience and Human-Technology (NIBH) at 1-1-3, Higashi, Tsukuba-shi, Ibaraki-ken, Japan since Dec. 1, 1995 (original deposit date) as the accession number FERM BP-5634 under Budapest Treaty. FIG. 15 shows a restriction map of the plasmid pSNP1.

The *Bacillus subtilis* DB104/pSNP1 is cultured and a culture supernatant and an extract from the cells are examined for the protease activity and it is found that the thermostable protease activity is found in both samples.

The nucleotide sequence of a gene encoding the protease PFUS can be determined by digesting a DNA fragment inserted into the plasmid pSNP1 with a restriction enzyme into the appropriate sized fragments, subcloning the fragments into an appropriate cloning vector, and conducting the dideoxy method using the subcloned fragments as a template. SEQ ID No. 34 of the Sequence Listing shows the nucleotide sequence of open reading frame present in the nucleotide sequence thus obtained. In addition, SEQ ID No. 35 of the Sequence Listing shows the amino acid sequence of the protease PFUS deduced from the nucleotide sequence.

Further, also when *Bacillus subtilis* DB104 transformed with the plasmid pSPTI, *Bacillus subtilis* DB104/pSPT1, is cultured, the protease activity is found in both a culture supernatant and an extract from the cells. SEQ ID No. 6 of the Sequence Listing shows the nucleotide sequence of open reading frame encoding a hybrid protein of the protease TCES and the protease PFUS. In addition, SEQ ID No. 5 of the Sequence Listing shows the amino acid sequence of the hybrid protein deduced from the nucleotide sequence.

An amount of an expressed protease of the present invention can be increased by utilizing a gene which is highly expressed in *Bacillus subtilis*, particularly a secretory protein gene. As such a gene, the genes of α-amylase and the various extracellular proteases can be used. For example, an amount of the expressed protease PFUS can be increased by utilizing the promoter and the signal sequence of subtilisin. That is, by ligating the full length protease PFUS gene to downstream of a region encoding the signal sequence of subtilisin gene so that the translation frames of both genes coincide with each other, the protease PFUS can be expressed as a fusion protein under the control of subtilisin gene promoter.

As the promoter and the signal sequence of subtilisin, those of subtilisin gene, which are inserted into the plasmid pKWZ, described in J. Bacteriol., volume 171, page 2657–2665 (1989) can be used. The nucleotide sequence of the gene is described in the above literature for a 5' upstream region containing the promoter sequence and in J. Bacteriol., volume 158, page 411–418 (1984) for a region encoding subtilisin, respectively. Based on these sequences, the primer SUB4 for introducing the EcoRI site upstream of the promoter sequence of the gene, and the primer BmRI for introducing the BamHI site behind a region encoding the signal sequence of subtilisin are synthesized, respectively. SEQ ID Nos. 36 and 37 of the Sequence Listing show the nucleotide sequences of the primers SUB4 and BmR1, respectively. By using the primers SUB4 and BmR1 an about 0.3 kb DNA fragment containing the region encoding from the promoter to the signal sequence of subtilisin gene can be amplified by PCR using the plasmid PKWZ as a template.

The protease PFUS gene ligated downstream of the DNA fragment can be taken from a chromosomal DNA of *Pyrococcus furiosus* by the PCR method. As a primer which hybridizes with a 5' part of the gene, the primer NPF-4 can be used. In addition, a primer which hybridizes with a 3' part can be made after the nucleotide sequence downstream of a termination codon of the gene is determined. That is, a portion of the nucleotide sequence of the plasmid PSNPD obtained by subcloning an about 0.6 kb fragment, produced by digestion of the plasmid pSNP1 with BamHI, into the BamHI site of the plasmid vector pUC119 is determined (the nucleotide sequence is SEQ ID No. 38 of the Sequence Listing). Based on the sequence, the primer NPM-1 which hybridizes with a 3' part of the protease PFUS gene and which can introduce the SphI site is synthesized. SEQ ID No. 39 of the Sequence Listing shows the sequence of the primer NPM-1.

On the other hand, when the protease PFUS gene is ligated to the above 0.3 kb DNA fragment by utilizing the BamHI site, only one BamHI site present in the gene becomes a barrier to the procedures. The primers mutRR and mutFR for removing this BamHI site by the PCR-mutagenesis method can be made based on the nucleotide sequence of the protease PFUS gene shown in SEQ ID No. 34 of the Sequence Listing. The nucleotide sequences of the primers mutRR and mutRF are shown in SEQ ID Nos. 40 and 41, respectively. In addition, when the BamHI site is removed by utilizing these primers, glycine present at the position 560 in the amino acid sequence of the protease PFUS shown in SEQ ID No. 35 of the Sequence Listing is substituted with valine due to the nucleotide substitution which is introduced into the site.

By using these primers, the protease PFUS gene to be ligated to the promoter to signal sequence-coding region of subtilisin gene can be obtained. That is, two kinds of PCRs are carried out using a chromosomal DNA of *Pyrococcus furiosus* as a template and using two kinds of pairs of the primers mutRR and NPF-4, and the primers mutFR and NPM-1. Further, the second PCR is carried out using a hetero duplex formed by mixing the DNA fragments amplified by both PCRs as a template, and using the primers NPF-4 and NPM-1. Thus, the full length of the about 2.4 kb protease PFUS gene containing no BamHI site can be amplified.

Figure 16:
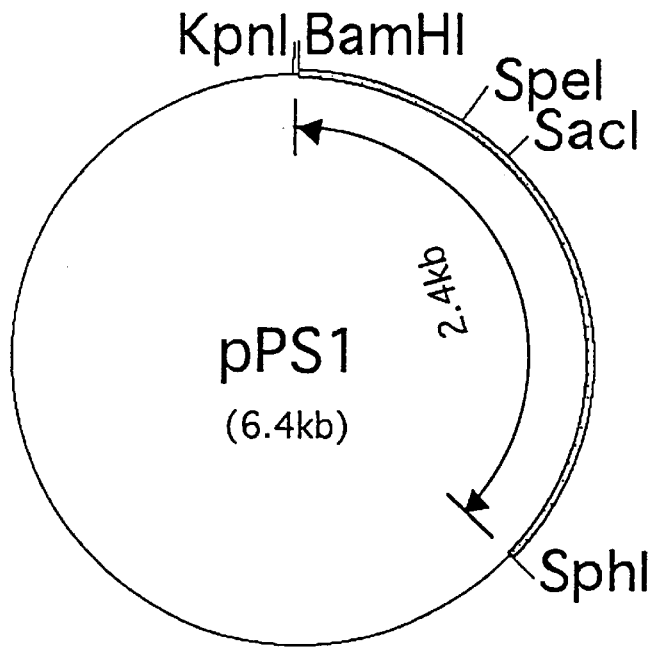
FIG. 16 is a restriction map of the piasmid pPS1.

An about 2.4 kb DNA fragment obtained by digesting the above PCR-amplified DNA fragment with BamHI and SphI is isolated, and replaced with the BamHI-SphI fragment containing the protease PFUS gene in the plasmid pSNP1. The expression plasmid thus constructed was designated pPS1 and *Bacillus subtilis* DB104 transformed with the plasmid was designated *Bacillus subtilis* DB104/pPS1. When the transformant is cultured, the similar protease activity to that in a case of the use of the plasmid pSNP1 is found in both a culture supernatant and an extract from the cells, and it is confirmed that the substitution of the amino acids dose not affect on the enzyme activity. FIG. 16 shows a restriction map of the plasmid pPS1.

Figure 17:
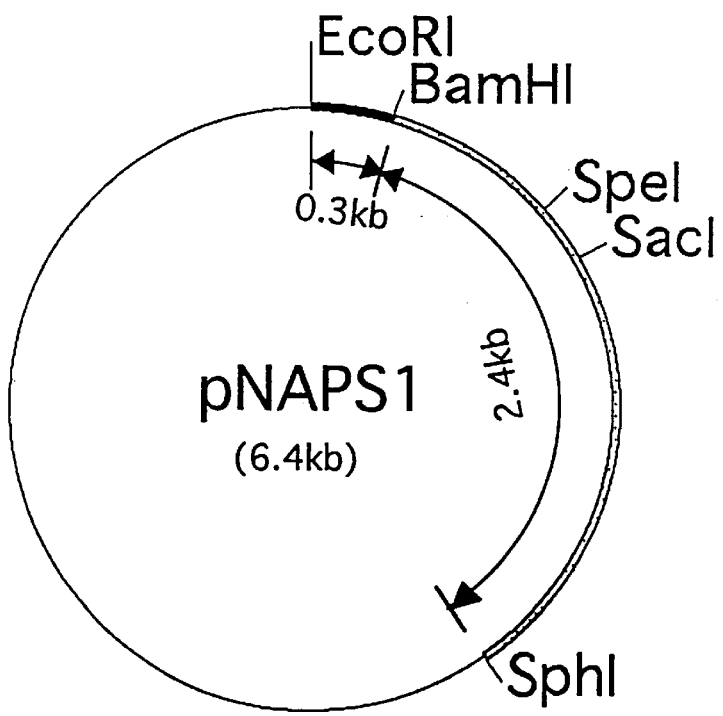
FIG. 17 is a restriction map of the plasmid pNAPS1.

An about 0.3 kb DNA fragment containing from the promoter to the signal sequence of the subtilisin is digested with EcoRI and BamHI, and substituted with the EcoRI-BamHI fragment containing the P43 promoter and the ribosome binding site in the plasmid pPS1. The expression plasmid thus constructed was designated pNAPS1 and *Bacillus subtilis* transformed with the plasmid was designated *Bacillus subtilis* DB104/pNAPS1. The transformant is cultured, a culture supernatant and an extract from the cells are examined for the protease activity to be found that the protease activity is recognized in both samples. An amount of expressed enzyme is increased as compared with *Bacillus subtilis* DB104/pSN1. FIG. 17 shows a restriction map of the plasmid pNAPS1.

By a similar method to that in a case of the protease TCES gene and the protease PFUS gene, a protease gene having the homology with these genes can be obtained from hyperthermophiles other than *Pyrococcus furiosus* and *Thermococcus celer*. However, in PCR using the above oligonucleotides PRO-1F, PRO-2F, PRO-2R and PRO-4R as a primer and using a chromosomal DNA of *Staphylothermus marinus* DSM3639 and that of *Thermobacteroides proteoliticus* DSM5265 as a template, the amplification of a DNA fragment as found in *Thermococcus celer* was not found.

In addition, it is known that the efficiency of gene amplification by PCR is largely influenced by the efficiency of annealing of a 3' terminal part of a primer and a template DNA. Even when the amplification of a DNA by PCR is not observed, a protease gene can be detected by synthesizing and using the oligonucleotides having the different nucleotide sequence from that used this time but encoding the same amino acid sequence. Alternatively, a protease gene can be also detected by conducting southern hybridization using a chromosomal DNA and using the above oligonucleotides or a portion of other hyperthermostable protease genes as a probe.

An about 1 kb DNA fragment encoding the sequence of residue 323 to residue 650 of the amino acid sequence of the protease PFUL represented by SEQ ID No. 8 of the Sequence Listing is prepared, and this can be used as a probe to conduct genomic southern hybridization using a chromosomal DNA of *StaPhylothermus marinus* DSM3639 and that of *Thermobacteroides proteoliticus* DSM5265. As a result, when the *Staphylothermus marinus* chromosomal DNA digested with PstI (manufactured by Takara Shuzo Co., Ltd.) is used, a signal is observed at the position of about 4.8 kb. On the other hand, when the *Thermobacteroides proteoliticus* chromosomal DNA digested with XbaI is used, a signal is observed at the position of about 3.5 kb.

From this, it is revealed that a sequence having the homology with the protease PFUL, the protease PFUS and the protease TCES gene is present also in the *Staphylothermus marinus* and *Thermobacteroides proteoliticus* DNA chromosomes. From the DNA fragment thus detected, a gene encoding a hyperthermostable protease present in *Staphylothermus marinus* or *Thermobacteroides proteoliticus* can be isolated and identified by using the same method as that when the gene encoding the protease TCES or the protease PFUS is isolated and identified.

The transformant in which the protease TCES gene, a hyperthermostable protease gene of the present invention, is introduced (*Bacillus subtilis* DB104/pSTC3) expresses a hyperthermostable protease in a culture by culturing at 37° C. in LB medium containing 10μg/ml kanamycin. After the completion of cultivation, crude enzyme preparation is obtained by subjecting centrifugation of a culture to collect a supernatant, and salting out with ammonium sulfate and dialysis. Thus, the crude enzyme preparation obtained from *Bacillus subtilis* DB104/pSTC3 was designated TC-3.

According to the similar procedures, a crude enzyme preparation can be obtained from the transformant *Bacillus subtilis* DB101/pSNP1 in which the protease PFUS gene is introduced, or from the transformant *Bacillus subtilis* DB104/pSPT1 in which a gene encoding a hybrid protease of the protease TCES and the protease PFUS. Crude enzyme preparations obtained from *Bacillus subtilis* DB104/pSNP1 and *Bacillus subtilis* DB104/pSPT1 were designated NP-1 and PT-1, respectively.

Transformant *Bacillus subtilis* DB104/pNAPS1 in which the protease PFUS gene, a hyperthermostable protease gene of the present invention, is introduced expresses a hyperthermostable protease in the cells or culture under the conventional conditions, for example, by culturing at 37° C. in LB medium containing 10 μg/ml kanamycin. After the completion of cultivation, the cells and a culture supernatant are separated by centrifugation, from either of which a crude enzyme preparation of the protease PFUS can be obtained by the following procedures.

When an enzyme is purified from the cells, the cells are first lysed by the lysozyme treatment, the lysate is heat-treated and centrifuged to recover a supernatant. This supernatant can be fractionated with ammonium sulfate and subjected to hydrophobic chromatography to obtain a purified enzyme. The purified enzyme preparation thus obtained from *Bacillus subtilis* DB104/pNAPS1 was designated NAPS-1.

On the other hand, the culture supernatant is dialyzed and subjected to anion-exchange chromatography. The eluted active fractions can be collected, heat-treated, fractionated with ammonium sulfate, and subjected to hydrophobic chromatography to obtain a purified enzyme of the protease PFUS. The purified enzyme preparation was designated NAPS-1S.

When the purified products NAPS-1 and NAPS-1S thus obtained are subjected to SDS-polyacrylamide gel electrophoresis, both enzyme preparation show a single band corresponding to a molecular weight of about 45 kDa. These two enzyme preparation are substantially the same enzyme preparation which have been converted into a mature (active-type) enzyme by removing a pro sequence by heat-treatment during the purification procedures.

The protease preparation produced by the transformants in which a hyperthermostable protease gene obtained by the present invention is introduced, for example, TC-3, NP-1, PT-1, NAPS-1 and NAPS-1S have the following enzymatic and physicochemical properties.

(1) Activity

The enzymes obtained in the present invention hydrolyze gelatin to produce the short-chain polypeptides. In addition, the enzymes hydrolyze casein to produce short-chain polypeptides.

In addition, the enzymes obtained in the present invention hydrolyze succinyl-L-leucyl-L-leucyl-L-valyl-L-tyrosine-4-methylcoumarin-7-amide (Suc-Leu-Leu-Val-Tyr-MCA) to produce a fluorescent material (7-amino-4-methylcoumarin).

Further, the enzymes obtained in the present invention hydrolyze succinyl-L-alanyl-L-alanyl-L-prolyl-L-phenylalanine-p-nitroanilide (Suc-Ala-Ala-Pro-Phe-p-NA) to produce a yellow material (p-nitroaniline).

(2) Method for measuring enzyme activity

The enzyme activity of the enzyme preparations obtained in the present invention can be measured using a synthetic peptide substrate.

The enzyme activity of the enzyme preparation TC-3 obtained in the present invention can be measured using as a substrate Suc-Leu-Leu-Val-Tyr-MCA (manufactured by Peptide Laboratory). That is, the enzyme preparation to be detected for the enzyme activity is appropriately diluted, to 20 µl of the solution is added 80 µl of a 0.1M sodium phosphate buffer (pH 7.0) containing 62.5 µM Suc-Leu-Leu-Val-Tyr-MCA, followed by incubating at 75° C. for 30 minutes. After the reaction is stopped by the addition of 20 µl of 30% acetic acid, the fluorescent intensity is measured at the excitation wavelength of 355 nm and the fluorescence wavelength of 460 nm to quantitate an amount of the generated 7-amino-4-methylcoumarin, and the resulting value is compared with that obtained when incubating without the addition of the enzyme preparation, to investigate the enzyme activity. The enzyme preparation TC-3 obtained by the present invention had the Suc-Leu-Leu-Val-Tyr-MCA hydrolyzing activity measured at pH 7.0 and 75° C.

In addition, the enzyme activity of the enzyme preparations NP-1, PT-1, NAPS-1 and NAPS-1S can be photometrically measured using Suc-Ala-Ala-Pro-Phe-p-NA (manufactured by Sigma) as a substrate. That is, an enzyme preparation to be detected for the enzyme activity was appropriately diluted, to 50 µl of the solution was added 50 µl of a 0.1M potassium phosphate buffer (pH 7.0) containing Suc-Ala-Ala-Pro-Phe-p-NA (Suc-Ala-Ala-Pro-Phe-p-NA solution), followed by incubating at 95° C. for 30 minutes. After the reaction was stopped by ice-cooling, the absorbance at 405 nm was measured to quantitate an amount of the generated p-nitroaniline, and the resulting value was compared with that when incubating without the addition of the enzyme preparation, to investigate the enzyme activity. Upon this, a 0.2 mM solution of Suc-Ala-Ala-Pro-Phe-p-NA was used for the enzyme preparations NP-1 and PT-1 and a 1 mM solution was used for the enzyme preparations NAPS-1 and NAPS-1S. The enzyme preparations NP-1, PT-1, NAPS-1 and NAPS-1S obtained by the present invention have the Suc-Ala-Ala-Pro-Phe-p-NA hydrolyzing activity at measured pH 7.0 and 95° C.

(3) Detection of activity on various substrates

The activity of the enzyme preparations obtained in the present invention on the synthetic peptide substrates is confirmed by a method for measuring the enzyme activity described in the above (2). That is, the enzyme preparation TC-3 obtained in the present invention has the Suc-Leu-Leu-Val-Tyr-MCA hydrolyzing activity, and the enzyme preparations NP-1, PT-1, NAPS-1 and NAPS-1A have the Suc-Ala-Ala-Pro-Phe-p-NAhydrlyzing activity, respectively. In addition, the enzyme preparations NP-1, PT-1, NAPS-1 and NAPS-1S were investigated for the Suc-Leu-Leu-Val-Tyr-MCA hydrlyzing activity by the enzyme activity measuring method described in the above (2) used for the enzyme preparation TC-3, and it was shown that these enzyme preparations had the activity to degrade the substrates. Further, the enzyme preparation TC-3 was investigated for the Suc-Ala-Ala-Pro-Phe-p-NA hydrlyzing activity by the enzyme activity measuring method described in the above (2) used for the enzyme preparations NP-1 and PT-1, and the activity to degrade the substrate was recognized. In addition, the activity of the enzyme preparations obtained in the present invention on gelatin can be detected by confirming the degradation of gelatin by an enzyme on the SDS-polyacrylamide gel. That is, the enzyme preparation to be detected for the enzyme activity was appropriately diluted, to 10 µl of the sample solution was added 2.5 µl of a sample buffer (50 mM Tris-HCl, pH 7.5, 5% SDS, 5% 2-mercaptoethanol, 0.005% Bromophenol Blue. 50% glycerol), followed by treatment at 100 ° C. for 5 minutes and electrophoresis using 0.1% SDS-10% polyacrylamide gel containing 0.05% gelatin. After the completion of run, the gel was soaked in a 50 mM potassium phosphate buffer (pH 7.0), and incubated at 95° C. for 3 hours to carry out the enzyme reaction. Then, the gel was stained in 2.5% Coomassie Brilliant Blue R-250, 25% ethanol and 10% acetic acid for 30 minutes, and transferred in 7% acetic acid to remove the excess dye over 3 to 15 hours. The presence of the protease activity was detected by the fact that gelatin is hydrolyzed by a protease into peptides which are diffused out of the gel and, consequently, the relevant portion of the gel was not stained with Coomassie Brilliant Blue. The enzyme preparations TC-3, NP-1, PT-1, NAPS-1 and NAPS-1S obtained by the present invention had the gelatin hydrolyzing activity at 95° C.

In addition, the enzyme preparations NP-1, NAPS-1 and NSPA-1S derived from the protease PFUS gene are recognized to have the gelatin hydrlyzing activity at the almost same positions on the gel in the above activity measuring method. From this, it is shown that, in these enzyme preparations, the processing from a precursor enzyme into a mature type enzyme occurs in the similar manner.

Further, the hydrolyzing activity on casein can be detected according to the same method as that used for detecting the activity on gelatin except that 0.1% SDS-10% polyacrylamide gel containing 0.05% casein is used. The enzyme preparations TC-3, NP-1, PT-1, NAPS-1 and NAPS-1S obtained by the present invention had the casein hydrolyzing activity at 95° C.

Alternatively, the casein hydrolyzing activity of the enzyme preparations TC-3, NP-1, NAPS-1 and NAPS-1S obtained by the present invention can be measured by the following method. 100 µl of an appropriately diluted enzyme preparation was added to 100 µl of a 0.1M potassium phosphate buffer (pH 7.0) containing 0.2% casein, incubated at 95° C. for 1 hour, and the reaction was stopped by the addition of 100 μl of 15% trichloroacetic acid. An amount of an acid-soluble short-chain polypeptide contained in the supernatant obtained by centrifugation of this reaction mixture was determined from the absorbance at 280 nm and compared with that when incubating without the addition of an enzyme preparation, to investigate the enzyme activity. The enzyme preparations TC-3, NP-1, NAPS-1 and NAPS-1S obtained by the present invention had the casein hydrolyzing activity at 95° C.

(4) Optimum temperature

Figure 18:
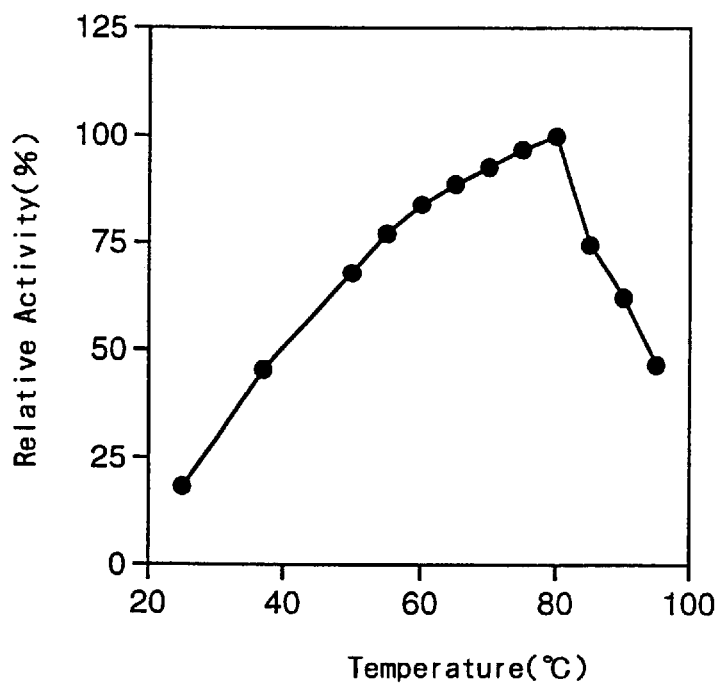
FIG. 18 is a figure showing the optimum temperature for the enzyme preparation TC-3.

The optimum temperature of the enzyme preparation TC-3 obtained by the present invention was investigated using the enzyme activity measuring method shown in the above (2) except for varying a temperature. As shown in FIG. 18, the enzyme preparation TC-3 showed the activity at a temperature of 37 to 95° C. and the optimum temperature thereof was 70 to 80° C. That is, FIG. 18 is a figure showing the relationship between the activity of the enzyme preparation TC-3 obtained in the present invention and a temperature, and the ordinate shows the relative activity to the maximum activity (%) and the abscissa shows a temperature.

Figure 19:
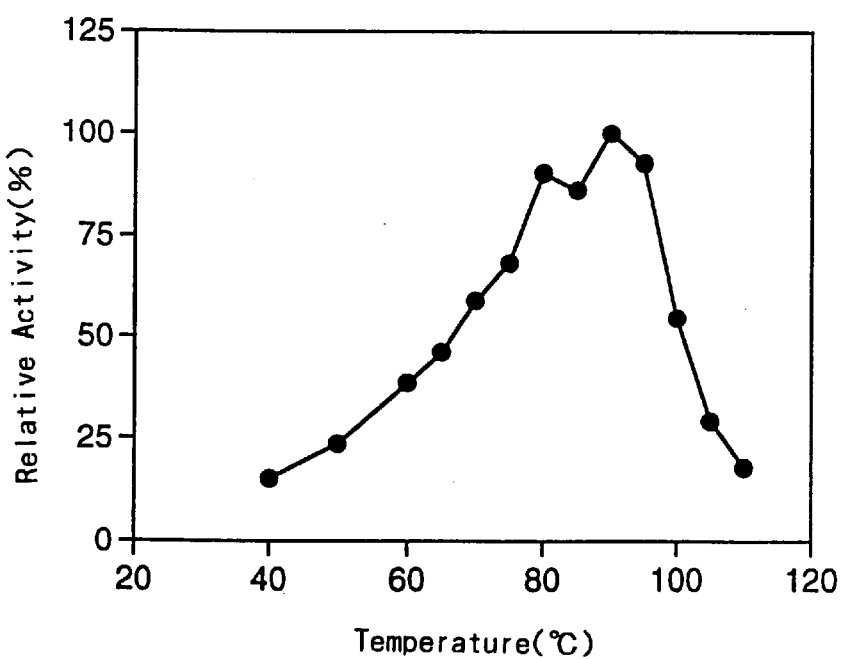
FIG. 19 is a figure showing the optimum temperature for the enzyme preparation NAPS-1.

In addition, the optimum temperature of the enzyme preparation NAPS-1 obtained in the present invention was investigated by using the enzyme activity measuring method shown in the above (2) except for varying a temperature. As shown in FIG. 19, the enzyme preparation NAPS-1 had the activity at a temperature between 40 to 110° C. at the measuring conditions of pH 7.0, and the optimum temperature being 80 to 95 ° C. That is, FIG. 19 is a figure showing the relationship between the activity of the enzyme preparation NAPS-1 obtained in the present invention and a temperature, and the ordinate shows the relative activity to the maximum activity (%) and the abscissa shows a temperature.

(5) Optimum pH

Figure 20:
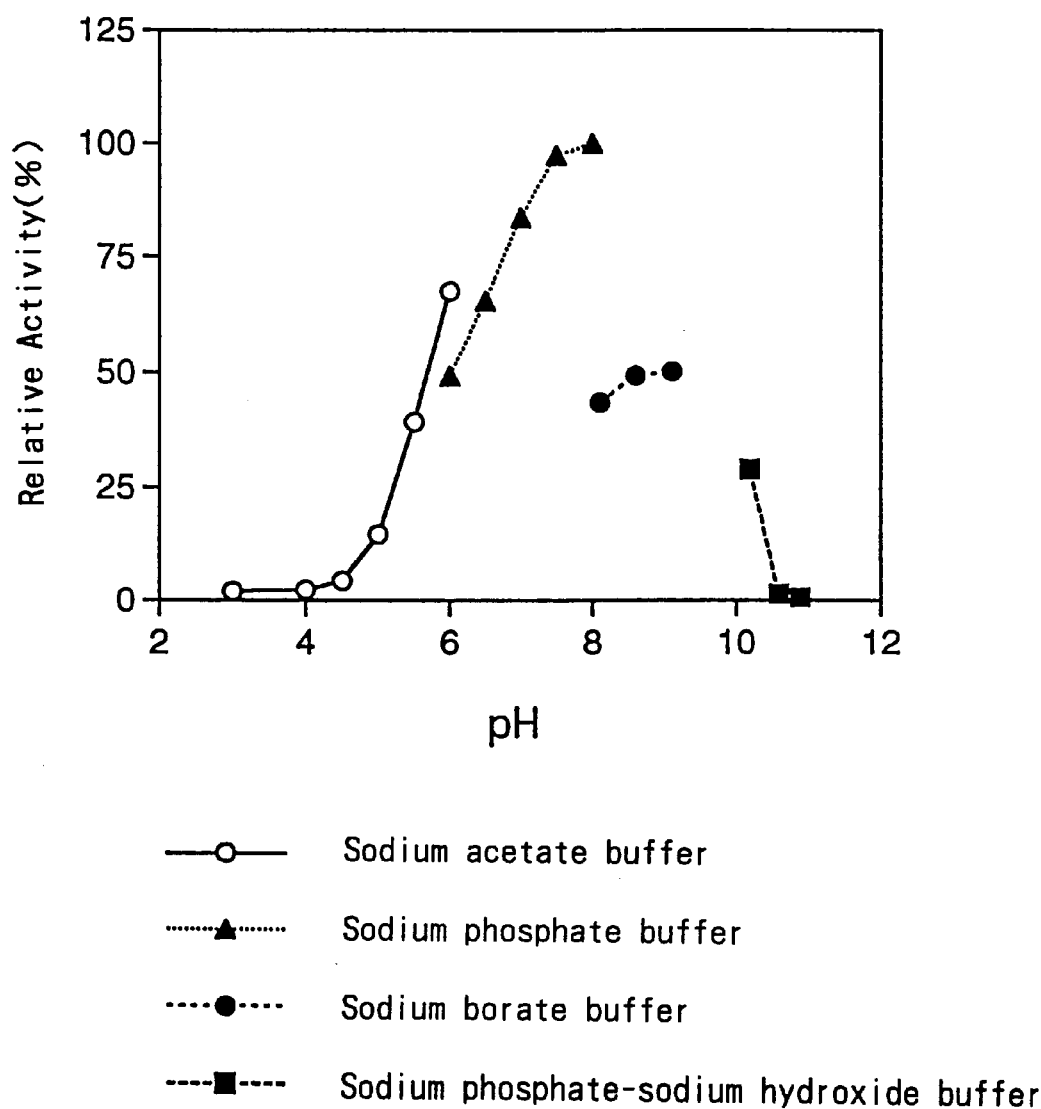
FIG. 20 is a figure showing the optimum pH for the enzyme preparation TC-3.

The optimum pH of the enzyme preparation TC-3 obtained by the present invention was investigated by the enzyme activity measuring method shown in the above (2). That is, the Suc-Leu-Leu-Val-Tyr-MCA solutions were prepared using the buffers having various pHs, and the enzyme activities obtained by using these solutions were compared. As a buffer, a sodium acetate buffer was used at pH 3 to 6, a sodium phosphate buffer at pH 6 to 8, a sodium borate buffer at pH 8 to 9, and a sodium phosphate-sodium hydroxide buffer at pH 10 to 11. As shown in FIG. 20, the enzyme preparation TC-3 shows the activity at pH 5.5 to 9, and the optimum pH was pH 7 to 8. That is, FIG. 20 is a figure showing the relationship between the activity of the enzyme preparation TC-3 obtained in the present invention and pH, and the ordinate shows the relative activity (%) and the abscissa shows pH.

Figure 21:
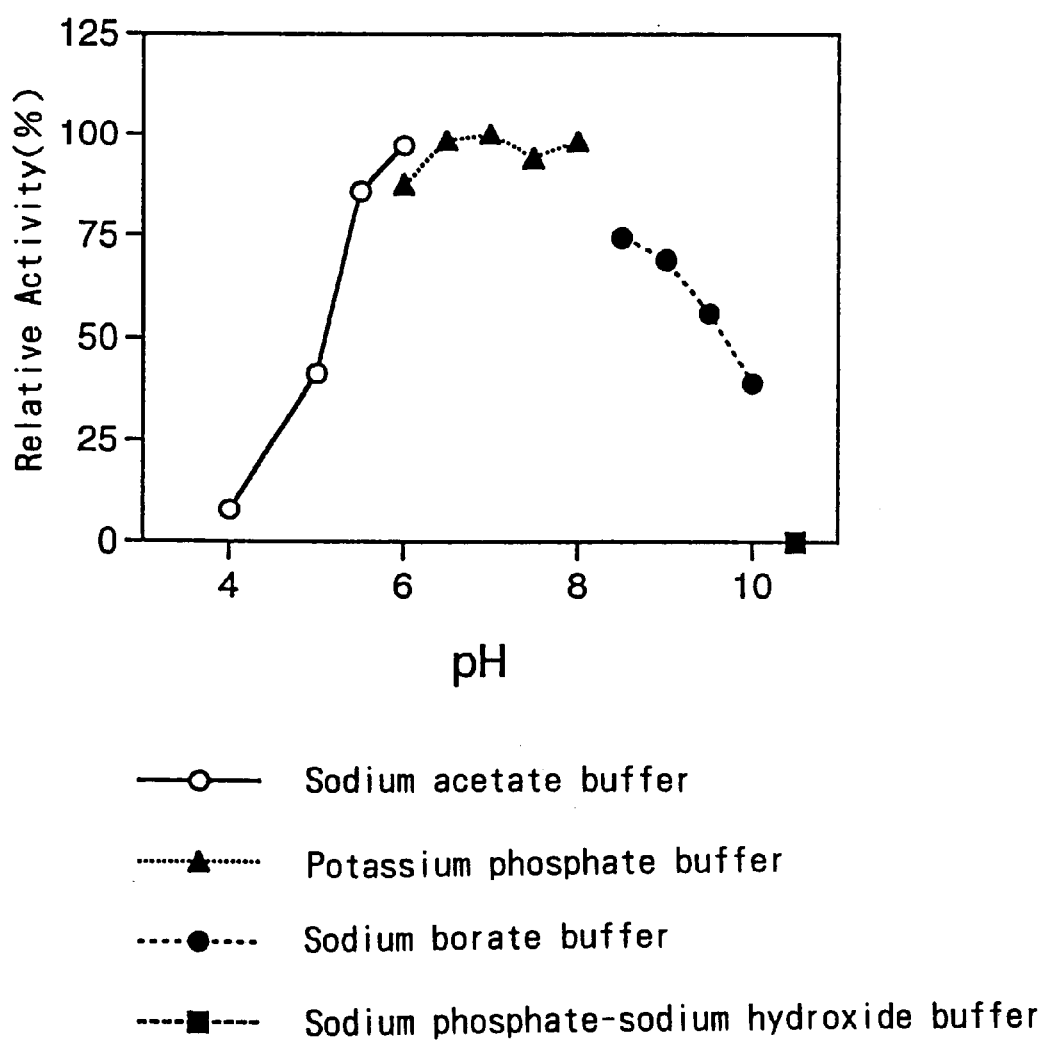
FIG. 21 is a figure showing the optimum pH for the enzyme preparation NP-1.

In addition, the optimum pH of the enzyme preparation NP-1 obtained in the present invention was investigated by the enzyme activity measuring method shown in the above (2). That is, the Suc-Ala-Ala-Pro-Phe-pNA solutions were prepared by using the buffers having various pHs, and the enzyme activities obtained by using these solution were compared. As a buffer, a sodium acetate buffer was used at pH 4 to 6, a potassium phosphate at pH 6 to 8, a sodium borate buffer at pH 5 to 10, and a sodium phosphate-sodium hydroxide buffer at pH 10.5. As shown in FIG. 21, the enzyme preparation NP-1 shows the activity at pH 5 to 10, and the optimum pH was pH 5.5 to 8. That is, FIG. 21 is a figure showing the relationship between the activity of the enzyme preparation NP-1 obtained in the present invention and pH, and the ordinate shows the relative activity (%) and the abscissa shows pH.

Figure 22:
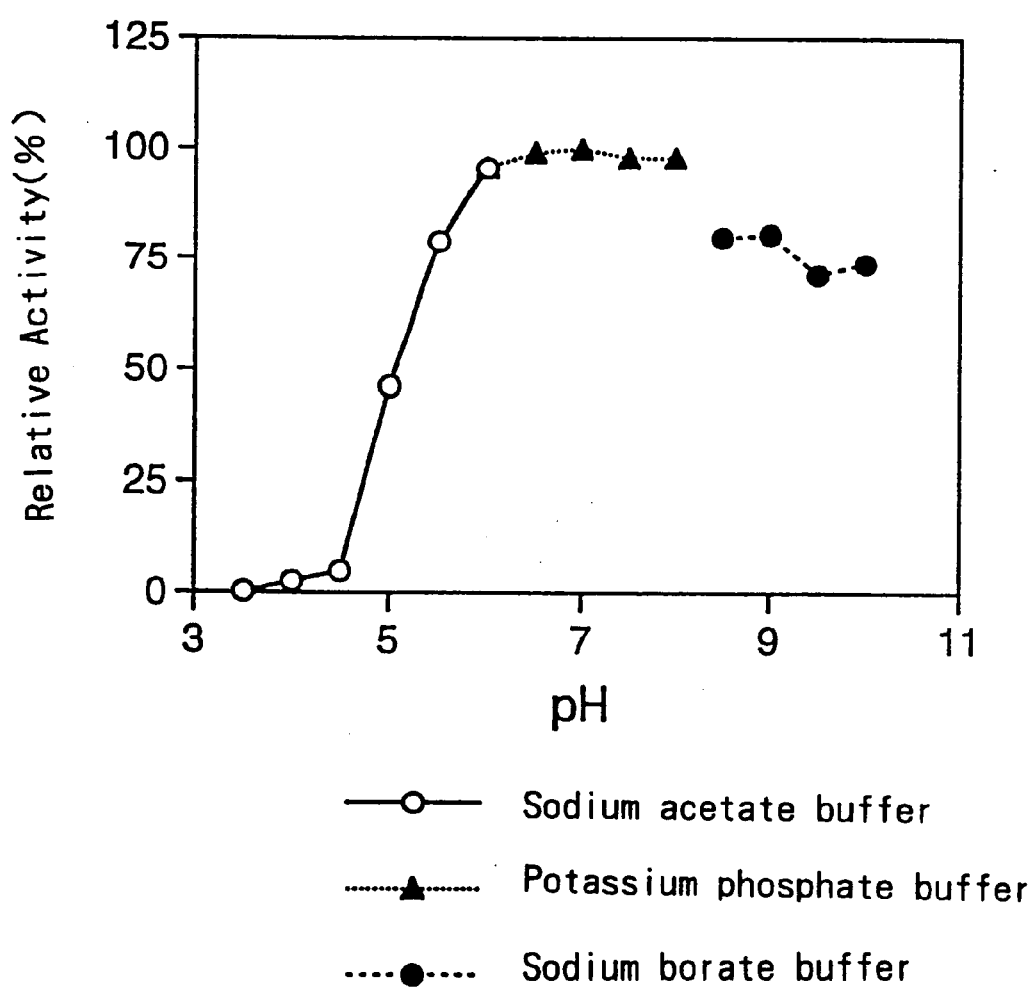
FIG. 22 is a figure showing the optimum pH for the enzyme preparation NAPS-1.

Further, the optimum pH of the enzyme preparation NAPS-1 obtained in the present invention was investigated by the enzyme activity measuring method shown in the above (2). That is, the Suc-Ala-Ala-Pro-Phe-pNA solutions were prepared by using the buffers having various pHs, and the enzyme activities obtained by using these solution were compared. As a buffer, a sodium acetate buffer was used at pH 4 to 6, a potassium phosphate at pH 6 to 8, a sodium borate buffer at pH 8.5 to 10. As shown in FIG. 22, the enzyme preparation NAPS-1 shows the activity at pH 5 to 10, and the optimum pH was pH 6 to 8. That is, FIG. 22 is a figure showing the relationship between the activity of the enzyme preparation NAPS-1 obtained in the present invention and pH, and the ordinate shows the relative activity (%) and the abscissa shows pH.

(6) Thermostability

Figure 23:
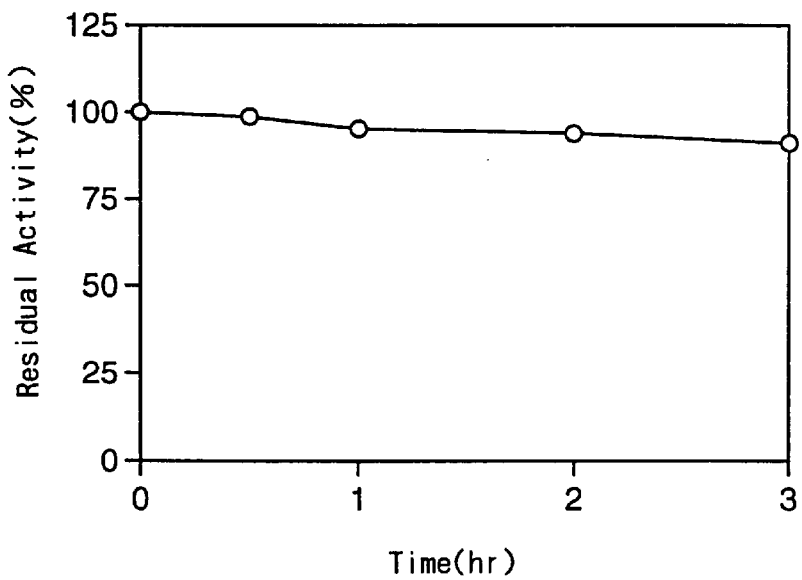
FIG. 23 is a figure showing the thermostability of the enzyme preparation TC-3.

The thermostability of the enzyme preparation TC-3 obtained by the present invention was investigated. That is, the enzyme preparation was incubated at 80° C. in 20 mM Tris-HCl, pH 7.5 for various periods of time, an appropriate amount thereof was taken to measure the enzyme activity by the method shown in the above (2), and the activity was compared with that when not heat-treated. As shown in FIG. 23, the enzyme preparation TC-3 obtained by the present invention had not less than 90% of the activity even after the heat-treatment for 3 hours and, thus, was stable on the above heat-treatment. That is, FIG. 23 is a figure showing the thermostability of the enzyme preparation TC-3 obtained in the present invention, and the ordinate shows the residual activity (%) after the heat-treatment and the abscissa shows time.

Figure 24:
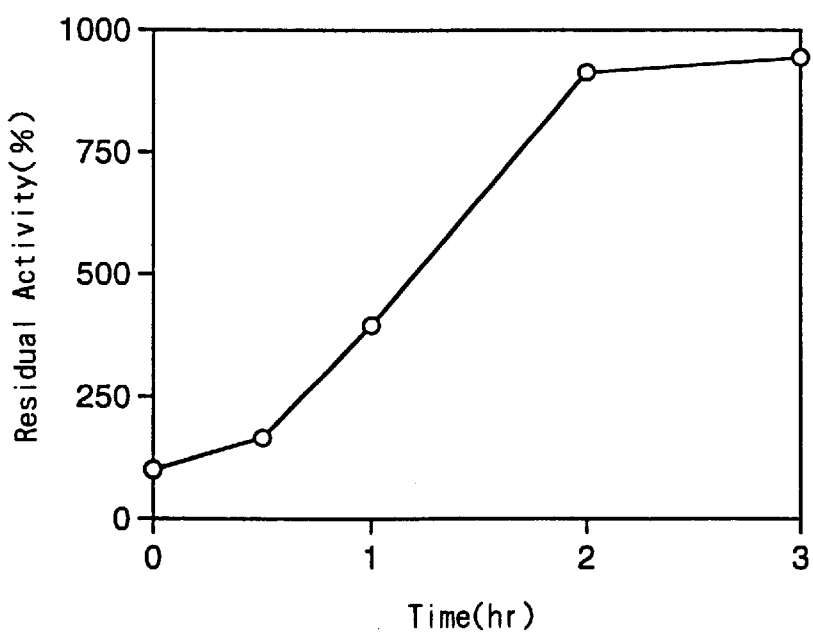
FIG. 24 is a figure showing the thermostability of the enzyme preparation NP-1.

In addition, the thermostability of the enzyme preparation NP-1 obtained in the present invention was investigated. That is, the enzyme preparation was incubated at 95° C. in 20 mM Tris-HCl, pH 7.5 for various periods of time, an appropriate aliquot was taken to determine the enzyme activity by the method shown in the above (2), and the enzyme activity was compared with that when not heat-treated. As shown in FIG. 24, the enzyme preparation NP-1 obtained in the present invention is observed to have the remarkably increased enzyme activity when incubated at 95° C. This is considered to be because a protease produced as a precursor causes the self-catalytic activation during the heat-treatment. In addition, no decrease in the activity was recognized in the heat-treatment for up to 3 hours. That is, FIG. 24 is a figure showing the thermostability of the enzyme preparation NP-1 obtained in the present invention, and the ordinate shows the residual activity (%) after the heat-treatment and the abscissa shows time.

Figure 25:
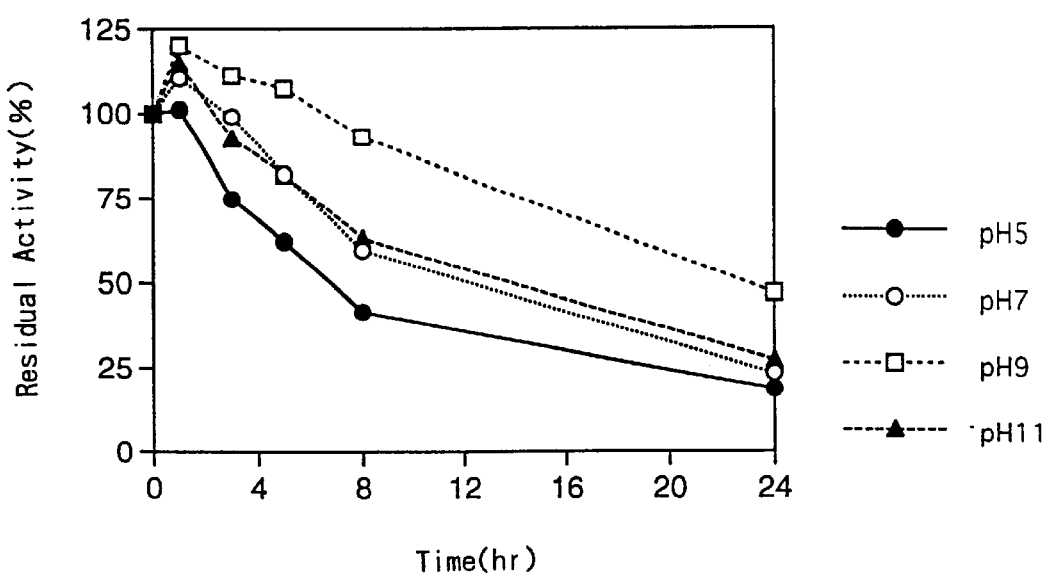
FIG. 25 is a figure showing the thermostability of the activated enzyme preparation NP-1.

In addition, the above enzyme preparation NP-1 activated by the heat-treatment was investigated for the thermostability. That is, the enzyme preparation NP-1 was activated by the heat-treatment at 95° C. for 30 minutes, incubated at 95° C. for various periods of time, and the activity was determined as described above to compare with that when not heat-treated. At the same time, buffers having the various pHs (sodium acetate buffer at pH 5, potassium phosphate buffer at pH 7, sodium borate buffer at pH 9, sodium phosphate-sodium hydroxide buffer at pH 11, 20 mM in every case) were used. As shown in FIG. 25, when the activated enzyme preparation NP-1 obtained in the present invention was treated in a buffer at pH 9, it had not less than 90% of the activity after the heat-treatment for 8 hours and approximately 50% of the activity even after the heat-treatment for 24 hours and, thus, being very stable to the above heat-treatment. That is, FIG. 25 is a figure showing the thermostability of the enzyme preparation NP-1 obtained in the present invention, and the ordinate shows the residual activity (%) after the heat-treatment and the abscissa shows time.

Figure 26:
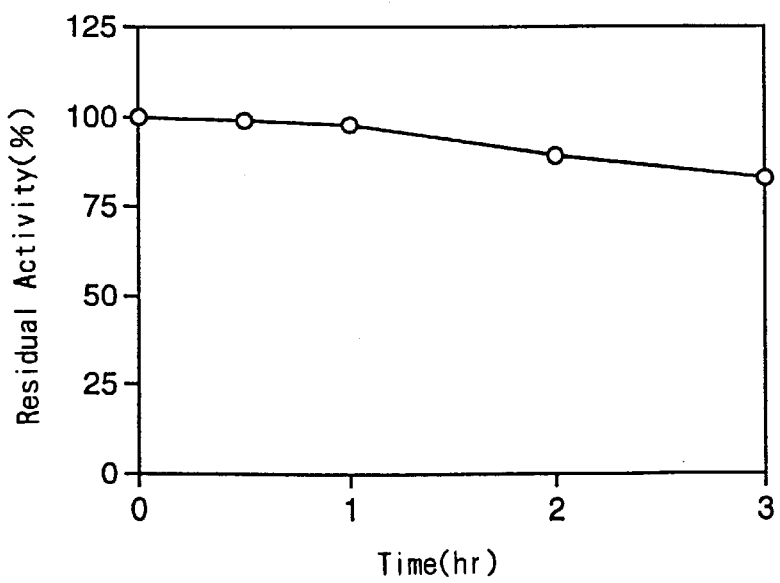
FIG. 26 is a figure showing the thermostability of the enzyme preparation NAPS-1.

In addition, the enzyme preparation NAPS-1 obtained by the present invention was investigated for the thermostability. That is, a temperature of the enzyme preparation was maintained at 95° C. in 20 mM Tris-HCl, pH 7.5 for various periods of time, an appropriate aliquot was taken to determine the enzyme activity by the method shown in the above (2) to compare with that when not heat-treated. As shown in FIG. 26, the enzyme preparation NAPS-1 obtained by the present invention had not less than 80% of the activity even after the heat-treatment at 95° C. for 3 hours and, thus, being stable against the above heat-treatment. That is, FIG. 26 is a figure showing the thermostability of the enzyme preparation NAPS obtained in the present invention, and the ordinate shows the residual activity (%) after the heat-treatment and the abscissa shows time.

(7) pH stability

Figure 27:
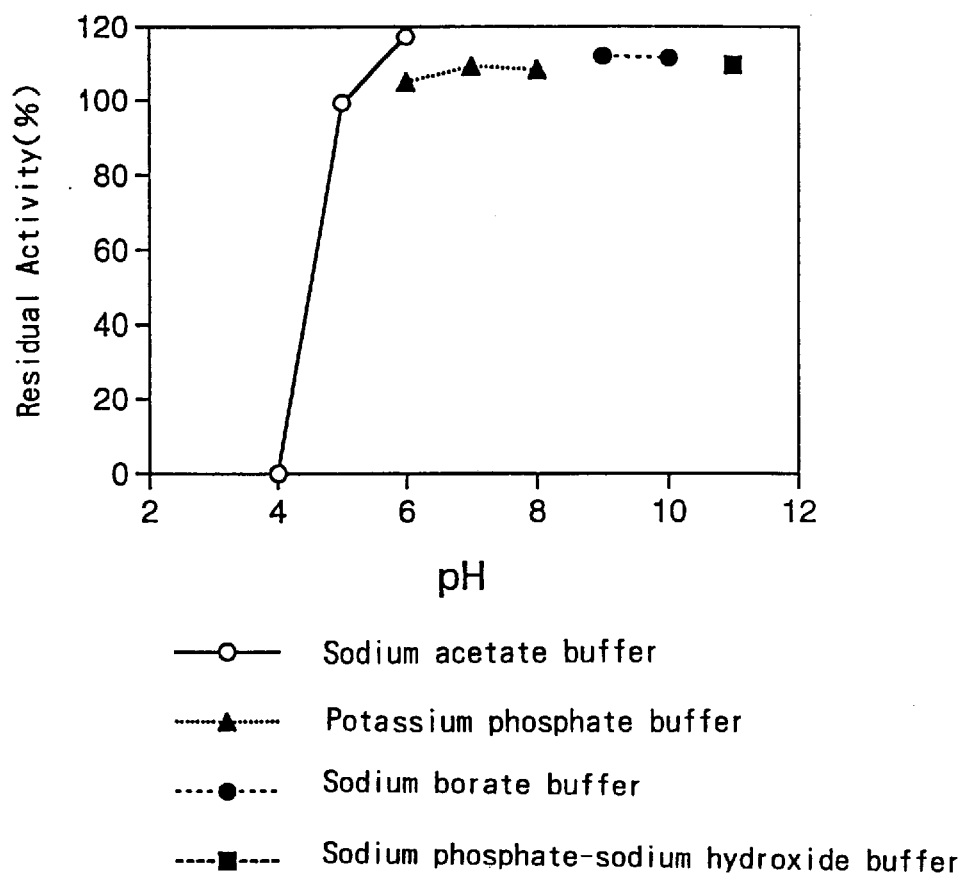
FIG. 27 is a figure showing the pH-stability of the enzyme preparation NP-1.

The pH stability of the enzyme preparation NP-1 obtained by the present invention was investigated according to the following procedures. Each 50 μl of 20 mM buffers at various pHs, which contain the enzyme preparation NP-1 activated by the heat-treatment at 95° C. for 30 minutes, was treated at 95° C. for 60 minutes, and an appropriate aliquot was taken to determine the enzyme activity by the method shown in the above (2) to compare with that when not treated. As a buffer, a sodium acetate buffer was used at pH 4 to 6, a potassium phosphate buffer at pH 6 to 8, a sodium borate buffer at pH 9 to 10, a sodium phosphate-sodium hydroxide buffer at pH 11. As shown in FIG. 27, the enzyme preparation NP-1 obtained by the present invention retained not less than 95% of the activity even after the treatment at 95° C. for 60 minutes at pH between 5 and 11. That is, FIG. 27 is a figure showing the pH stability of the enzyme obtained by the present invention, and the ordinate shows the residual activity (%) and abscissa shows pH.

(8) Stability to detergent

Figure 28:
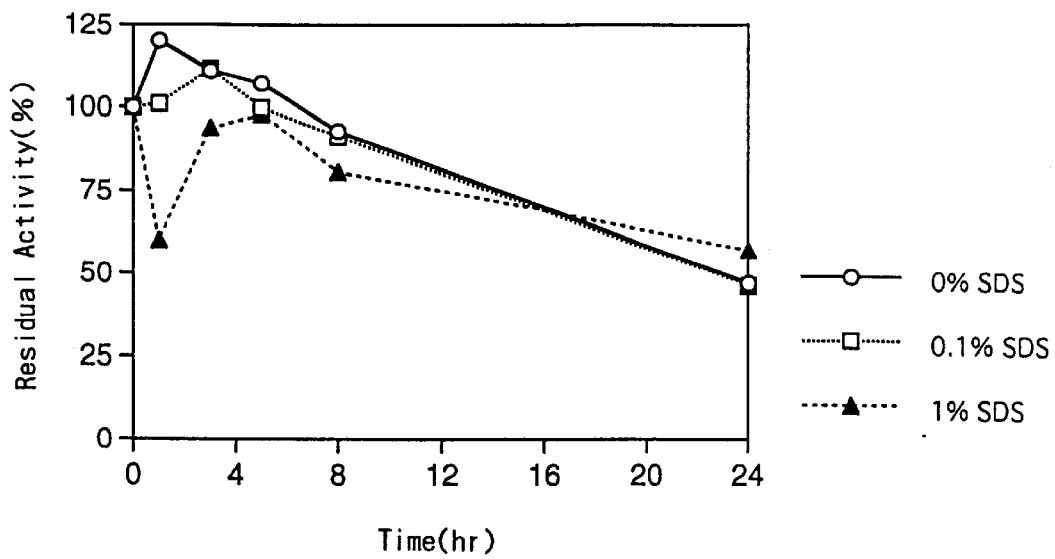
FIG. 28 is a figure showing the stability of the enzyme preparation NP-1 in the presence of SDS.

The stability to detergent of the enzyme preparation NP-1 obtained by the present invention was investigated using SDS as detergent. The enzyme preparation NP-1 was activated by the heat-treatment at 95° C. for 30 minutes. Each 50 μl of a solution containing only the enzyme preparation and a solution further containing SDS to the final concentration of 0.1% or 1% was prepared. These solutions were incubated at 95° C. for various periods of time, an appropriate amount thereof was taken to determine the enzyme activity by the method described in the above (2) to compare with that when not treated. As shown in FIG. 28, the activated enzyme preparation NP-1 obtained by the present invention had not less than 80% of the activity after the heat-treatment at 95° C. for 8 hours and approximately 50% of the activity even the after heat-treatment for 24 hours independently of the presence of SDS and, thus, having the high stability even in the presence of SDS. That is, FIG. 28 is a figure showing the stability to SDS of the enzyme preparation NP-1 obtained by the present invention, and the ordinate shows the residual activity (%) and the abscissa shows time.

Figure 29:
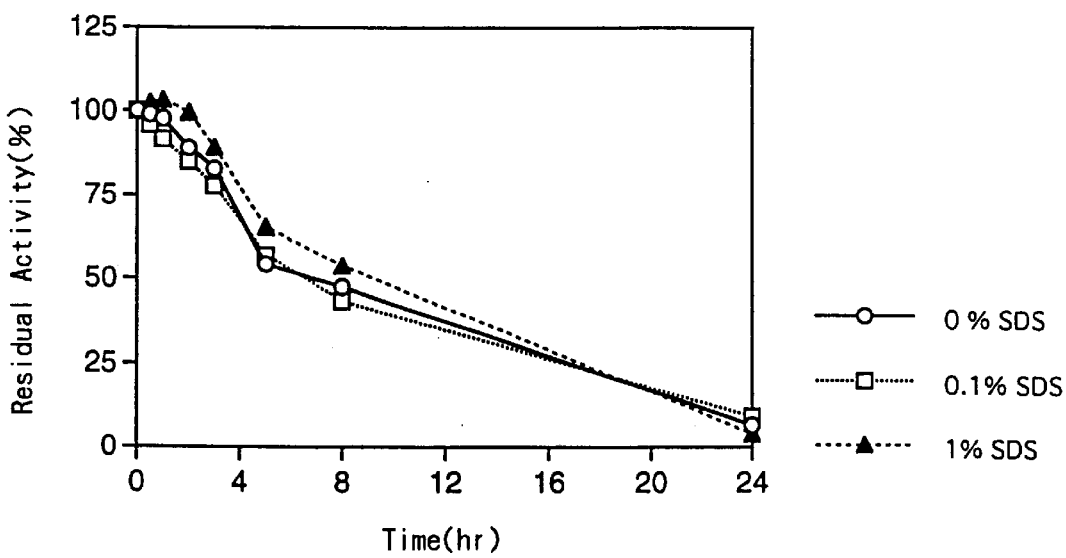
FIG. 29 is a figure showing the stability of the enzyme preparation NAPS-1 in the presence of SDS.

In addition, the stability to detergent of the enzyme preparation NAPS-1 obtained by the present invention was investigated using SDS as detergent. Each 50 μl of a solution containing only the enzyme preparation NAPS-1 and a solution further containing SDS to the final concentration of 0.1% or 1% was prepared. These solutions was incubated at 95° C. for various periods of time, an appropriate aliquot was taken to determine the enzyme activity by the method described in the above (2) to compare with that when not treated. As shown in FIG. 29, the enzyme preparation NAPS-1 obtained by the present invention had approximately 80% of the activity after the heat-treatment at 95° C. for 3 hours independently of the presence of SDS. That is, FIG. 29 is a figure showing the stability to SDS of the activated enzyme preparation NAPS-1 obtained by the present invention, and the ordinate shows the residual activity (%) and the abscissa shows time.

When the above results are compared, it is shown that the enzyme preparation NAPS-1 has remarkably decreased residual activity in comparison with the enzyme preparation NP-1. However, this phenomenon is hardly considered to be based on the difference in the stability to SDS of the enzyme proteins themselves contained in both preparations. It is thought to be the cause for the above phenomenon that NAPS-1 which is the purified enzyme preparation has less contaminant proteins as compared with NP-1 and, thereby, the inactivation easily occurs due to self-digestion.

(9) Stability to organic solvent

Figure 30:
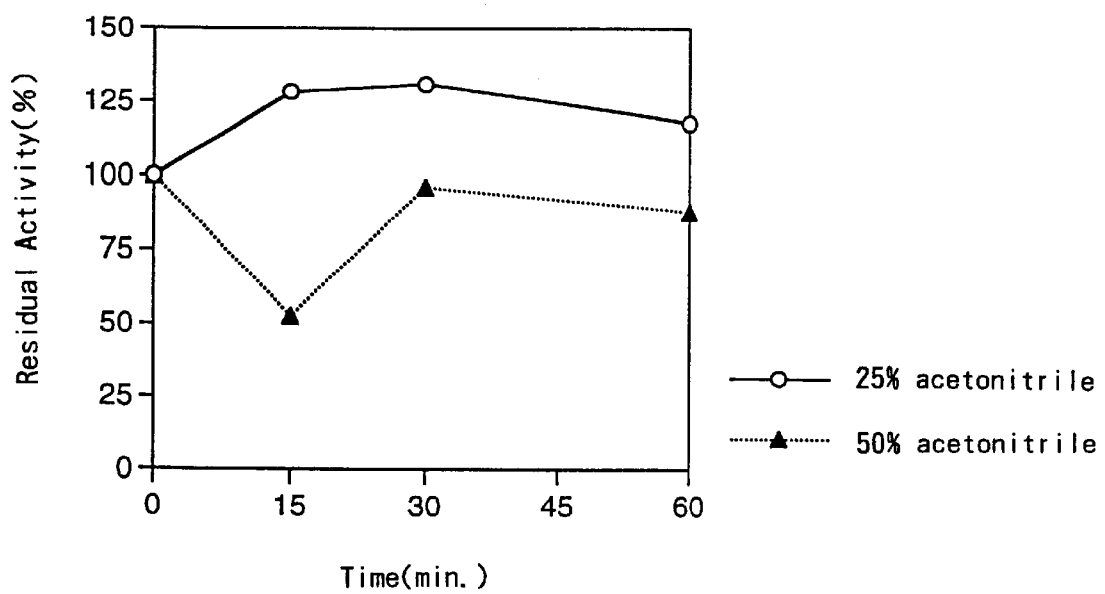
FIG. 30 is a figure showing the stability of the enzyme preparation NAPS-1 in the presence of acetonitrile.

The stability to an organic solvent of the enzyme preparation NAPS-1 obtained by the present invention was investigated using acetonitrile. Each 50 μl of enzyme preparation NAPS-1 solutions containing acetonitrile to the final concentration of 25% or 50% was incubated at 95° C. for various periods of time, and an appropriate aliquot was taken to determine the activity by the method described in the above (2) to compare with that when not treated. As shown in FIG. 30, the enzyme preparation NAPS-1 obtained by the present invention had the activity of not less than 80% of that before the treatment, even after the treatment at 95° C. for 1 hour in the presence of 50% acetonitrile. That is, FIG. 30 is a figure showing the stability to acetonitrile of the enzyme preparation NAPS-1 obtained by the present invention.

(10) Stability to denaturing agent

Figure 31:
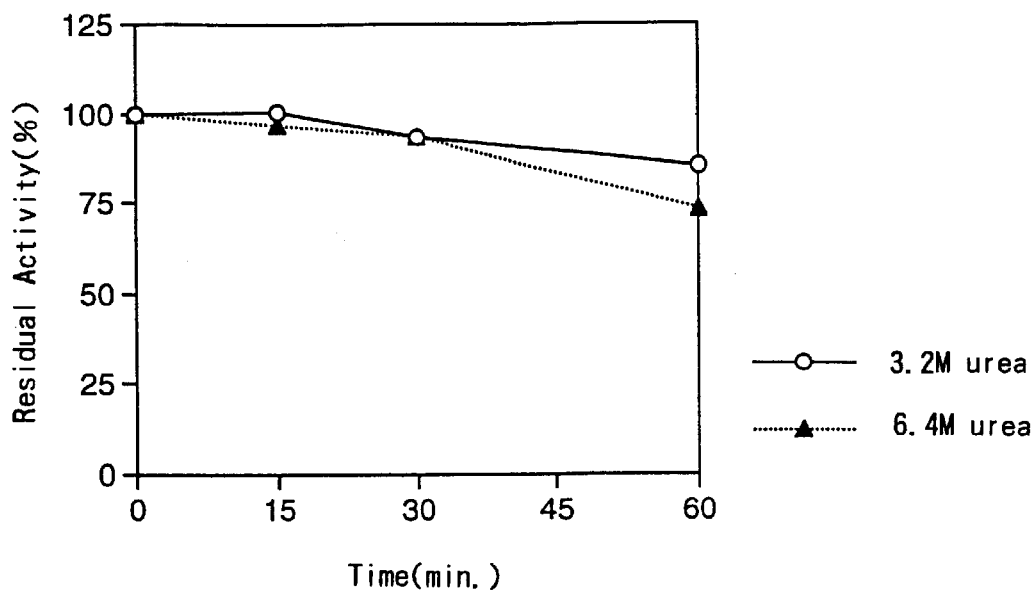
FIG. 31 is a figure showing the stability of the enzyme preparation NAPS-1 in the presence of urea.
Figure 32:
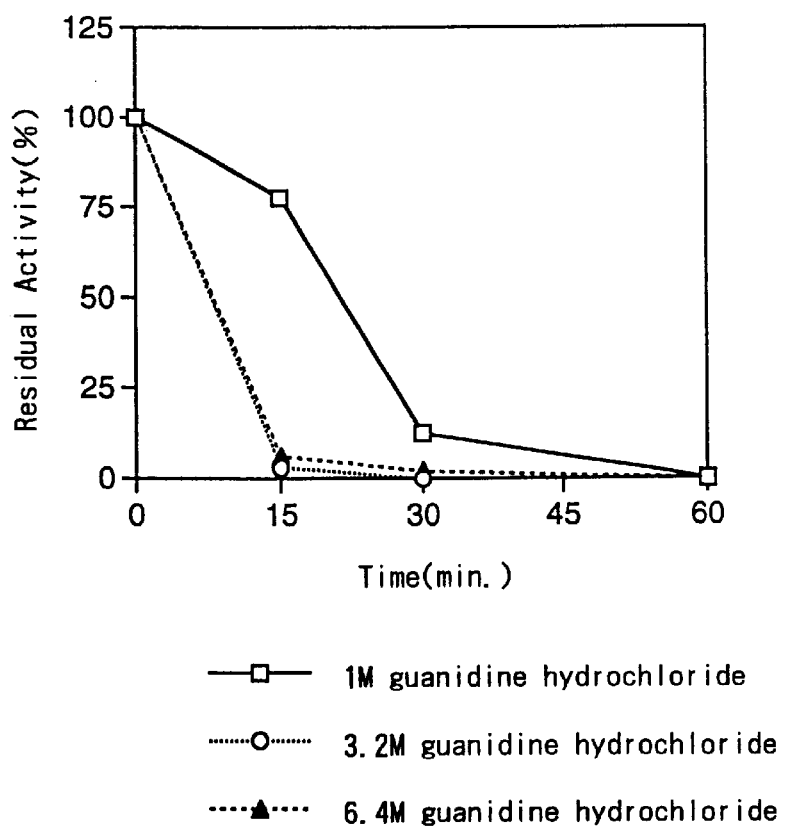
FIG. 32 is a figure showing the stability of the enzyme preparation NAPS-1 in the presence of guanidine hydrochloride.

The stability to various denaturing agents of the enzyme preparation NAPS-1 obtained by the present invention was investigated using urea and guanidine hydrochloride. Each 50 μl of the enzyme preparation NAPS-1 solution containing urea to the final concentration of 3.2 M or 6.4 M or guanidine hydrochloride to the final concentration of 1 M, 3.2 M or 6.4 M was prepared. These solutions were incubated at 95° C. for various periods of time, an appropriate aliquot was taken to determine the activity by the method described in the above (2) to compare with that when not treated. As shown FIG. 31, the enzyme preparation NAPS-1 obtained by the present invention shows the resistance to urea and had the activity of not less than 70% of that before the treatment, even after the treatment at 95° C. for 1 hour in the presence of 6.4 M urea. That is, FIG. 31 is a figure showing the stability to urea and FIG. 32 is a figure showing the stability to guanidine hydrochloride, and the ordinate indicates the residual activity and the abscissa indicates time.

(11) Effects of various reagents

The effects of various reagents on the enzyme preparations TCES and NAPS-1 obtained by the present invention were investigated. That is, the above enzyme preparations were treated at 37° C. for 30 minutes in the presence of the various reagents at the final concentration of 1 mM, and an aliquot thereof was taken to determine the enzyme activity by the method described in the above (2) to compare with that (control) when no reagent was added. The results are shown in Table 1.

TABLE 1

| Reagent | TCES | NAPS-1 |
| --- | --- | --- |
| Control | 100% | 100% |
| EDTA | 103.5% | 36.1% |
| PMSF | 8.1% | 0.1% |
| Antipain | 19.0% | 81.9% |
| Chymostatin | 0% | 6.6% |
| Leupeptin | 104.5% | 89.3% |
| Pepstatin | 105.2% | 100.7% |
| N-ethylmaleimide | 82.6% | 102.6% |

As shown in Table 1, when treated with PMSF (phenylmethanesulfonyl fluoride) and chymostatin, both enzyme preparations had the remarkably decreased activity. In addition, when treated with antipain, the decrease in the activity was observed in TCES, and when treated with EDTA, in NAPS-1, respectively. In a case of other reagents, the large decrease was not observed in the activity.

(12) Molecular weight

A molecular weight of the enzyme preparation NAPS-1 obtained by the present invention was determined by SDS-PAGE using 0.1% SDS-10% polyacrylamide gel. The enzyme preparation NAPS-1 showed a molecular weight of about 45 kDa on SDS-PAGE. On the other hand, the enzyme preparation NAPS-1S showed the same molecular weight as that of the enzyme preparation NAPS-1.

(13) N-terminal amino acid sequence

The N-terminal amino acid sequence of a mature enzyme, the protease PFUS, was determined using the enzyme preparation NAPS-1 obtained by the present invention. The enzyme preparation NAPS-1 electrophoresed on 0.1% SDS-10% polyacrylamide gel was transferred onto the PVDF membrane, and the N-terminal amino acid sequence of the enzyme on the membrane was determined by the automated Edman degradation using a protein sequencer. The N-terminal amino acid sequence of the mature type protease PFUS thus determined is shown in SEQ ID No. 42 of the Sequence Listing. The sequence coincided with the sequence of amino acids 133 to 144 in the amino acid sequence of the protease PFUS represented by SEQ ID No. 35 of the Sequence Listing, and it was shown that the mature protease PFUS is an enzyme consisting of the polypeptides including behind this part. The amino acid sequence of the mature protease PFUS thus revealed is represented by SEQ ID No. 3 of the Sequence Listing. In addition, as described above, there is no influence on the enzyme activity of the protease PFUS independently of whether 428th amino acid (corresponding to 560th amino acid in the amino acid sequence represented by SEQ ID No. 35 of the Sequence Listing) is glycine or valine. Further, within the nucleotide sequence of the protease PUFS gene represented by SEQ ID No. 34 of the Sequence Listing, that of a region encoding the mature type enzyme is shown in SEQ ID No. 4. 1283rd base in the sequence may be guanine or thymine.

In a case of in vitro gene amplification by PCR, the misincorporation of a nucleotide may occur during the elongation reaction, leading to the nucleotide substitution in the sequence of the resulting DNA. This frequency largely depends upon the kind of the enzyme used for PCR, the composition of the reaction mixture, the reaction conditions, the nucleotide sequence of a DNA to be amplified and the like. However, when a certain region in a gene is simply amplified as performed usually, the frequency is at best around one nucleotide per 400 nucleotides. In the present invention, PCR was used for isolation of a gene of the protease TCES or the protease PFUS or construction of the expression plasmid therefor. The number of nucleotide substitutions in the nucleotide sequence of the resulting gene is, if any, a few nucleotides. Taking into consideration the fact that the nucleotide substitution on a gene dose not necessarily lead to the amino acid substitution in the expressed protein due to degeneracy of translation codons, the number of the possible amino acid substitutions can be evaluated to be at best 2 to 3 in the whole residues. It cannot be denied that the nucleotide sequence of a gene of the protease TCES and the protease PFUS and the amino acid sequence of the proteases disclosed herein are different from natural ones. However, the object of the present invention is to disclose a hyperthermostable protease having the high activity at high temperature and a gene encoding the same and, therefore, the protease and the gene are not limited to the same enzyme and the same gene encoding the same as the natural ones. And it is clear to those skilled in the art that even a gene having the possible nucleotide substitution can hybridize to a natural gene under the stringent conditions.

Further, in the specification, a method for obtaining a gene of interest is clearly disclosed such that (1) the library for expression cloning is made from a chromosomal DNA of the hyperthermophiles and the expression of the protease activity is screened, (2) a gene possibly expressing the hyperthermostable protease is isolated by hybridization or PCR based on the homology of amino acid sequences, and the enzyme action of expression products of these genes, that is, the hyperthermostable protease activity is confirmed using an appropriate microorganism. Therefore, it can be easily determined by using the above method whether the gene sequence with the mutation introduced encodes a hyperthermostable protease, after a variety of mutations are introduced into the hyperthermostable protease gene of the present invention using the known mutation introducing method. The kind of the mutation to be introduced is tot limited to specified ones as long as the gene sequence obtained as a result of the mutation introduction expresses substantially the same protease activity as that of the hyperthermostable protease of the present invention. However, in order that the expressed protein retains the protease activity, the mutation is desirably introduced into a region other than four regions which are conserved in common in the serine proteases.

A mutation can be randomly introduced into any region of a gene encoding the hyperthermostable protease (random mutagenesis), or alternatively, a desired mutation can be introduced into a specified pre-determined position (site-directed mutagenesis). As a method for randomly introducing a mutation, for example, there is a method for chemically treating a DNA. In this case, a plasmid is prepared such that a region into which a mutation is sought to be introduced is partially single-stranded, and sodium bisulfite is acted on this partially single-stranded region to convert a base cytosine into uracil and, thus, introducing a transition mutation from C:G to T:A. In addition, a method for producing a base substitution during a process where a single-stranded part is repaired to double-strand in the presence of [α-S] dNTP is also known. The details of these methods are described in Proc. Natl. Acad. Sci. USA, volume 79, page 1408–1412 (1982), and Gene, volume 64, page 313–319 (1988).

Random mutation can also be introduced by conducting PCR under the conditions where fidelity of the nucleotide incorporation becomes lower. In particular, the addition of manganese to the reaction system is effective and the details of this method are described in Anal. Biochem., volume 224, page 347–355 (1995). As a method for introducing a site-directed mutation, for example, there is a method using a system where a gene of interest is made single-stranded, a primer designed depending upon a mutation sought to be introduced in this single-stranded part is synthesized, and the primer is annealed to the part, which is introduced into in vivo system where only the strand with a mutation introduced is selectively replicated. The details of this method are described in Methods in Enzymology, volume 154, page 367 (1987). For example, a mutation introducing kit, Mutant K manufactured by Takara Shuzo Co., Ltd. can be used. Site-directed mutagenesis can be conducted also by PCR and the details are described of the method in PCR Technology, page 61–70 (1989), edited by Ehlich and published by Takara Shuzo Co., Ltd. Alternatively, for example, LA-PCR in vitro mutagenesis kit manufactured by Takara Shuzo Co., Ltd. can be used. By using the above method, a mutation of substitution, deletion and insertion can be introduced.

Thus, an enzyme having the similar thermostability and optimum temperature to those of the hyperthermostable protease of the present invention but having a little different, for example, optimum pH can be produced in a host by introducing a mutation using as a base the hyperthermostable protease gene of the present invention. In this case, the base nucleotide sequence of the hyperthermostable protease gene is not necessarily limited to the sequence derived from one hyperthermostable protease.

A hybrid gene can be made by recombinating two or more hyperthermostable protease genes having a sequence homologous to each other, such as those disclosed by the present invention, by exchanging the homologous sequence, and the hybrid enzyme encoded by the gene can be produced in a host. Also in a case of a hybrid gene, whether it is a hyperthermostable protease gene can be determined by testing for the enzyme action of the gene product, that is, the protease activity. For example, by using the above plasmid pSPT1, a hybrid protease of which N-terminal part is derived from the protease PFUS and of which C-terminal part is derived from the protease TCES can be produced in Bacillus subtilis, and this hybrid protease has the protease activity at 95° C.

The hybrid enzyme is expected to have the properties of two or more base enzymes at the same time. For example, when the protease TCES and the protease PFUS disclosed herein are compared, the protease TCES is superior in respect of the extracellular secretion efficiency and the protease PFUS is superior in respect of the thermostability. Since a signal sequence located at a N-terminal of the proteins has the great influence on extracellular secretion efficiency, if an expression plasmid is constructed so that a protein having, in contrast with pSPT1, a N-terminal part derived from the protease TCES and a C-terminal part derived from the protease PFUS is produced, a hyperthermostable protease having the equal thermostability to that of the protease PFUS can be secreted at the equal secretional efficiency to that of the protease TCES. In addition, since a signal sequence is cut from an enzyme when the enzyme is extracellularly secreted, it has little influence on the nature of the enzyme itself. Therefore, when a hyperthermostable protease is produced using a mesophile, its signal sequence dose not necessarily need to be derived from hyperthermophiles and a signal sequence derived from a mesophile has no problem as long as a protein of interest is extracellularly secreted at a higher efficiency.

In particular, when a signal sequence of a secretory protein which is highly expressed in a host to be used is employed, a higher secretion is expected.

Upon construction of the above hybrid gene, a recombination dose not necessarily need to be conducted site-directedly. Alternatively, a hybrid gene can be made, for example, by mixing two or more DNAs of a hyperthermostable protease gene, which are raw materials for construction of the hybrid gene, fragmenting these with a DNA degrading enzyme and reconstituting these fragments using a DNA polymerase. The details of this method are described in Proc. Natl. Acad. Sci. USA, volume 91, page 10747–10751 (1994). Also in this case, a sequence of a gene encoding a hyperthermostable gene can be isolated and identified from the resulting hybrid genes by examining the hyperthermostable protease activity of expressed proteins as described above. In addition, it is expected that sequences encoding four regions common to the serine proteases are conserved in the sequences of the genes thus obtained.

Therefore, it is clear to those skilled in the art that the resulting hybrid gene can hybridize to a DNA selected from the oligonucleotides PRO-1F, PRO-2F, PRO-2R and PRO-4R having the nucleotide sequences represented by SEQ ID Nos. 9, 10, 11 and 12 of the Sequence Listing by the appropriate hybridization conditions. In addition, it is also clear that a novel hyperthermostable protease gene obtained by the above mutation introduction can hybridize to a gene having a DNA sequence selected from nucleotide sequences represented by SEQ ID Nos. 9, 10, 11 and 12 of the Sequence Listing, for example, the protease PFUL gene by the appropriate hybridization conditions.

In the specification, we described by focusing on obtaining of a hyperthermostable gene. However, a gene encoding a novel protease having both high thermostability and other properties can be made by constructing a hybrid gene of the hyperthermostable protease gene of the present invention and a protease gene having a sequence homology with the hyperthermostable protease gene of the present invention but having no thermostability, for example, by constructing a hybrid gene with a gene of subtilisin to improve the thermostability of subtilisin, to obtain a gene encoding a protease having the properties originally retained by subtilisin and the higher thermostability.

In the present invention, we used Escherichia coli and Bacillus subtilis as a host into which a gene is introduced in order to detect the protease activity retained by a protein encoded by a gene and produce an enzyme preparation. However, hosts into which a gene is introduced are not limited to specified ones. Any hosts can be used as long as a transforming method is established for the hosts, such as Bacillus brevis, Lactobacillus, yeast, mold fungi, animal cells, plant cells, insect cells and the like. Upon this, it is important that a polypeptide is folded such that an expressed protein becomes an active form and this does not result in the harmful or lethal effect. Among hosts listed above, Bacillus brevis, Lactobacillus and mold fungi which are known to secret their products in a medium can be used as a host for mass production of a protease of interest on an industrial scale, in addition to Bacillus subtilis.

EXAMPLES

The following Examples further describe the present invention in detail but are not limit the scope thereof.

Example 1

(1) Preparation of oligonucleotide for detection of hyperthermostable protease gene By comparing the amino sequence of the protease PFUL represented by SEQ ID No. 8 of the Sequence Listing with those of alkaline serine proteases derived from the known bacterium, the homologous amino acid sequences common to them proved to exist. Among them, three regions were selected and the oligonucleotides were designed, which were used as primers for PCR to detect hyperthermostable protease genes.

FIGS. 2, 3 and 4 show the relationship among the amino acid sequences corresponding to the above three regions of the protease PFUL, the nucleotide sequences of the protease PFUL gene encoding the regions, and the nucleotide sequences of the oligonucleotides PRO-1F, PRO-2F, PRO-2R and PRO-4R synthesized based thereon. SEQ ID Nos. 9, 10, 11 and 12 show the nucleotide sequences of the oligonucleotides PRO-1F, PRO-2F, PRO-2R and PRO-4R, respectively.

(2) Preparation of chromosomal DNA of *Thermococcus celer*

10 ml of a culture of *Thermococcus celer* DSM2476 obtained from Deutsche Sammlung von Mikroorganismen und Zellkulturen GmbH was centrifuged to collect the cells which were suspended in 100 μl of 50 mM Tris-HCl, pH 8.0 containing 25% sucrose. To this suspension was added 20 μl of 0.5 M EDTA and 10 μl of 10 mg/ml lysozyme, and was incubated at 20° C. for 1 hour, 800 μl of a SET solution (150 mM NaCl, 1mM EDTA, 20mM Tris-HCl, pH 8.0), 50 μl of 10% SDS and 10 μl of 20 mg/ml proteinase K were added thereto, and was incubated at 37° C. for 1 hour. The reaction was stopped by extraction with phenol-chloroform and precipitated with ethanol to recover a DNA which was dissolved in 50 μl of a TE buffer (10 mM Tris-HCl, pH 8.0, 0.1 mM EDTA) to give a chromosomal DNA solution.

(3) Detection of hyperthermostable protease gene by PCR

A PCR reaction mixture was prepared from the above chromosomal DNA of *Thermococcus celer* and the oligonucleotides PRO-1F and PRO-2R, or PRO-2F and PRO-4R, and a 35 cycles reaction was carried out, each cycle consisting of 94° C. for 1 minute–55° C. for 1 minute–72° C. for 1 minute. When an aliquot of these reaction mixture were subjected to agarose gel electrophoresis, amplification of three DNA fragments in case of the using the oligonucleotides PRO-1F and PRO-2R, and one DNA fragments in case of the using the oligonucleotides PRO-2F and PRO-4R were observed. These amplified fragments were recovered from the agarose gel, and the DNA ends thereof were made blunt using a DNA blunting kit (manufactured by Takara Shuzo Co., Ltd.) and phosphorylated using the T4 polynucleotide kinase (manufactured by Takara Shuzo Co., Ltd.). Then, the plasmid vector pUC19 (manufactured by Takara Shuzo Co., Ltd.) was digested with HincII (manufactured by Takara Shuzo Co., Ltd.), the resulting fragments were dephosphorylated at ends thereof by alkaline phosphatase (manufactured by Takara Shuzo Co. Ltd.), mixed with the above PCR-amplified DNA fragments to allow to ligate, followed by introduction into *Escherichia coli* JM109. Plasmids were prepared from the resulting transformant, and the plasmids with an appropriate size DNA fragment inserted were selected, followed by sequencing of the inserted fragment by the dideoxy method.

Of these plasmids, the amino acid sequence deduced from the nucleotide sequence of the plasmid p1F-2R(2) containing an about 150 bp DNA fragment amplified using the oligonucleotides PRO-1F and PRO-2R, and that deduced from the nucleotide sequence of the plasmid p2F-4R containing an about 550 bp DNA fragment amplified using oligonucleotides PRO-2F and PRO-4R contained sequences having the homology with the amino acid sequences of the protease PFUL, subtilisin and the like. SEQ ID No. 13 of the Sequence Listing shows the nucleotide sequence of the inserted DNA fragment in the plasmid p1F-2R(2) and the amino acid sequence deduced therefrom and SEQ ID NO. 14 of the Sequence Listing shows the nucleotide sequence of the inserted DNA fragment in the plasmid p2F-4R and the amino acid sequence deduced therefrom. In the nucleotide sequence represented by SEQ ID No. 13 of the Sequence Listing, the sequence of 1st to 21st nucleotides and that of 113rd to 145th nucleotides and, in the nucleotide sequence represented by SEQ ID No. 14 of the Sequence Listing, the sequence of 1st to 32nd nucleotides and that of 532nd to 564th nucleotides are the sequences of the oligonucleotides (corresponding to oligonucleotides PRO-1F, PRO-2R, PRO-2F and PRO-4R, respectively) used as primers for PCR.

FIG. 5 shows a figure of a restriction map of the plasmid p2F-4R.

(4) Screening of protease gene derived from *Thermococcus celer*

The chromosomal DNA of *Thermococcus celer* was partially digested with the restriction enzyme Sau3AI (manufactured by Takara Shuzo Co., Ltd.), followed by partial repair of the DNA ends using Klenow Fragment (manufactured by Takara Shuzo Co., Ltd.) in the presence of DATP and dGTP. The DNA fragments were mixed with the lambda GEM-11 XhoI Half-Site Arms Vector (manufactured by Promega) to allow to ligate, which was subjected in vitro packaging using Gigapack Gold (manufactured by Stratagene) to prepare a lambda phage library containing the chromosomal DNA fragments of *Thermococcus celer*. A part of the library was transformed into *Escherichia coli* LE392 (manufactured by Promega) to form the plaques on a plate, and the plaques were transferred to Hybond-N+ membrane (manufactured by Amersham). After transference, the membrane was treated with 0.5N NaOH containing 1.5M NaCl, then with 0.5M Tris-HC1, pH 7.5 containing 3M NaCl, washed with 6×SSC, air dried, and irradiated with ultraviolet rays on the UV transilluminator to fix the phage DNA to the membrane.

On the other hand, the plasmid p2F-4R was digested with PmaCI and StuI (both manufactured by Takara Shuzo Co., Ltd.), which was subjected to 1% agarose gel electrophoresis to recover the separated about 0.5 kb DNA fragment. By using this fragment as a template and using Random Primer DNA Labeling Kit Ver.2 (manufactured by Takara Shuzo Co., Ltd.) and [α-$^{32}$P]dCTP (manufactured by Amersham), a ⁻P-labeled DNA probe was prepared.

The membrane with the DNA fixed thereto was treated with a hybridization buffer (6×SSC containing 0.5% SDS, 0.1% SBA, 0.1% polyvinylpyrrolidone, 0.1% Ficoll 400, 0.01% denatured salmon sperm DNA) at 50° C. for 2 hours, and transferred to the same buffer containing the $^{32}$P-labeled DNA probe, followed by hybridization at 50° C. for 15 hours. After the completion of hybridization, the membrane was washed with 2×SSC containing 0.5% SDS at room temperature, then with 1×SSC containing 0.5% SDS at 50° C. The membrane was further rinsed with 1×SSC, air dried and a X-ray film was exposed thereto at −80° C. for 6 hours to obtain an autoradiogram. About 3,000 phage clones were screened and, as a result, one clone containing a protease gene was obtained. Based on the signal on the autoradiogram, the position of this phage clone was found and the plaque corresponding on the plate used for transfer to the membrane was isolated into 1 ml of a SM buffer (50 mM Tris-HCl, pH 7.5, 1M NaCl, 8 mM MgSO4, 0.01% gelatin) containing 1% chloroform.

(5) Detection of phage DNA fragment containing protease gene derived from *Thermococcus celer*

Transduced *Escherichia coli* LE392 using the above phage clone was cultured in the NZCMY medium (manufactured by Bio101) at 37° C. for 15 hours to obtain a culture, from which a supernatant was collected to prepare a phage DNA using QIAGEN-lambda kit (manufactured by QIAGEN). The resulting phage DNAs were digested with BamHI, EcoRI, EcoRV, HincII, KpnI, NcoI, PstI, SacI, SalI, SmaI and SphI (all manufactured by Takara Shuzo Co., Ltd.), respectively, followed by agarose gel electrophoresis. Then, DNAs were transferred from the gel to Hybond-N+ membrane according to the southern transfer method described in Molecular Cloning; A Laboratory Manual, 2nd edition (1986), edited by T. Maniatis, et al., published by Cold Spring Harbor Laboratory.

The resulting membrane was treated in a hybridization buffer at 50° C. for 4 hours, and transferred to the same buffer containing the $^{32}$P-labeled DNA probe used in Example 1-(4), followed by hybridization at 50° C. for 18 hours. After the completion of hybridization, the membrane was washed in 1×SSC containing 0.5% SDS at 50° C., then rinsed with 1×SSC and air dried. The membrane was exposed to a X-ray film at –80° C. for 6 hours to obtain an autoradiogram. This autoradiogram indicated that an about 9 kb DNA fragment contained a protease gene in case of the phage DNA digested with KpnI.

Then, the phage DNA containing the above protease gene was digested with KpnI, and further digested successively with BamHI, PstI and SphI, followed by 1% agarose gel electrophoresis. According to the similar procedures to those described above, southern hybridization was conducted and it was indicated that an about 5 kb KpnI-BamHI fragment contained a protease gene.

(6) Cloning of DNA fragment containing protease gene derived from *Thermococcus celer*

The phage DNA containing the above protease gene was digested with KpnI and BamHI, which was subjected to 1% agarose gel electrophoresis to separate and isolate an about 5 kb DNA fragment from the gel. Then, the plasmid vector pUC119 (manufactured by Takara Shuzo Co., Ltd.) was digested with KpnI and BamHI, which was mixed with the above about 5 kb DNA fragment to allow to ligate, followed by introduction into *Escherichia coli* JM109. Plasmids were prepared form the resulting transformant, the plasmid containing the about 5 kb DNA fragment was selected and designated the plasmid pTC3.

FIG. 6 shows a restriction map of the plasmid pTC3.

(7) Preparation of plasmid pTCS6 containing protease gene derived from *Thermococcus celer*

The above plasmid pTC3 was digested with SacI, which was electrophoresed using 1% agarose gel, and southern hybridization was carried out according to the same manner as that described in Example 1-(5) for detecting the phage DNA fragment containing a protease gene. A signal on the resulting autoradiogram indicated that an about 1.9 kb DNA fragment obtained by digesting the plasmid pTC3 with SacI contained a hyperthermostable protease gene.

Then, the plasmid pTC3 was digested with SacI, which was subjected to 1% agarose gel electrophoresis to isolate an about 1.9 kb DNA fragment. Then, the plasmid vector pUC118 (manufactured by Takara Shuzo Co., Ltd.) was digested with SacI, which was dephosphorylated using alkaline phosphatase and mixed with the about 1.9 kb fragment to allow to ligate, followed by introduction into *Escherichia coli* JM109. Plasmids were prepared from the resulting transformant, and the plasmid containing only one molecule of the about 1.9 kb fragment was selected and designated the plasmid pTCS6.

FIG. 7 shows a restriction map of the plasmid pTCS6.

(8) Determination of nucleotide sequence of DNA fragment derived from *Thermococcus celer* contained in plasmid pTCS6

In order to determine the nucleotide sequence of the protease gene derived from *Thermococcus celer* inserted into the plasmid pTCS6, the deletion mutants wherein the DNA fragment portion inserted into the plasmid had been deleted in various length were prepared using Kilo Sequence Deletion Kit (manufactured by Takara Shuzo Co., Ltd.). Among them, several mutants having suitable length of deletion were selected and the nucleotide sequence of each of the inserted DNA fragment parts was determined by the dideoxy method, and these results were combined to determine the nucleotide sequence of the inserted DNA fragment contained in the plasmid pTCS6. SEQ ID No. 15 of the Sequence Listing shows the resulting nucleotide sequence.

(9) Cloning of 5' upstream region of a protease gene derived from *Thermococcus celer* by PCR using cassette and cassette primer A 5' upstream region of the protease gene derived from *Thermococcus celer* was obtained by using LA PCR in vitro cloning kit (manufactured by Takara Shuzo Co., Ltd.).

Based on the nucleotide sequence of the inserted DNA fragment contained in the plasmid pTCS6 represented by SEQ ID No. 15 of the Sequence Listing, the primer TCE6R for use in cassette PCR was synthesized. SEQ ID No. 16 of the Sequence Listing shows the nucleotide sequence of the primer TCE6R.

Then, a chromosomal DNA of *Thermococcus celer* was completely digested with HindIII (manufactured by Takara Shuzo Co., Ltd.), and the fragments were ligated to the HindIII cassette (manufactured by Takara Shuzo Co., Ltd.) by the ligation reaction. By using this as a template, a PCR reaction mixture containing the primer TCE6R and the cassette primer C1 (manufactured by Takara Shuzo Co., Ltd.) was prepared, a series of reactions, one cycle of 94° C. for one minute, 30 cycles of 94° C. for 30 seconds-55° C. for 1 minute-72° C. for 3 minutes, and one cycle of 72° C. for 10 minutes were carried out. An aliquot of this reaction mixture was subjected to agarose gel electrophoresis and an amplified about 1.8 kb fragment was observed. This amplified fragment was digested with HindIII and SacI, and the about 1.5 kb DNA fragment produced was recovered from the gel after agarose gel electrophoresis. The HindIII-SacI digested plasmid vector pUC119 was mixed with the above about 1.5 kb DNA fragment to allow to ligate, followed by introduction into *Escherichia coli* JM109. The plasmid harboured by the resulting transformant was examined, the plasmid with only one molecule of the 1.5 kb fragment inserted was selected and designated the plasmid pTC4.

FIG. 8 shows a restriction map of the plasmid pTC4.

(10) Determination of nucleotide sequence of DNA fragment derived from *Thermococcus celer* contained in plasmid pTC4 and protease TCES gene In order to determine the nucleotide sequence of a protease gene derived from *Thermococcus celer* inserted into the plasmid pTC4, the deletion mutants wherein the DNA fragment portion inserted into the plasmid had been deleted in various length were prepared using Kilo Sequence Deletion Kit. Among them, several mutants having suitable length of deletion were selected and the nucleotide sequence of each of the inserted DNA fragment parts was determined by the dideoxy method, and these results were combined to determine the nucleotide sequence of the inserted DNA fragment contained in the plasmid pTCS4. SEQ ID No. 15 of the Sequence Listing shows the resulting nucleotide sequence.

By combining the sequence with the nucleotide sequence of the inserted DNA fragment contained in the plasmid pTCS6 obtained in Example 1-(8), the whole nucleotide sequence of the protease gene derived from *Thermococcus celer* was determined. SEQ ID No. 1 and 2 of the Sequence Listing show the nucleotide sequence of open reading frame present in the nucleotide sequence and the amino acid sequence deduced therefrom of the protease derived from *Thermococcus celer*, respectively. The protease derived from *Thermococcus celer* encoded by the gene was designated the protease TCES.

(11) Preparation of plasmid pBTC6 containing protease TCES gene

The plasmid pTCS6 was digested with HindIII and SspI (manufactured by Takara Shuzo Co., Ltd.), which was subjected to 1% agarose gel electrophoresis to recover the separated about 1.8 kb DNA fragment. Then, the plasmid vector pBT322 (manufactured by Takara Shuzo Co., Ltd.) was digested with HindIII and EcoRV, which was mixed with the about 1.8 kb DNA fragment to allow to ligate, followed by introduction into *Escherichia coli* JM109. Plasmids were prepared from the resulting transformant, the plasmid containing only one molecule of the 1.8 kb fragment was selected and designated the plasmid pBTC5.

Then, the plasmid pBTC5 was completely digested with HindIII and KpnI, which was blunt-ended and was subjected to intramolecular ligation, followed by introduction into *Escherichia coli* JM109. Plasmids were prepared from the resulting transformant, and the plasmid from which the above two restriction enzyme sites had been removed was selected and designated the plasmid pBTC5HK.

Further, the plasmid pBTC5HK was digested with BamHI, which was blunt-ended, and was subjected to intramolecular ligation, followed by introduction into *Escherichia coli* JM109. Plasmids were prepared from the resulting transformant, the plasmid from which the BamHI site had been removed was selected and designated the plasmid pBTC5HKB.

The primer TCE12 which can introduce the EcoRI site and the BamHI site in front of an initiation codon on the protease TCES gene, and the primer TCE20R which has 16 bp-long nucleotide sequence complementary to a 3' part of the SacI site of the plasmid pTCS6 and can introduce the ClaI site and a termination codon were synthesized. SEQ ID Nos. 18 and 19 of the Sequence Listing show the nucleotide sequences of the primer TCE12 and the primer TCE20R, respectively. A PCR reaction mixture was prepared using these two primers and using a chromosomal DNA of *Thermococcus celer* as a template. A reaction of 25 cycles, each cycle consisting of 94° C. for 30 seconds-55° C. for 1 minute-72° C. for 1 minute, was carried out to amplify an about 0.9 kb DNA fragment having these two oligonucleotides on both ends and containing a part of the protease TCES gene.

The above about 0.9 kb DNA fragment was digested with EcoRI and ClaI (manufactured by Takara Shuzo Co., Ltd.), which was mixed with the EcoRI-ClaI digested plasmid pBTC5HKB to allow to ligate, followed by introduction into *Escherichia coli* JM109. Plasmids were prepared from the resulting transformant, and the plasmid containing only one molecule of the about 0.9 kb fragment was selected and designated the plasmid pBTC6.

(12) Preparation of plasmid pTC12 containing protease TCES gene

The plasmid pBTC6 was digested with BamHI and SphI, which was subjected to 1% agarose gel electrophoresis to recover the separated about 3 kb DNA fragment. Then, the plasmid pUC-P43SD where the ribosome binding site sequence derived from *Bacillus subtilis* P43 promoter was introduced between the KpnI site and the BamHI site of the plasmid vector pUC18 (manufactured by Takara Shuzo Co., Ltd.) (the nucleotide sequence of the synthetic oligonucleotides BS1 and BS2 used for introduction of the sequence are shown in SEQ ID Nos. 20 and 21 of the Sequence Listing) was digested with BamHI and SphI, which was mixed with the previously recovered about 3 kb DNA fragment to allow to ligate, followed by introduction into *Escherichia coli* JM109. Plasmids were prepared from the resulting transformant, the plasmid containing only one molecule of the above about 3 kb DNA fragment was selected and designated the plasmid pTC12.

(13) Preparation of plasmid pSTC3 containing protease TCES gene for transforming *Bacillus subtilis*

The above plasmid pTC12 was digested with KpnI and SphI, which was-subjected to 1% agarose electrophoresis to recover the separated about 3 kb DNA fragment. Then, the plasmid vector pUB18-P43 was digested with SacI, which was bunt-ended and allowed to self-ligate to give the plasmid vector pUB18-P43S from which the SacI site had been removed. This was digested with KpnI and SphI, which was mixed with the previously recovered about 3kb DNA fragment and allowed to ligate, followed by introduction into *Bacillus subtilis* DB104. Plasmids were prepared from the resulting kanamycin-resistant transformant, and the plasmid containing only one molecule of the above about 3 kb DNA fragment was selected and designated the plasmid pSTC2.

Then, the plasmid pSTC2 was digested with SacI and was subjected to intramolecular ligation, followed by introduction into *Bacillus subtilis* DB104. Plasmids were prepared from the resulting kanamycin-resistant transformant, the plasmid containing only one SacI site and designated the plasmid pSTC3.

Then, *Bacillus subtilis* DB104 harbouring the plasmid pSTC3 was designated *Bacillus subtilis* DB104/pSTC3.

FIG. 10 shows a restriction map of the plasmid pSTC3.

Example 2

(1) Preparation of chromosomal DNA of *Pyrococcus furiosus*

*Pyrococcus furiosus* DMS3638 was cultured as follows. A medium having the composition of 1% trypton, 0.5% yeast extract, 1% soluble starch, 3.5% Jamarin SÅSolid (manufactured by Jamarin Laboratory), 0.5% Jamarin SÅLiquid (manufactured by Jamarin Laboratory), 0.003% $MgSO_4$, 0.001% NaCl, 0.0001% $FeSO_4$ Å7 $H_2O$, 0.0001% $COSO_4$, 0.0001% $CaCl_2$ Å7 $H_2O$, 0.0001% $ZnSO_4$, 0.1 ppm $CuSO_4$ Å5 $H_2O$, 0.1 ppm $H_3BO_3$, 0.1 ppm $KAl(SO4)2$, 0.1 ppm $Na_2MoO_4$ Å2 $H_2O$, 0.25 ppm $NiCl_2$ ÅH$_2$O was placed in a 2 liter medium bottle, and was sterilized at 120° C. for 20 minutes, nitrogen gas was blown into the medium to purge out the dissolved oxygen, and the above bacterial strain was inoculated into the medium, followed by subjecting to stationarily culture at 95° C. for 16 hours. After the completion of cultivation, the cells were collected by centrifugation.

Then, the resulting cells were suspended in 4 ml of 50 mM Tris-HCl (pH 8.0) containing 25% sucrose, to this suspension was added 2 ml of 0.2 M EDTA and 0.8 ml of lysozyme (5 mg/ml) and incubated at 20° C. for 1 hour, 24 ml of a SET solution (150 mM NaCl, 1 mM EDTA, 20 mM Tris-HCl, pH 8.0), 4 ml of 5% SDS and 400 μl of proteinase K (10 mg/ml) were added thereto and incubated at 37° C. for another 1 hour. The reaction was stopped by extraction with phenol-chloroform, followed by ethanol precipitation to obtain about 3.2 mg of the chromosomal DNA.

(2) Genomic southern hybridization of *Pyrococcus furiosus* chromosomal DNA

A chromosomal DNA of *Pyrococcus furiosus* was digested with SacI, NotI, XbaI, EcoRI and XhoI (all manufactured by Takara Shuzo Co., Ltd.), respectively. An aliquot of the reaction mixture was further digested with SacI and EcoRI, which was subjected to 1% agarose gel electrophoresis, followed by southern hybridization according to the procedures described in Example 1-(5). A $^{32}$P-labeled DNA, which was prepared using an about 0.3 kb DNA fragment obtained by digesting the above plasmid p1F-2R(2) with EcoRI and PstI as a template and using BcaBEST DNA Labeling kit (manufacture by Takara Shuzo Co., Ltd.) and [α-$^{32}$P]dCTP, was used as a probe. A membrane was washed in 2×SSC containing SDS to the final concentration of 0.5% at room temperature, rinsed with 2×SSC and the autoradiogram was obtained. As a result, a signal was observed in two DNA fragments of about 5.4 kb and about 3.0 kb produced by digesting a *Pyrococcus furiosus* chromosomal DNA with SacI and it was indicated that a protease gene was present on respective fragments. When the SacI-digested fragment was further digested with SpeI (manufactured by Takara Shuzo Co., Ltd.), the signal of the above about 5.4 kb fragment did not show the change but the signal which had been seen in the about 3.0 kb fragment was lost, and a signal was newly observed in the about 0.6 kb fragment. Since the SpeI site is not present in the protease PFUL gene represented by SEQ ID No. 7 of the Sequence Listing, it was suggested that a signal on the about 0.6 kb fragment obtained by the digestion with SacI and SpeI was derived from a novel hyperthermostable protease (hereinafter referred to as "protease PFUS"). In addition, regarding the products from digestion of *Pyrococcus furiosus* chromosomal DNA with XbaI, a signal was observed on two DNA fragments of about 3.3 kb and about 9.0 kb. From a restriction map of protease PFUL gene shown in FIG. 1, it was presumed that the about 3.3 kb fragment contained the protease PFUL gene and the about 9.0 kb fragment contained the protease PFUS gene. When the above chromosomal DNA was digested with XbaI and SacI, a signal was observed on the about 2.0 kb fragment and the about 3.0 kb fragment. From the positions of the SacI and XbaI cleavage sites present on the protease PFUL gene shown in SEQ ID No. 7 of the Sequence Listing, it was presumed that the protease PFUL gene is present on the about 2.0 kb SacI-XbaI fragment. On the other hand, it was presumed that the protease PFUS gene was present on the about 3.0 kb fragment. Combining with the results on the digestion with SacI, it was shown that no XbaI site is present on the about 3.0 kb DNA fragment obtained by the digestion with SacI alone.

(3) Cloning of 0.6 kb SpeI-SacI fragment containing protease PFUS gene

A chromosomal DNA of *Pyrococcus furiosus* was digested with SacI and SpeI, which was subjected to 1% agarose gel electrophoresis to recover the DNA fragment corresponding to about 0.6 kb from the gel. Then, the plasmid pBluescript SK(−) (manufactured by Stratagene) was digested with SacI and SpeI, which was mixed with the about 0.6 kb DNA fragment to allow to ligate, followed by introduction into *Escherichia coli* JM109 to obtain the plasmid library containing the chromosomal DNA fragments. Transformed *Escherichia coli* JM109 was seeded on a plate to form the colonies, and the produced colonies were transferred to a Hybond-N+ membrane, which was incubated at 37° C. for about 2 hours on a new LB plate. This membrane was treated with 0.5N NaOH containing 1.5M NaCl, then with 0.5M Tris-HCl (pH 7.5) containing 1.5 M NaCl, washed with 2×SSC, air dried and the plasmid DNA was fixed to the membrane by irradiating with ultraviolet rays on a UV transilluminator. This membrane was treated at 50° C. for 2 hours in a hybridization buffer, and transferred to the same buffer containing a $^{32}$P-labeled DNA probe used for southern hybridization described in Example 2-(2), to hybridize at 50° C. for 18 hours. After the completion of hybridization, the membrane was washed in 2×SSC containing 0.5% SDS at room temperature, and washed at 37° C. Further, the membrane was rinsed with 2×SSC, air dried, exposed to a X-ray film at-80° C. for 12 hours to obtain an autoradiogram. About 500 clones were screened and, as a result, 3 clones containing a protease gene were obtained. From a signal on the autoradiogram, the positions of these clones were examined and the corresponding colonies on the plate used for transfer to the membrane were isolated in LB medium.

(4) Detection of protease PFUS gene by PCR Oligonucleotides which used for detection of a hyperthermostable protease gene by PCR as a probe were designed based on the nucleotide sequences encoding two regions having the high homology with the amino acid sequences of alkaline serine proteases derived from the known microorganisms in the protease PFUL gene. Based on the amino acid sequence of the protease PFUL represented by FIGS. 2 and 3, the primers 1FP1, 1FP2, 2RP1 and 2RP2 were synthesized. SEQ ID Nos. 22, 23, 24 and 25 of the Sequence Listing show the nucleotide sequences of the oligonucleotides 1FP1, 1FP2, 2RP1 and 2RP2.

PCR reaction mixtures containing the plasmids prepared from the above three clones as well as the oligonucleotides 1FP1 and 2RP1, or 1FP1 and 2RP2, or 1FP2 and 2RP1, or 1FP2 and 2RP2 were prepared, and a 30 cycle reaction was carried out, each cycle consisting of 94° C. for 30 seconds-37° C. for 2 minutes-72 ° C. for 1 minute. It was shown that, when aliquots of these reaction mixtures were subjected to agarose gel electrophoresis, respectively, the amplification of an about 150 bp DNA fragment was observed in all the three above plasmids when used the primers 1FP2 and 2RP2, indicating that a protease gene was present on these plasmids.

One of the above three clones was selected and designated the plasmid pSS3.

(5) Determination of nucleotide sequence of protease PFUS gene contained in plasmid pSS3

The nucleotide sequence of the inserted DNA fragment in the plasmid was determined by the dideoxy method using the plasmid pSS3 as a template and using the primer M4 and the primer RV (both manufactured by Takara Shuzo Co., Ltd.). SEQ ID No. 26 of the Sequence Listing shows the resultant nucleotide sequence and the amino acid sequence which was deduced to be encoded by the nucleotide sequence. By comparing the amino acid sequence with that of the protease PFUL, the protease TCES and subtilisin, it was presumed that the DNA fragment inserted in the plasmid pSS3 encoded the amino acid sequence having the homology with these proteases.

(6) Cloning of N-terminal coding region and C-terminal coding region of protease PFUS by inverse PCR method In order to obtain genes encoding N-terminal amino acid sequence and C-terminal one of the protease PFUS, the inverse PCR was carried out. A primer used for the inverse PCR was synthesized based on the nucleotide sequence of the inserted DNA fragment in the plasmid pSS3. SEQ ID Nos. 27, 28 and 29 of the Sequence Listing show the nucleotide sequences of the primers NPF-1, NPF-2 and NPR-3.

A chromosomal DNA of *Pyrococcus furiosus* was digested with SacI and XbaI and was subjected to intramolecular ligation. PCR mixtures containing an aliquot of the ligation reaction mixture and the primers NPF-1 and NPR-3, or NPF-2 and NPR-3 were prepared and a 30 cycle reaction was carried out, each cycle consisting of 94 ° C. for 30 seconds-67° C. for 10 minutes. When an aliquot of this reaction mixture was subjected to agarose gel electrophoresis, an about 3 kb amplified fragment was observed in a case of the use of the primers NPF-2 and NPR-3. This amplified fragment was recovered from the agarose gel, and mixed with the plasmid vector pT7BlueT (manufactured by Novagen) to allow to ligate, followed by introduction into *Escherichia coli* JM109. Plasmids were prepared from the resultant transformant, the plasmid containing an about 3 kb fragment was selected and designated the plasmid pS322.

On the other hand, an about 9 kb amplified fragment was observed in a case of the use of the primers NPF-1 and NPR-3. This amplified fragment was recovered from the agarose gel, the DNA ends were made blunt using a DNA blunting kit, followed by further digestion with XbaI. This was mixed with the plasmid vector pBluescript SK(-) digested with XbaI and HincII to allow to ligate, followed by introduction into *Escherichia coli* JM109. Plasmids were prepared from the resulting transformant, the plasmid containing an about 5 kb DNA fragment was selected and designated the plasmid pSKX5.

(7) Sequencing of nucleotide sequence of protease PFUS gene contained in plasmid pS322 and pSKX5

The nucleotide sequence of a gene encoding a N-terminal region of the protease PFUS was determined by the dideoxy method using the plasmid pS322 as a template and using the primer NPR-3. SEQ ID No. 30 of the Sequence Listing shows a part of the resulting nucleotide sequence and the amino acid sequence deduced to be encoded by the nucleotide sequence.

Further, the nucleotide sequence of a region corresponding to a 3' part of the protease PFUS gene was determined by the dideoxy method using the plasmid pSKX5 as a template and using the primer RV. SEQ ID No. 31 of the Sequence Listing shows a part of the resulting nucleotide sequence.

(8) Synthesis of primer used for amplification of full length protease PFUS gene Based on the nucleotide sequence obtained in Example 2-(7), a primer used for amplification of the full length of the protease PFUS gene was designed. Based on the nucleotide sequence encoding a N-terminal part of the protease PFUS shown in SEQ ID No. 30 of the Sequence Listing, the primer NPF-4 which can introduce BamHI site in front of an initiation codon of the protease PFUS gene. SEQ ID No. 32 of the Sequence Listing shows the nucleotide sequence of the primer NPF-4. In addition, based on the nucleotide sequence in the vicinity of a 3' region of the protease PFUS shown in SEQ ID No. 31 of the Sequence Listing, the primer NPR-4 having a sequence complementary to the nucleotide sequence and a SphI site was synthesized. SEQ ID No. 33 of the Sequence Listing shows the nucleotide sequence of the primer NPR-4.

(9) Preparation of plasmid pSPT1 containing hybrid gene of protease derived from *Pyrococcus furiosus* and protease TCES, for transformation of *Bacillus subtilis*

By using a LA PCR kit (manufactured by Takara Shuzo Co., Ltd.), a PCR reaction mixture (hereinafter a PCR reaction mixture prepared by using a LA PCR kit is referred to as "LA-PCR reaction mixture") containing the primers NPF-4 and NPR-4 and a chromosomal DNA of *Pyrococcus furiosus*, and a reaction of 30 cycles, each cycle consisting of 94° C. for 20 seconds-55° C. for 1 minute-68° C. for 7 minutes, was carried out to amplify an about 6 kb DNA fragment having these two primers on both ends and containing the coding region of the protease PFUS gene.

The about 6 kb DNA fragment was digested with BamHI and SacI, which was subjected to 1% agarose gel electrophoresis to recover the separated about 0.8 kb DNA fragment. This fragment was mixed with the plasmid pSTC3 digested with BamHI and SacI to allow to ligate, followed by introduction into *Bacillus subtilis* DB104. Plasmids were prepared from the resultant kanamycin-resistant transformant, and the plasmid containing only one molecule of the above 0.8 kb fragment was selected and designated the plasmid pSPT1.

*Bacillus subtilis* DB104 harboring the plasmid pSPT1 was designated *Bacillus subtilis* DB104/pSTP1.

FIG. 14 shows a restriction map of the plasmid pSPT1.

(10) Preparation of plasmid pSNP1 containing protease PFUS gene for transformation of *Bacillus subtilis*

The about 6 kb DNA fragment amplified in Example 2-(9) was digested with SpeI and SphI, which was subjected to 1% agarose gel electrophoresis to recover the separated about 5.7 kb DNA fragment. This was mixed with the plasmid digested with SpeI and SphI to allow to ligate, followed by introduction into *Bacillus subtilis* DB104. Plasmids were prepared from the resulting kanamycin-resistant transformant, and the plasmid containing only one molecule of the 5.7 kb fragment was selected and designated the plasmid pSNP1. *Bacillus subtilis* transformed with the plasmid pSNP1 was designated as *Bacillus subtilis* DB104/pSNP1.

FIG. 15 shows a restriction map of the plasmid pSNP1.

(11) Determination of nucleotide sequence of protease PFUS gene contained in plasmid pSNP1

An about 6 kb DNA fragment containing a protease gene inserted into the plasmid pSNP1 was fragmented into appropriate size with a variety of restriction enzymes, and the fragments were subcloned into the plasmid vector pUC119 or pBluescript SK(-). The nucleotide sequence was determined by the dideoxy method using the resulting recombinant plasmid as a template and using a commercially available universal primer. Regarding a part from which the fragments having appropriate size could not be obtained, the primer walking method was used utilizing the synthetic primers. The nucleotide sequence of an open reading frame present in the nucleotide sequence of the DNA fragment inserted into the plasmid pSNP1 thus determined, and the amino acid sequence of a protease derived from *Pyrococcus furiosus* deduced from the nucleotide sequence are shown in SEQ ID Nos. 34 and 35, respectively.

(12) Synthesis of primer for amplification of protease PFUS gene

In order to design a primer, which is used for amplification of the full length protease PFUS gene and hybridizes to a 3' part of the gene, the nucleotide sequence of the 3' part of the gene was determined. First, an about 0.6 kb DNA fragment containing the 3' region of the protease PFUS gene, obtained by digestion of the plasmid pSNP1 with BamHI, was ligated with the plasmid vector pUC119 which had been digested with BamHI and dephosphorylated with alkaline phosphatase. The resulting recombinant plasmid was designated the plasmid PSNPD and the nucleotide sequence of a region corresponding to the 3' part of the protease PFUS gene was determined by the dideoxy method using this as a template. SEQ ID No. 38 of the Sequence Listing shows the nucleotide sequence, from the BamHI site to 80 bp upstream nucleotide, present in the region (the sequence of the complementary chain). Then, based on the sequence, the primer NPM-1 which hybridizes to a 3' part of the protease PFUS gene and contains a SphI site was synthesized. SEQ ID No. 39 of the Sequence Listing shows the nucleotide sequence of the primer NPM-1.

In addition, the primers mutRR and mutFR for elimination the BamHI sites which are present about 1.7 kb downstream from an initiation codon within the protease PFUS gene were synthesized. SEQ ID Nos. 40 and 41 of the Sequence Listing show the nucleotide sequences of the primers mutRR and mutFR, respectively.

(13) Preparation of plasmid pPS1 containing full length protease PUFS gene

Two sets of LA-PCR reaction mixtures containing *Pyrococcus furiosus* chromosomal DNA as a template and a combination of the primers NPF-4 and mutRR or a combination of the primers mutFR and NPM-1 were prepared, and a reaction of 30 cycles, each cycle consisting of 94° C. for 30 seconds-55° C. for 1 minute-68° C. for 3 minutes, was carried out. When agarose gel electrophoresis was carried out using an aliquot of this reaction mixture, an about 1.8 kb DNA fragment was amplified in a case of the use of the primer NPF-4 and mutRR, and an about 0.6 kb DNA fragment in a case of the use of the primers mutFR and NMP-1.

Each amplified DNA fragment from which the primers had been removed by using SUPREC-02 (manufactured by Takara Shuzo Co., Ltd.) was prepared from the two set of the PCR mixture. A LA-PCR reaction mixture containing both of these amplified DNA fragments and not containing the primers and LA Taq was prepared, which was used to carry out heat denaturation at 94° C. for 10 minutes, followed by cooling to 30° C. over 30 minutes and maintaining at 30° C. for 15 minutes to form a hetero duplex. Then, to this reaction mixture, LA Taq was added and was incubated at 72° C. for 3 minutes, the primers NPF-4 and NPM-1 were added thereto and a reaction of 25 cycles, each cycle consisting of 94° C. for 30 seconds-55° C. for 1 minute-68° C. for 3 minutes, was carried out. Amplification of an about 2.4 kb DNA fragment was observed in this reaction mixture.

The about 2.4 kb DNA fragment was digested with BamHI and SphI, the fragments were mixed with the plasmid pSNP1, described in Example 2-(11), from which the full length protease PFUS gene had been removed previously by digestion with BamHI and SphI, to allow to ligate, followed by introduction into *Bacillus subtilis* DB104. Plasmids were prepared from the resulting kanamycin-resistant transformant, and the plasmid with only one molecule of the about 2.4 kb fragment inserted was selected and designated the plasmid pPS1. *Bacillus subtilis* DB104 transformed with the plasmid DB104 was designated *Bacillus subtilis* DB104/pPS1.

FIG. 16 shows a restriction map of the plasmid pPS1.

(14) Amplification of DNA fragment of a region from the promoter to the signal sequence of subtilisin gene A primer for obtaining a region from promoter to signal sequence of subtilisin gene was synthesized. First, with reference to the nucleotide sequence of a promoter region of subtilisin gene described in J. Bacteriol., volume 171, page 2657–2665 (1989), the primer SUB4 which hybridizes to a part upstream of the region and contains the EcoRI site was synthesized (SEQ ID No. 36 of the Sequence Listing shows the nucleotide sequence of the primer SUB4). Then, with reference to the nucleotide sequence of a region encoding subtilisin described in J. Bacteriol., volume 158, page 411–418 (1984), the primer BmR1 which can be introduce the BamHI site just behind the signal sequence was synthesized (SEQ ID No. 37 of the Sequence Listing shows the nucleotide sequence of the primer BmR1).

The plasmid pKWZ containing subtilisin gene described in J. Bacteriol., volume 17, page 2657–2665 (1989) was used as a template to prepare a PCR reaction mixture containing the primers SUB4 and BmR1, and a reaction of 30 cycles, each cycle consisting of 94° C. for 30 seconds-55° C. for 1 minute-68° C. for 2 minutes, was carried out. Agarose gel electrophoresis of an aliquot of this reaction mixture confirmed amplification of an about 0.3 kb DNA fragment.

(15) Preparation of plasmid pNAPS1 containing protease PFUS gene for transformation of *Bacillus subtilis*

The about 0.3 kb DNA fragment was digested with EcoRI and BamHI, which was mixed with the plasmid pPS1, described in Example 2-(13), which previously had been digested with EcoRI and BamHI to allow to ligate, followed by introduction into *Bacillus subtilis* DB104. Plasmids were prepared from the resulting kanamycin-resistant transformant and the plasmid containing only one molecule of the about 0.3 kb fragment was selected and designated the plasmid pNAPS1. In addition, *Bacillus subtilis* DB104 transformed with the plasmid pNAPS1 was designated *Bacillus subtilis* DB104/pNAPS1.

FIG. 17 shows a restriction map of the plasmid pNAPS1.

Example 3

(1) Preparation of probe for detecting hyperthermostable protease gene The plasmid pTPR12 containing the protease PFUL gene was digested with BalI and HincII (both manufactured by Takara Shuzo Co., Ltd.), which was subjected to 1% agarose gel electrophoresis to recover the separated about 1 kb DNA fragment. A $^{32}$P-labeled DNA probe was prepared using the DNA fragment as a template and using BcaBEST DNA labeling kit and [α-32P] dCTP.

(2) Detection of hyperthermostable protease gene present in hyperthermophile *Staphylothermus marinus* and *Thermobacteroides proteoliticus*

Chromosomal DNAs were prepared from each 10 ml of cultures of *Staphylothermus marinus* DSM3639 and *Thermobacteroides proteoliticus* DSM5265 obtained from Deutsche Sammlung von Mikroorganismen und Zellkulturen GmbH according to the procedures described in Example 1-(3). Both chromosomal DNAs were digested with EcoRI, PstI, HindIII, XbaI and SacI, respectively, which were subjected to 1% agarose gel electrophoresis, followed by southern hybridization according to the procedures described in Example 1-(5). As a probe, $^{32}$P-labeled DNA probe prepared in Example 3-(1) was used. A membrane was washed at 37° C. in 2×SSC finally containing 0.5% SDS, rinsed with 2×SSC, and the autoradiogram was obtained. From this autoradiogram, a signal was recognized in an about 4.8 kb DNA fragment in a case of *Staphylothermus marinus* chromosomal DNA digested with PstI, and in an about 3.5 kb DNA fragment in a case of *Thermobacteroides proteoliticus* chromosomal DNA digested with XbaI, thus, indicating that a hyperthermostable protease gene which hybridizes with the protease PFUL gene was present in the *Staphylothermus marinus* and *Thermobacteroides proteoliticus* chromosomal DNA.

Example 4

(1) Preparation of crude enzyme preparation of protease PFUS and TCES

*Bacillus subtilis* DB104 in which the plasmid pSTC3 containing the hyperthermostable protease gene of the present invention had been introduced (*Bacillus subtilis* DB104/pSTC3) was cultured in 5 ml of LB medium (trypton 10 g/liter, yeast extract 5 g/liter, NaCl 5 g/liter, pH 7.2) containing 10 µg/ml kanamycin at 37° C. for 8 hours. 250 ml of the similar medium was prepared in 1 liter Erlenmeyer flask, which was inoculated with 5 ml of the above culture to culture at 37° C. for 16 hours. Ammonium sulfate was added to a supernatant obtained by centrifugation of the culture to 75% saturation, and the resulted precipitates were recovered by centrifugation. The recovered precipitates were suspended in 4 ml of 20 mM Tris-HCl, pH 7.5, which was dialyzed against the same buffer, and the resulting dialysate was used as crude enzyme preparation (enzyme preparation TC-3).

Crude enzyme preparations were prepared from *Bacillus subtilis* DB104 in which the plasmid pSNP1 containing the hyperthermostable protease gene of the present invention was introduced (*Bacillus subtilis* DB104/pSNP1) or *Bacillus subtilis* DB104 in which the plasmid pSPT1 containing the hyperthermostable protease of the present invention, according to the procedures described above, and the preparations were designated NP-1 and PT-1, respectively.

These enzyme preparations were used to examine the protease activity by the enzyme activity detecting method using the SDS-polyacrylamide gel containing gelatin or by the other activity detecting methods.

(2) Preparation of purified enzyme preparation of protease PFUS

Two tubes containing 5 ml of LB medium containing 10 µl/ml kanamycin were inoculated with *Bacillus subtilis* DB104 in which the plasmid pNAPS1 containing the hyperthermostable protease gene of the present invention obtained in Example 2-(18) was introduced (*Bacillus subtilis* DB104/pNAPS1), followed by cultivation at 37° C. for 7 hours with shaking. Six Erlenmeyer flasks of 500 ml volume, each containing 120 ml of the similar medium, were prepared, and each flask was inoculated with 1 ml of the above culture, followed by cultivation at 37° C. for 17 hours with shaking. The culture was centrifuged to obtain the cells and a culture supernatant.

The cells were suspended in 15 ml of 50 mM Tris-HCl, pH 7.5, and 30 mg of lysozyme (manufactured by Sigma) was added thereto, followed by digestion at 37° C. for 1.5 hours. The digestion solution was heat-treated at 95° C. for 15 minutes, followed by centrifugation to collect a supernatant. To 12 ml of the resulting supernatant was added 4 ml of an saturated ammonium sulfate solution, which was filtrated using 0.45 µm filter unit (Sterivex HV, manufactured by Millipore), and the filtrate was loaded onto the POROS PH column (4.6 mm ×150 mm: manufactured by PerSeptive Biosystems) equilibrated with 25 mM Tris-HCl, pH 7.5 containing ammonium sulfate at 25% saturation. The column was washed with the buffer used for equilibration, the gradient elution was performed by lowering the concentration of ammonium sulfate from 25% saturation to 0% saturation and at the same time increasing the concentration of acetonitrile from 0% to 20% to elute the PFUS protease, to obtain the purified enzyme preparation NAPS-1.

750 ml of the culture supernatant was dialyzed against 25 mM Tris-HCl, pH 8.0 and adsorbed onto Econo-Pack Q cartridge (manufactured by BioRad) equilibrated with the same buffer. Then, the adsorbed enzyme was eluted with a linear gradient of 0 to 1.5 M NaCl. The resulting active fraction was heat-treated at 95° C. for 1 hour, and an ⅓ volume of a saturated ammonium sulfate solution was added thereto. After the filtration was carried out using a 0.45 µm filter unit (Sterivex HV), the filtrate was loaded onto the POROS PH column (4.6 mm ×150 mm) equilibrated with 25 mM Tris-HCl, pH 7.5 containing ammonium sulfate at 25% saturation. The PFUS protease absorbed onto the column was eluted according to the procedures as in the enzyme preparation NAPS-1 to obtain the purified enzyme preparation NAPS-1.

To an appropriate amount of the purified enzyme preparation NAPS-1 or NAPS-1S was added trichloroacetic acid to the final concentration of 8.3% to precipitate the proteins in the enzyme preparation, which were recovered by centrifugation. The recovered precipitated protein were dissolved in a distilled water, an ¼ amount of a sample buffer (50 mM Tris-HCl, pH 7.5, 5% SDS, 5% 2-mercaptoethanol, 0.005% Bromophenol Blue, 50% glycerol) was added thereto, which was treated at 100° C. for 5 minutes and subjected to electrophoresis using 0.1% SDS-10% polyacrylamide gel. After run, the gel was stained in 2.5% Coomassie Brilliant Blue R-250, 25% ethanol, and 10% acetic acid for 30 minutes, transferred in 25% methanol, and 7% acetic acid and the excess dye was removed over 3 to 15 hours. Both enzyme preparations NAPS-1 and NAPS-1S showed a single band, and a molecular weight deduced from migrated distance was about 4.5 kDa.

(3) Sequencing of N-terminal of mature protease PUFS

The purified enzyme preparation NAPS-1 prepared in Example 4-(2) was subjected to electrophoresis using 0.1% SDS-10% polyacrylamide gel, and the proteins on the gel was blotted onto a PVDF membrane (manufactured by Millipore) using Semidry Blotter (manufactured by Nihon Eido). Blotting was carried out according to a method described in Electrophoresis, volume 11, page 573–580 (1990). After blotting, the membrane was stained with a solution of 1% Coomassie Brilliant Blue R-250, in 50% methanol, and destained with a 60% methanol solution. A part of the membrane which had been stained was cut off, followed by sequencing of the N-terminal amino acid sequence by the automated Edman degradation using G1000A protein sequencer (manufactured by Hewlette Packard). SEQ ID No. 42 shows the resultant N-terminal amino acid sequence.

What is claimed is:

1. An isolated hyperthermostable protease, comprising the amino acid sequence of SEQ ID NO: 3, or functional equivalent of said hyperthermostable protease in which one amino acid to 5% of the amino acid residues of SEO ID NO: 3 are mutated, wherein said functional equivalent has casein hydrolyzing activity and is inhibited by phenylmethane-sulfonyl fluoride.

2. An isolated polynucleotide encoding the hyperthero-mostable protease or functional equivalent thereof as defined in claim 1.

3. The polynucleotide according to claim 2, which comprises the nucleotide sequence of SEQ ID NO:4.

4. The polynucleotide according to claim 2, which hybridizes to SEQ ID NO: 4 under stringent conditions.

5. A method for preparing a hyperthermostable protease which comprises culturing a transformant containing the polynucleotide as defined in claim 2 to produce said hyperthermostable protease, and harvesting said produced hyperthermostable protease from the culture.

* * * * *

SEQUENCE LISTING (1) GENERAL INFORMATION:

(iii) NUMBER OF SEQUENCES: 42

(2) INFORMATION FOR SEQ ID NO: 1:

(i) SEQUENCE CHARACTERISTICS:
    (A) LENGTH: 659 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 1:

```
Met Lys Arg Leu Gly Ala Val Val Leu Ala Leu Val Leu Val Gly
                 5                  10                  15

Leu Leu Ala Gly Thr Ala Leu Ala Ala Pro Val Lys Pro Val Val
                20                  25                  30

Arg Asn Asn Ala Val Gln Gln Lys Asn Tyr Gly Leu Leu Thr Pro
                35                  40                  45

Gly Leu Phe Lys Lys Val Gln Arg Met Asn Trp Asn Gln Glu Val
                50                  55                  60

Asp Thr Val Ile Met Phe Gly Ser Tyr Gly Asp Arg Asp Arg Ala
                65                  70                  75

Val Lys Val Leu Arg Leu Met Gly Ala Gln Val Lys Tyr Ser Tyr
                80                  85                  90

Lys Ile Ile Pro Ala Val Ala Val Lys Ile Lys Ala Arg Asp Leu
                95                 100                 105

Leu Leu Ile Ala Gly Met Ile Asp Thr Gly Tyr Phe Gly Asn Thr
               110                 115                 120

Arg Val Ser Gly Ile Lys Phe Ile Gln Glu Asp Tyr Lys Val Gln
               125                 130                 135

Val Asp Asp Ala Thr Ser Val Ser Gln Ile Gly Ala Asp Thr Val
               140                 145                 150

Trp Asn Ser Leu Gly Tyr Asp Gly Ser Gly Val Val Val Ala Ile
               155                 160                 165

Val Asp Thr Gly Ile Asp Ala Asn His Pro Asp Leu Lys Gly Lys
               170                 175                 180

Val Ile Gly Trp Tyr Asp Ala Val Asn Gly Arg Ser Thr Pro Tyr
               185                 190                 195

Asp Asp Gln Gly His Gly Thr His Val Ala Gly Ile Val Ala Gly
               200                 205                 210

Thr Gly Ser Val Asn Ser Gln Tyr Ile Gly Val Ala Pro Gly Ala
               215                 220                 225

Lys Leu Val Gly Val Lys Val Leu Gly Ala Asp Gly Ser Gly Ser
               230                 235                 240

Val Ser Thr Ile Ile Ala Gly Val Asp Trp Val Val Gln Asn Lys
               245                 250                 255

Asp Lys Tyr Gly Ile Arg Val Ile Asn Leu Ser Leu Gly Ser Ser
               260                 265                 270

Gln Ser Ser Asp Gly Thr Asp Ser Leu Ser Gln Ala Val Asn Asn
               275                 280                 285

Ala Trp Asp Ala Gly Ile Val Val Cys Val Ala Ala Gly Asn Ser
               290                 295                 300

Gly Pro Asn Thr Tyr Thr Val Gly Ser Pro Ala Ala Ala Ser Lys
               305                 310                 315

Val Ile Thr Val Gly Ala Val Asp Ser Asn Asp Asn Ile Ala Ser
               320                 325                 330

Phe Ser Ser Arg Gly Pro Thr Ala Asp Gly Arg Leu Lys Pro Glu
               335                 340                 345
```

```
Val Val Ala Pro Gly Val Asp Ile Ile Ala Pro Arg Ala Ser Gly
                350                 355                 360

Thr Ser Met Gly Thr Pro Ile Asn Asp Tyr Tyr Thr Lys Ala Ser
                365                 370                 375

Gly Thr Ser Met Ala Thr Pro His Val Ser Gly Val Gly Ala Leu
                380                 385                 390

Ile Leu Gln Ala His Pro Ser Trp Thr Pro Asp Lys Val Lys Thr
                395                 400                 405

Ala Leu Ile Glu Thr Ala Asp Ile Val Ala Pro Lys Glu Ile Ala
                410                 415                 420

Asp Ile Ala Tyr Gly Ala Gly Arg Val Asn Val Tyr Lys Ala Ile
                425                 430                 435

Lys Tyr Asp Asp Tyr Ala Lys Leu Thr Phe Thr Gly Ser Val Ala
                440                 445                 450

Asp Lys Gly Ser Ala Thr His Thr Phe Asp Val Ser Gly Ala Thr
                455                 460                 465

Phe Val Thr Ala Thr Leu Tyr Trp Asp Thr Gly Ser Ser Asp Ile
                470                 475                 480

Asp Leu Tyr Leu Tyr Asp Pro Asn Gly Asn Glu Val Asp Tyr Ser
                485                 490                 495

Tyr Thr Ala Tyr Tyr Gly Phe Glu Lys Val Gly Tyr Tyr Asn Pro
                500                 505                 510

Thr Ala Gly Thr Trp Thr Val Lys Val Ser Tyr Lys Gly Ala
                515                 520                 525

Ala Asn Tyr Gln Val Asp Val Val Ser Asp Gly Ser Leu Ser Gln
                530                 535                 540

Ser Gly Gly Gly Asn Pro Asn Pro Asn Pro Asn Pro Asn Pro Thr
                545                 550                 555

Pro Thr Thr Asp Thr Gln Thr Phe Thr Gly Ser Val Asn Asp Tyr
                560                 565                 570

Trp Asp Thr Ser Asp Thr Phe Thr Met Asn Val Asn Ser Gly Ala
                575                 580                 585

Thr Lys Ile Thr Gly Asp Leu Thr Phe Asp Thr Ser Tyr Asn Asp
                590                 595                 600

Leu Asp Leu Tyr Leu Tyr Asp Pro Asn Gly Asn Leu Val Asp Arg
                605                 610                 615

Ser Thr Ser Ser Asn Ser Tyr Glu His Val Glu Tyr Ala Asn Pro
                620                 625                 630

Ala Pro Gly Thr Trp Thr Phe Leu Val Tyr Ala Tyr Ser Thr Tyr
                635                 640                 645

Gly Trp Ala Asp Tyr Gln Leu Lys Ala Val Val Tyr Tyr Gly
                650                 655

(2) INFORMATION FOR SEQ ID NO: 2:

(i) SEQUENCE CHARACTERISTICS:
        (A) LENGTH: 1977 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 2:

ATGAAGAGGT TAGGTGCTGT GGTGCTGGCA CTGGTGCTCG TGGGTCTTCT GGCCGGAACG      60

GCCCTTGCGG CACCCGTAAA ACCGGTTGTC AGGAACAACG CGGTTCAGCA GAAGAACTAC     120
```

```
GGACTGCTGA CCCCGGGACT GTTCAAGAAA GTCCAGAGGA TGAACTGGAA CCAGGAAGTG      180

GACACCGTCA TAATGTTCGG GAGCTACGGA GACAGGGACA GGGCGGTTAA GGTACTGAGG      240

CTCATGGGCG CCCAGGTCAA GTACTCCTAC AAGATAATCC CTGCTGTCGC GGTTAAAATA      300

AAGGCCAGGG ACCTTCTGCT GATCGCGGGC ATGATAGACA CGGGTTACTT CGGTAACACA      360

AGGGTCTCGG GCATAAAGTT CATACAGGAG GATTACAAGG TTCAGGTTGA CGACGCCACT      420

TCCGTCTCCC AGATAGGGGC CGATACCGTC TGGAACTCCC TCGGCTACGA CGGAAGCGGT      480

GTGGTGGTTG CCATCGTCGA TACGGGTATA GACGCGAACC ACCCCGATCT GAAGGGCAAG      540

GTCATAGGCT GGTACGACGC CGTCAACGGC AGGTCGACCC CCTACGATGA CCAGGGACAC      600

GGAACCCACG TTGCGGGTAT CGTTGCCGGA ACCGGCAGCG TTAACTCCCA GTACATAGGC      660

GTCGCCCCCG GCGCGAAGCT CGTCGGCGTC AAGGTTCTCG GTGCCGACGG TTCGGGAAGC      720

GTCTCCACCA TCATCGCGGG TGTTGACTGG GTCGTCCAGA ACAAGGACAA GTACGGGATA      780

AGGGTCATCA ACCTCTCCCT CGGCTCCTCC CAGAGCTCCG ACGGAACCGA CTCCCTCAGT      840

CAGGCCGTCA ACAACGCCTG GGACGCCGGT ATAGTAGTCT GCGTCGCCGC CGGCAACAGC      900

GGGCCGAACA CCTACACCGT CGGCTCACCC GCCGCCGCGA GCAAGGTCAT AACCGTCGGT      960

GCAGTTGACA GCAACGACAA CATCGCCAGC TTCTCCAGCA GGGACCGAC CGCGGACGGA     1020

AGGCTCAAGC CGGAAGTCGT CGCCCCCGGC GTTGACATCA TAGCCCCGCG CGCCAGCGGA     1080

ACCAGCATGG GCACCCCGAT AAACGACTAC TACACCAAGG CCTCTGGAAC CAGCATGGCC     1140

ACCCCGCACG TTTCGGGCGT TGGCGCGCTC ATCCTCCAGG CCCACCCGAG CTGGACCCCG     1200

GACAAGGTGA AGACCGCCCT CATCGAGACC GCCGACATAG TCGCCCCCAA GGAGATAGCG     1260

GACATCGCCT ACGGTGCGGG TAGGGTGAAC GTCTACAAGG CCATCAAGTA CGACGACTAC     1320

GCCAAGCTCA CCTTCACCGG CTCCGTCGCC GACAAGGGAA GCGCCACCCA CACCTTCGAC     1380

GTCAGCGGCG CCACCTTCGT GACCGCCACC CTCTACTGGG ACACGGGCTC GAGCGACATC     1440

GACCTCTACC TCTACGACCC CAACGGGAAC GAGGTTGACT ACTCCTACAC CGCCTACTAC     1500

GGCTTCGAGA AGGTCGGCTA CTACAACCCG ACCGCCGGAA CCTGGACGGT CAAGGTCGTC     1560

AGCTACAAGG GCGCGGCGAA CTACCAGGTC GACGTCGTCA GCGACGGGAG CCTCAGCCAG     1620

TCCGGCGGCG GCAACCCGAA TCCAAACCCC AACCCGAACC CAACCCCGAC CACCGACACC     1680

CAGACCTTCA CCGGTTCCGT TAACGACTAC TGGGACACCA GCGACACCTT CACCATGAAC     1740

GTCAACAGCG GTGCCACCAA GATAACCGGT GACCTGACCT TCGATACTTC CTACAACGAC     1800

CTCGACCTCT ACCTCTACGA CCCCAACGGC AACCTCGTTG ACAGGTCCAC GTCGAGCAAC     1860

AGCTACGAGC ACGTCGAGTA CGCCAACCCC GCCCCGGGAA CCTGGACGTT CCTCGTCTAC     1920

GCCTACAGCA CCTACGGCTG GGCGGACTAC CAGCTCAAGG CCGTCGTCTA CTACGGG       1977
```

(2) INFORMATION FOR SEQ ID NO: 3:

(i) SEQUENCE CHARACTERISTICS:
        (A) LENGTH: 522 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION:/note= Xaa at position 428 is Gly or
           Val.

(xi) SEQUENCE DESCRIPTION: SEQ ID NO: 3:

-continued

```
Ala Glu Leu Glu Gly Leu Asp Glu Ser Ala Ala Gln Val Met Ala
              5                  10                  15

Thr Tyr Val Trp Asn Leu Gly Tyr Asp Gly Ser Gly Ile Thr Ile
             20                  25                  30

Gly Ile Ile Asp Thr Gly Ile Asp Ala Ser His Pro Asp Leu Gln
             35                  40                  45

Gly Lys Val Ile Gly Trp Val Asp Phe Val Asn Gly Arg Ser Tyr
             50                  55                  60

Pro Tyr Asp Asp His Gly His Gly Thr His Val Ala Ser Ile Ala
             65                  70                  75

Ala Gly Thr Gly Ala Ala Ser Asn Gly Lys Tyr Lys Gly Met Ala
             80                  85                  90

Pro Gly Ala Lys Leu Ala Gly Ile Lys Val Leu Gly Ala Asp Gly
             95                 100                 105

Ser Gly Ser Ile Ser Thr Ile Ile Lys Gly Val Glu Trp Ala Val
            110                 115                 120

Asp Asn Lys Asp Lys Tyr Gly Ile Lys Val Ile Asn Leu Ser Leu
            125                 130                 135

Gly Ser Ser Gln Ser Ser Asp Gly Thr Asp Ala Leu Ser Gln Ala
            140                 145                 150

Val Asn Ala Ala Trp Asp Ala Gly Leu Val Val Val Ala Ala
            155                 160                 165

Gly Asn Ser Gly Pro Asn Lys Tyr Thr Ile Gly Ser Pro Ala Ala
            170                 175                 180

Ala Ser Lys Val Ile Thr Val Gly Ala Val Asp Lys Tyr Asp Val
            185                 190                 195

Ile Thr Ser Phe Ser Ser Arg Gly Pro Thr Ala Asp Gly Arg Leu
            200                 205                 210

Lys Pro Glu Val Ala Pro Gly Asn Trp Ile Ile Ala Ala Arg
            215                 220                 225

Ala Ser Gly Thr Ser Met Gly Gln Pro Ile Asn Asp Tyr Tyr Thr
            230                 235                 240

Ala Ala Pro Gly Thr Ser Met Ala Thr Pro His Val Ala Gly Ile
            245                 250                 255

Ala Ala Leu Leu Leu Gln Ala His Pro Ser Trp Thr Pro Asp Lys
            260                 265                 270

Val Lys Thr Ala Leu Ile Glu Thr Ala Asp Ile Val Lys Pro Asp
            275                 280                 285

Glu Ile Ala Asp Ile Ala Tyr Gly Ala Gly Arg Val Asn Ala Tyr
            290                 295                 300

Lys Ala Ile Asn Tyr Asp Asn Tyr Ala Lys Leu Val Phe Thr Gly
            305                 310                 315

Tyr Val Ala Asn Lys Gly Ser Gln Thr His Gln Phe Val Ile Ser
            320                 325                 330

Gly Ala Ser Phe Val Thr Ala Thr Leu Tyr Trp Asp Asn Ala Asn
            335                 340                 345

Ser Asp Leu Asp Leu Tyr Leu Tyr Asp Pro Asn Gly Asn Gln Val
            350                 355                 360

Asp Tyr Ser Tyr Thr Ala Tyr Tyr Gly Phe Glu Lys Val Gly Tyr
            365                 370                 375

Tyr Asn Pro Thr Asp Gly Thr Trp Thr Ile Lys Val Val Ser Tyr
            380                 385                 390
```

```
Ser Gly Ser Ala Asn Tyr Gln Val Asp Val Ser Asp Gly Ser
            395                 400                 405

Leu Ser Gln Pro Gly Ser Ser Pro Ser Pro Gln Pro Glu Pro Thr
            410                 415                 420

Val Asp Ala Lys Thr Phe Gln Xaa Ser Asp His Tyr Tyr Tyr Asp
            425                 430                 435

Arg Ser Asp Thr Phe Thr Met Thr Val Asn Ser Gly Ala Thr Lys
            440                 445                 450

Ile Thr Gly Asp Leu Val Phe Asp Thr Ser Tyr His Asp Leu Asp
            455                 460                 465

Leu Tyr Leu Tyr Asp Pro Asn Gln Lys Leu Val Asp Arg Ser Glu
            470                 475                 480

Ser Pro Asn Ser Tyr Glu His Val Glu Tyr Leu Thr Pro Ala Pro
            485                 490                 495

Gly Thr Trp Tyr Phe Leu Val Tyr Ala Tyr Tyr Thr Tyr Gly Trp
            500                 505                 510

Ala Tyr Tyr Glu Leu Thr Ala Lys Val Tyr Tyr Gly
            515                 520
```

(2) INFORMATION FOR SEQ ID NO: 4:

(i) SEQUENCE CHARACTERISTICS:
      (A) LENGTH: 1566 base pairs
      (B) TYPE: nucleic acid
      (C) STRANDEDNESS: double
      (D) TOPOLOGY: linear (ii) MOLECULE TYPE: genomic DNA (ix) FEATURE:
      (D) OTHER INFORMATION:/note= N at position 1283 is G or T.

(xi) SEQUENCE DESCRIPTION: SEQ ID NO: 4:

```
GCAGAATTAG AAGGACTGGA TGAGTCTGCA GCTCAAGTTA TGGCAACTTA CGTTTGGAAC     60

TTGGGATATG ATGGTTCTGG AATCACAATA GGAATAATTG ACACTGGAAT TGACGCTTCT    120

CATCCAGATC TCCAAGGAAA AGTAATTGGG TGGGTAGATT TTGTCAATGG TAGGAGTTAT    180

CCATACGATG ACCATGGACA TGGAACTCAT GTAGCTTCAA TAGCAGCTGG TACTGGAGCA    240

GCAAGTAATG GCAAGTACAA GGGAATGGCT CCAGGAGCTA AGCTGGCGGG AATTAAGGTT    300

CTAGGTGCCG ATGGTTCTGG AAGCATATCT ACTATAATTA AGGGAGTTGA GTGGGCCGTT    360

GATAACAAAG ATAAGTACGG AATTAAGGTC ATTAATCTTT CTCTTGGTTC AAGCCAGAGC    420

TCAGATGGTA CTGACGCTCT AAGTCAGGCT GTTAATGCAG CGTGGGATGC TGGATTAGTT    480

GTTGTGGTTG CCGCTGGAAA CAGTGGACCT AACAAGTATA CAATCGGTTC TCCAGCAGCT    540

GCAAGCAAAG TTATTACAGT TGGAGCCGTT GACAAGTATG ATGTTATAAC AAGCTTCTCA    600

AGCAGAGGGC CAACTGCAGA CGGCAGGCTT AAGCCTGAGG TTGTTGCTCC AGGAAACTGG    660

ATAATTGCTG CCAGAGCAAG TGGAACTAGC ATGGGTCAAC CAATTAATGA CTATTACACA    720

GCAGCTCCTG GACATCAAT GGCAACTCCT CACGTAGCTG GTATTGCAGC CCTCTTGCTC    780

CAAGCACACC CGAGCTGGAC TCCAGACAAA GTAAAAACAG CCCTCATAGA AACTGCTGAT    840

ATCGTAAAGC CAGATGAAAT AGCCGATATA GCCTACGGTG CAGGTAGGGT TAATGCATAC    900

AAGGCTATAA ACTACGATAA CTATGCAAAG CTAGTGTTCA CTGGATATGT TGCCAACAAA    960

GGCAGCCAAA CTCACCAGTT CGTTATTAGC GGAGCTTCGT TCGTAACTGC ACATTATAC    1020

TGGGACAATG CCAATAGCGA CCTTGATCTT TACCTCTACG ATCCCAATGG AAACCAGGTT    1080
```

-continued

```
GACTACTCTT ACACCGCCTA CTATGGATTC GAAAAGGTTG GTTATTACAA CCCAACTGAT    1140

GGAACATGGA CAATTAAGGT TGTAAGCTAC AGCGGAAGTG CAAACTATCA AGTAGATGTG    1200

GTAAGTGATG GTTCCCTTTC ACAGCCTGGA AGTTCACCAT CTCCACAACC AGAACCAACA    1260

GTAGACGCAA AGACGTTCCA AGNATCCGAT CACTACTACT ATGACAGGAG CGACACCTTT    1320

ACAATGACCG TTAACTCTGG GGCTACAAAG ATTACTGGAG ACCTAGTGTT TGACACAAGC    1380

TACCATGATC TTGACCTTTA CCTCTACGAT CCTAACCAGA AGCTTGTAGA TAGATCGGAG    1440

AGTCCCAACA GCTACGAACA CGTAGAATAC TTAACCCCCG CCCCAGGAAC CTGGTACTTC    1500

CTAGTATATG CCTACTACAC TTACGGTTGG GCTTACTACG AGCTGACGGC TAAAGTTTAT    1560

TATGGC                                                               1566
```

(2) INFORMATION FOR SEQ ID NO: 5:

(i) SEQUENCE CHARACTERISTICS:
        (A) LENGTH: 659 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Met Lys Gly Leu Lys Ala Leu Ile Leu Val Ile Leu Val Leu Gly
              5                   10                  15

Leu Val Val Gly Ser Val Ala Ala Ala Pro Glu Lys Lys Val Glu
             20                   25                  30

Gln Val Arg Asn Val Glu Lys Asn Tyr Gly Leu Leu Thr Pro Gly
             35                   40                  45

Leu Phe Arg Lys Ile Gln Lys Leu Asn Pro Asn Glu Glu Ile Ser
             50                   55                  60

Thr Val Ile Val Phe Glu Asn His Arg Glu Lys Glu Ile Ala Val
             65                   70                  75

Arg Val Leu Glu Leu Met Gly Ala Lys Val Arg Tyr Val Tyr His
             80                   85                  90

Ile Ile Pro Ala Ile Ala Ala Asp Leu Lys Val Arg Asp Leu Leu
             95                  100                 105

Val Ile Ser Gly Leu Thr Gly Gly Lys Ala Lys Leu Ser Gly Val
            110                  115                 120

Arg Phe Ile Gln Glu Asp Tyr Lys Val Thr Val Ser Ala Glu Leu
            125                  130                 135

Glu Gly Leu Asp Glu Ser Ala Ala Gln Val Met Ala Thr Tyr Val
            140                  145                 150

Trp Asn Leu Gly Tyr Asp Gly Ser Gly Ile Thr Ile Gly Ile Ile
            155                  160                 165

Asp Thr Gly Ile Asp Ala Ser His Pro Asp Leu Gln Gly Lys Val
            170                  175                 180

Ile Gly Trp Val Asp Phe Val Asn Gly Arg Ser Tyr Pro Tyr Asp
            185                  190                 195

Asp His Gly His Gly Thr His Val Ala Ser Ile Ala Ala Gly Thr
            200                  205                 210

Gly Ala Ala Ser Asn Gly Lys Tyr Lys Gly Met Ala Pro Gly Ala
            215                  220                 225

Lys Leu Ala Gly Ile Lys Val Leu Gly Ala Asp Gly Ser Gly Ser
            230                  235                 240
```

-continued

```
Ile Ser Thr Ile Ile Lys Gly Val Glu Trp Ala Val Asp Asn Lys
                245                 250                 255

Asp Lys Tyr Gly Ile Lys Val Ile Asn Leu Ser Leu Gly Ser Ser
            260                 265                 270

Gln Ser Ser Asp Gly Thr Asp Ser Leu Ser Gln Ala Val Asn Asn
        275                 280                 285

Ala Trp Asp Ala Gly Ile Val Val Cys Val Ala Ala Gly Asn Ser
    290                 295                 300

Gly Pro Asn Thr Tyr Thr Val Gly Ser Pro Ala Ala Ala Ser Lys
                305                 310                 315

Val Ile Thr Val Gly Ala Val Asp Ser Asn Asp Asn Ile Ala Ser
            320                 325                 330

Phe Ser Ser Arg Gly Pro Thr Ala Asp Gly Arg Leu Lys Pro Glu
        335                 340                 345

Val Val Ala Pro Gly Val Asp Ile Ile Ala Pro Arg Ala Ser Gly
    350                 355                 360

Thr Ser Met Gly Thr Pro Ile Asn Asp Tyr Tyr Thr Lys Ala Ser
                365                 370                 375

Gly Thr Ser Met Ala Thr Pro His Val Ser Gly Val Gly Ala Leu
            380                 385                 390

Ile Leu Gln Ala His Pro Ser Trp Thr Pro Asp Lys Val Lys Thr
        395                 400                 405

Ala Leu Ile Glu Thr Ala Asp Ile Val Ala Pro Lys Glu Ile Ala
    410                 415                 420

Asp Ile Ala Tyr Gly Ala Gly Arg Val Asn Val Tyr Lys Ala Ile
                425                 430                 435

Lys Tyr Asp Asp Tyr Ala Lys Leu Thr Phe Thr Gly Ser Val Ala
            440                 445                 450

Asp Lys Gly Ser Ala Thr His Thr Phe Asp Val Ser Gly Ala Thr
        455                 460                 465

Phe Val Thr Ala Thr Leu Tyr Trp Asp Thr Gly Ser Ser Asp Ile
    470                 475                 480

Asp Leu Tyr Leu Tyr Asp Pro Asn Gly Asn Glu Val Asp Tyr Ser
                485                 490                 495

Tyr Thr Ala Tyr Tyr Gly Phe Glu Lys Val Gly Tyr Tyr Asn Pro
            500                 505                 510

Thr Ala Gly Thr Trp Thr Val Lys Val Val Ser Tyr Lys Gly Ala
        515                 520                 525

Ala Asn Tyr Gln Val Asp Val Val Ser Asp Gly Ser Leu Ser Gln
    530                 535                 540

Ser Gly Gly Gly Asn Pro Asn Pro Asn Pro Asn Pro Asn Pro Thr
                545                 550                 555

Pro Thr Thr Asp Thr Gln Thr Phe Thr Gly Ser Val Asn Asp Tyr
            560                 565                 570

Trp Asp Thr Ser Asp Thr Phe Thr Met Asn Val Asn Ser Gly Ala
        575                 580                 585

Thr Lys Ile Thr Gly Asp Leu Thr Phe Asp Thr Ser Tyr Asn Asp
    590                 595                 600

Leu Asp Leu Tyr Leu Tyr Asp Pro Asn Gly Asn Leu Val Asp Arg
                605                 610                 615

Ser Thr Ser Ser Asn Ser Tyr Glu His Val Glu Tyr Ala Asn Pro
            620                 625                 630

Ala Pro Gly Thr Trp Thr Phe Leu Val Tyr Ala Tyr Ser Thr Tyr
```

```
                635                 640                 645
Gly Trp Ala Asp Tyr Gln Leu Lys Ala Val Val Tyr Tyr Gly
                    650                 655
```

(2) INFORMATION FOR SEQ ID NO: 6:

(i) SEQUENCE CHARACTERISTICS:
        (A) LENGTH: 1977 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 6:

```
ATGAAGGGGC TGAAAGCTCT CATATTAGTG ATTTTAGTTC TAGGTTTGGT AGTAGGGAGC      60

GTAGCGGCAG CTCCAGAGAA GAAAGTTGAA CAAGTAAGAA ATGTTGAGAA GAACTATGGT     120

CTGCTAACGC CAGGACTGTT CAGAAAAATT CAAAAATTGA ATCCTAACGA GGAAATCAGC     180

ACAGTAATTG TATTTGAAAA CCATAGGGAA AAAGAAATTG CAGTAAGAGT TCTTGAGTTA     240

ATGGGTGCAA AAGTTAGGTA TGTGTACCAT ATTATACCCG CAATAGCTGC CGATCTTAAG     300

GTTAGAGACT TACTAGTCAT CTCAGGTTTA CAGGGGGTA AAGCTAAGCT TTCAGGTGTT      360

AGGTTTATCC AGGAAGACTA CAAAGTTACA GTTTCAGCAG AATTAGAAGG ACTGGATGAG     420

TCTGCAGCTC AAGTTATGGC AACTTACGTT TGGAACTTGG GATATGATGG TTCTGGAATC     480

ACAATAGGAA TAATTGACAC TGGAATTGAC GCTTCTCATC CAGATCTCCA AGGAAAAGTA     540

ATTGGGTGGG TAGATTTTGT CAATGGTAGG AGTTATCCAT ACGATGACCA TGGACATGGA     600

ACTCATGTAG CTTCAATAGC AGCTGGTACT GGAGCAGCAA GTAATGGCAA GTACAAGGGA     660

ATGGCTCCAG GAGCTAAGCT GGCGGGAATT AAGGTTCTAG GTGCCGATGG TTCTGGAAGC     720

ATATCTACTA TAATTAAGGG AGTTGAGTGG GCCGTTGATA ACAAAGATAA GTACGGAATT     780

AAGGTCATTA ATCTTTCTCT TGGTTCAAGC CAGAGCTCCG ACGGAACCGA CTCCCTCAGT     840

CAGGCCGTCA CAACGCCTG GACGCCGGT ATAGTAGTCT GCGTCGCCGC CGGCAACAGC       900

GGGCCGAACA CCTACACCGT CGGCTCACCC GCCGCCGCGA GCAAGGTCAT AACCGTCGGT     960

GCAGTTGACA GCAACGACAA CATCGCCAGC TTCTCCAGCA GGGACCGAC CGCGGACGGA     1020

AGGCTCAAGC CGGAAGTCGT CGCCCCCGGC GTTGACATCA TAGCCCCGCG CGCCAGCGGA    1080

ACCAGCATGG GCACCCCGAT AAACGACTAC TACACCAAGG CCTCTGGAAC CAGCATGGCC    1140

ACCCCGCACG TTTCGGGCGT TGGCGCGCTC ATCCTCCAGG CCCACCCGAG CTGGACCCCG    1200

GACAAGGTGA AGACCGCCCT CATCGAGACC GCCGACATAG TCGCCCCCAA GGAGATAGCG    1260

GACATCGCCT ACGGTGCGGG TAGGGTGAAC GTCTACAAGG CCATCAAGTA CGACGACTAC    1320

GCCAAGCTCA CCTTCACCGG CTCCGTCGCC GACAAGGGAA GCGCCACCCA CACCTTCGAC    1380

GTCAGCGGCG CCACCTTCGT GACCGCCACC CTCTACTGGG ACACGGGCTC GAGCGACATC    1440

GACCTCTACC TCTACGACCC CAACGGGAAC GAGGTTGACT ACTCCTACAC CGCCTACTAC    1500

GGCTTCGAGA AGGTCGGCTA CTACAACCCG ACCGCCGGAA CCTGGACGGT CAAGGTCGTC    1560

AGCTACAAGG GCGCGGCGAA CTACCAGGTC GACGTCGTCA GCGACGGGAG CCTCAGCCAG    1620

TCCGGCGGCG GCAACCCGAA TCCAAACCCC AACCCGAACC CAACCCCGAC CACCGACACC    1680

CAGACCTTCA CCGGTTCCGT TAACGACTAC TGGGACACCA GCGACACCTT CACCATGAAC    1740

GTCAACAGCG GTGCCACCAA GATAACCGGT GACCTGACCT TCGATACTTC CTACAACGAC    1800

CTCGACCTCT ACCTCTACGA CCCCAACGGC AACCTCGTTG ACAGGTCCAC GTCGAGCAAC    1860
```

| | |
|---|---|
| AGCTACGAGC ACGTCGAGTA CGCCAACCCC GCCCCGGGAA CCTGGACGTT CCTCGTCTAC | 1920 |
| GCCTACAGCA CCTACGGCTG GGCGGACTAC CAGCTCAAGG CCGTCGTCTA CTACGGG | 1977 |

(2) INFORMATION FOR SEQ ID NO: 7:

(i) SEQUENCE CHARACTERISTICS:
        (A) LENGTH: 4765 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 7:

| | |
|---|---|
| TTTAAATTAT AAGATATAAT CACTCCGAGT GATGAGTAAG ATACATCATT ACAGTCCCAA | 60 |
| AATGTTTATA ATTGGAACGC AGTGAATATA CAAAATGAAT ATAACCTCGG AGGTGACTGT | 120 |
| AGAATGAATA AGAAGGGACT TACTGTGCTA TTTATAGCGA TAATGCTCCT TTCAGTAGTT | 180 |
| CCAGTGCACT TTGTGTCCGC AGAAACACCA CCGGTTAGTT CAGAAAATTC AACAACTTCT | 240 |
| ATACTCCCTA ACCAACAAGT TGTGACAAAA GAAGTTTCAC AAGCGGCGCT TAATGCTATA | 300 |
| ATGAAAGGAC AACCCAACAT GGTTCTTATA ATCAAGACTA AGGAAGGCAA ACTTGAAGAG | 360 |
| GCAAAAACCG AGCTTGAAAA GCTAGGTGCA GAGATTCTTG ACGAAAATAG AGTTCTTAAC | 420 |
| ATGTTGCTAG TTAAGATTAA GCCTGAGAAA GTTAAAGAGC TCAACTATAT CTCATCTCTT | 480 |
| GAAAAAGCCT GGCTTAACAG AGAAGTTAAG CTTTCCCCTC CAATTGTCGA AAAGGACGTC | 540 |
| AAGACTAAGG AGCCCTCCCT AGAACCAAAA ATGTATAACA GCACCTGGGT AATTAATGCT | 600 |
| CTCCAGTTCA TCCAGGAATT TGGATATGAT GGTAGTGGTG TTGTTGTTGC AGTACTTGAC | 660 |
| ACGGGAGTTG ATCCGAACCA TCCTTTCTTG AGCATAACTC CAGATGGACG CAGGAAAATT | 720 |
| ATAGAATGGA AGGATTTTAC AGACGAGGGA TTCGTGGATA CATCATTCAG CTTTAGCAAG | 780 |
| GTTGTAAATG GGACTCTTAT AATTAACACA ACATTCCAAG TGGCCTCAGG TCTCACGCTG | 840 |
| AATGAATCGA CAGGACTTAT GGAATACGTT GTTAAGACTG TTTACGTGAG CAATGTGACC | 900 |
| ATTGGAAATA TCACTTCTGC TAATGGCATC TATCACTTCG GCCTGCTCCC AGAAAGATAC | 960 |
| TTCGACTTAA ACTTCGATGG TGATCAAGAG GACTTCTATC CTGTCTTATT AGTTAACTCC | 1020 |
| ACTGGCAATG GTTATGACAT TGCATATGTG GATACTGACC TTGACTACGA CTTCACCGAC | 1080 |
| GAAGTTCCAC TTGGCCAGTA CAACGTTACT TATGATGTTG CTGTTTTTAG CTACTACTAC | 1140 |
| GGTCCTCTCA ACTACGTGCT TGCAGAAATA GATCCTAACG GAGAATATGC AGTATTTGGG | 1200 |
| TGGGATGGTC ACGGTCACGG AACTCACGTA GCTGGAACTG TTGCTGGTTA CGACAGCAAC | 1260 |
| AATGATGCTT GGGATTGGCT CAGTATGTAC TCTGGTGAAT GGGAAGTGTT CTCAAGACTC | 1320 |
| TATGGTTGGG ATTATACGAA CGTTACCACA GACACCGTGC AGGGTGTTGC TCCAGGTGCC | 1380 |
| CAAATAATGG CAATAAGAGT TCTTAGGAGT GATGGACGGG GTAGCATGTG GGATATTATA | 1440 |
| GAAGGTATGA CATACGCAGC AACCCATGGT GCAGACGTTA TAAGCATGAG TCTCGGTGGA | 1500 |
| AATGCTCCAT ACTTAGATGG TACTGATCCA GAAAGCGTTG CTGTGGATGA GCTTACCGAA | 1560 |
| AAGTACGGTG TTGTATTCGT AATAGCTGCA GGAAATGAAG GTCCTGGCAT TAACATCGTT | 1620 |
| GGAAGTCCTG GTGTTGCAAC AAAGGCAATA ACTGTTGGAG CTGCTGCAGT GCCCATTAAC | 1680 |
| GTTGGAGTTT ATGTTTCCCA AGCACTTGGA TATCCTGATT ACTATGGATT CTATTACTTC | 1740 |
| CCCGCCTACA CAAACGTTAG AATAGCATTC TTCTCAAGCA GAGGGCCGAG AATAGATGGT | 1800 |
| GAAATAAAAC CCAATGTAGT GGCTCCAGGT TACGGAATTT ACTCATCCCT GCCGATGTGG | 1860 |

```
ATTGGCGGAG CTGACTTCAT GTCTGGAACT TCGATGGCTA CTCCACATGT CAGCGGTGTC    1920

GTTGCACTCC TCATAAGCGG GGCAAAGGCC GAGGGAATAT ACTACAATCC AGATATAATT    1980

AAGAAGGTTC TTGAGAGCGG TGCAACCTGG CTTGAGGGAG ATCCATATAC TGGGCAGAAG    2040

TACACTGAGC TTGACCAAGG TCATGGTCTT GTTAACGTTA CCAAGTCCTG GAAATCCTT    2100

AAGGCTATAA ACGGCACCAC TCTCCCAATT GTTGATCACT GGGCAGACAA GTCCTACAGC    2160

GACTTTGCGG AGTACTTGGG TGTGGACGTT ATAAGAGGTC TCTACGCAAG GAACTCTATA    2220

CCTGACATTG TCGAGTGGCA CATTAAGTAC GTAGGGGACA CGGAGTACAG AACTTTTGAG    2280

ATCTATGCAA CTGAGCCATG GATTAAGCCT TTTGTCAGTG GAAGTGTAAT TCTAGAGAAC    2340

AATACCGAGT TTGTCCTTAG GGTGAAATAT GATGTAGAGG GTCTTGAGCC AGGTCTCTAT    2400

GTTGGAAGGA TAATCATTGA TGATCCAACA ACGCCAGTTA TTGAAGACGA GATCTTGAAC    2460

ACAATTGTTA TTCCCGAGAA GTTCACTCCT GAGAACAATT ACACCCTCAC CTGGTATGAT    2520

ATTAATGGTC CAGAAATGGT GACTCACCAC TTCTTCACTG TGCCTGAGGG AGTGGACGTT    2580

CTCTACGCGA TGACCACATA CTGGGACTAC GGTCTGTACA GACCAGATGG AATGTTTGTG    2640

TTCCCATACC AGCTAGATTA TCTTCCCGCT GCAGTCTCAA ATCCAATGCC TGGAAACTGG    2700

GAGCTAGTAT GGACTGGATT TAACTTTGCA CCCCTCTATG AGTCGGGCTT CCTTGTAAGG    2760

ATTTACGGAG TAGAGATAAC TCCAAGCGTT TGGTACATTA ACAGGACATA CCTTGACACT    2820

AACACTGAAT TCTCAATTGA ATTCAATATT ACTAACATCT ATGCCCCAAT TAATGCAACT    2880

CTAATCCCCA TTGGCCTTGG AACCTACAAT GCGAGCGTTG AAAGCGTTGG TGATGGAGAG    2940

TTCTTCATAA AGGGCATTGA AGTTCCTGAA GGCACCGCAG AGTTGAAGAT TAGGATAGGC    3000

AACCCAAGTG TTCCGAATTC AGATCTAGAC TTGTACCTTT ATGACAGTAA AGGCAATTTA    3060

GTGGCCTTAG ATGGAAACCC AACAGCAGAA GAAGAGGTTG TAGTTGAGTA TCCTAAGCCT    3120

GGAGTTTATT CAATAGTAGT ACATGGTTAC AGCGTCAGGG ACGAAAATGG TAATCCAACG    3180

ACAACCACCT TTGACTTAGT TGTTCAAATG ACCCTTGATA ATGGAAACAT AAAGCTTGAC    3240

AAAGACTCGA TTATTCTTGG AAGCAATGAA AGCGTAGTTG TAACTGCAAA CATAACAATT    3300

GATAGAGATC ATCCTACAGG AGTATACTCT GGTATCATAG AGATTAGAGA TAATGAGGTC    3360

TACCAGGATA CAAATACTTC AATTGCGAAA ATACCCATAA CTTTGGTAAT TGACAAGGCG    3420

GACTTTGCCG TTGGTCTCAC ACCAGCGAGG GGAGTACTTG GAGAGGCTAG AAATTACACT    3480

CTAATTGTAA AGCATGCCCT AACACTAGAG CCTGTGCCAA ATGCTACAGT GATTATAGGA    3540

AACTACACCT ACCTCACAGA CGAAAACGGT ACAGTGACAT TCACGTATGC TCCAACTAAG    3600

TTAGGCAGTG ATGAAATCAC AGTCATAGTT AAGAAAGAGA ACTTCAACAC ATTAGAGAAG    3660

ACCTTCCAAA TCACAGTATC AGAGCCTGAA ATAACTGAAG AGGACATAAA TGAGCCCAAG    3720

CTTGCAATGT CATCACCAGA AGCAAATGCT ACCATAGTAT CAGTTGAGAT GGAGAGTGAG    3780

GGTGGCGTTA AAAAGACAGT GACAGTGGAA ATAACTATAA ACGGAACCGC TAATGAGACT    3840

GCAACAATAG TGGTTCCTGT TCCTAAGAAG GCCGAAAACA TCGAGGTAAG TGGAGACCAC    3900

GTAATTTCCT ATAGTATAGA GGAAGGAGAG TACGCCAAGT ACGTTATAAT TACAGTGAAG    3960

TTTGCATCAC CTGTAACAGT AACTGTTACT TACACTATCT ATGCTGGCCC AAGAGTCTCA    4020

ATCTTGACAC TTAACTTCCT TGGCTACTCA TGGTACAGAC TATATTCACA GAAGTTTGAC    4080

GAATTGTACC AAAAGGCCCT TGAATTGGGA GTGGACAACG AGACATTAGC TTTAGCCCTC    4140

AGCTACCATG AAAAAGCCAA AGAGTACTAC GAAAAGGCCC TTGAGCTTAG CGAGGGTAAC    4200
```

```
ATAATCCAAT ACCTTGGAGA CATAAGACTA TTACCTCCAT TAAGACAGGC ATACATCAAT    4260

GAAATGAAGG CAGTTAAGAT ACTGGAAAAG GCCATAGAAG AATTAGAGGG TGAAGAGTAA    4320

TCTCCAATTT TTCCCACTTT TTCTTTTATA ACATTCCAAG CCTTTTCTTA GCTTCTTCGC    4380

TCATTCTATC AGGAGTCCAT GGAGGATCAA AGGTAAGTTC AACCTCCACA TCTCTTACTC    4440

CTGGGATTTC GAGTACTTTC TCCTCTACAG CTCTAAGAAG CCAGAGAGTT AAAGGACACC    4500

CAGGAGTTGT CATTGTCATC TTTATATATA CCGTTTTGTC AGGATTAATC TTTAGCTCAT    4560

AAATTAATCC AAGGTTTACA ACATCCATCC CAATTTCTGG GTCGATAACC TCCTTTAGCT    4620

TTTCCAGAAT CATTTCTTCA GTAATTTCAA GGTTCTCATC TTTGGTTTCT CTCACAAACC    4680

CAATTTCAAC CTGCCTGATA CCTTCTAACT CCCTAAGCTT GTTATATATC TCCAAAAGAG    4740

TGGCATCATC AATTTTCTCT TTAAA                                         4765
```

(2) INFORMATION FOR SEQ ID NO: 8:

(i) SEQUENCE CHARACTERISTICS:
        (A) LENGTH: 1398 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Met Asn Lys Lys Gly Leu Thr Val Leu Phe Ile Ala Ile Met Leu
                 5                  10                  15

Leu Ser Val Val Pro Val His Phe Val Ser Ala Glu Thr Pro Pro
                20                  25                  30

Val Ser Ser Glu Asn Ser Thr Thr Ser Ile Leu Pro Asn Gln Gln
                35                  40                  45

Val Val Thr Lys Glu Val Ser Gln Ala Ala Leu Asn Ala Ile Met
                50                  55                  60

Lys Gly Gln Pro Asn Met Val Leu Ile Ile Lys Thr Lys Glu Gly
                65                  70                  75

Lys Leu Glu Glu Ala Lys Thr Glu Leu Glu Lys Leu Gly Ala Glu
                80                  85                  90

Ile Leu Asp Glu Asn Arg Val Leu Asn Met Leu Leu Val Lys Ile
                95                 100                 105

Lys Pro Glu Lys Val Lys Glu Leu Asn Tyr Ile Ser Ser Leu Glu
               110                 115                 120

Lys Ala Trp Leu Asn Arg Glu Val Lys Leu Ser Pro Pro Ile Val
               125                 130                 135

Glu Lys Asp Val Lys Thr Lys Glu Pro Ser Leu Glu Pro Lys Met
               140                 145                 150

Tyr Asn Ser Thr Trp Val Ile Asn Ala Leu Gln Phe Ile Gln Glu
               155                 160                 165

Phe Gly Tyr Asp Gly Ser Gly Val Val Ala Val Leu Asp Thr
               170                 175                 180

Gly Val Asp Pro Asn His Pro Phe Leu Ser Ile Thr Pro Asp Gly
               185                 190                 195

Arg Arg Lys Ile Ile Glu Trp Lys Asp Phe Thr Asp Glu Gly Phe
               200                 205                 210

Val Asp Thr Ser Phe Ser Phe Ser Lys Val Val Asn Gly Thr Leu
               215                 220                 225

Ile Ile Asn Thr Thr Phe Gln Val Ala Ser Gly Leu Thr Leu Asn
```

```
                          230                 235                 240
Glu Ser Thr Gly Leu Met Glu Tyr Val Val Lys Thr Val Tyr Val
                      245                 250                 255
Ser Asn Val Thr Ile Gly Asn Ile Thr Ser Ala Asn Gly Ile Tyr
                      260                 265                 270
His Phe Gly Leu Leu Pro Glu Arg Tyr Phe Asp Leu Asn Phe Asp
                      275                 280                 285
Gly Asp Gln Glu Asp Phe Tyr Pro Val Leu Leu Val Asn Ser Thr
                      290                 295                 300
Gly Asn Gly Tyr Asp Ile Ala Tyr Val Asp Thr Asp Leu Asp Tyr
                      305                 310                 315
Asp Phe Thr Asp Glu Val Pro Leu Gly Gln Tyr Asn Val Thr Tyr
                      320                 325                 330
Asp Val Ala Val Phe Ser Tyr Tyr Gly Pro Leu Asn Tyr Val
                      335                 340                 345
Leu Ala Glu Ile Asp Pro Asn Gly Glu Tyr Ala Val Phe Gly Trp
                      350                 355                 360
Asp Gly His Gly His Gly Thr His Val Ala Gly Thr Val Ala Gly
                      365                 370                 375
Tyr Asp Ser Asn Asn Asp Ala Trp Asp Trp Leu Ser Met Tyr Ser
                      380                 385                 390
Gly Glu Trp Glu Val Phe Ser Arg Leu Tyr Gly Trp Asp Tyr Thr
                      395                 400                 405
Asn Val Thr Thr Asp Thr Val Gln Gly Val Ala Pro Gly Ala Gln
                      410                 415                 420
Ile Met Ala Ile Arg Val Leu Arg Ser Asp Gly Arg Gly Ser Met
                      425                 430                 435
Trp Asp Ile Ile Glu Gly Met Thr Tyr Ala Ala Thr His Gly Ala
                      440                 445                 450
Asp Val Ile Ser Met Ser Leu Gly Gly Asn Ala Pro Tyr Leu Asp
                      455                 460                 465
Gly Thr Asp Pro Glu Ser Val Ala Val Asp Glu Leu Thr Glu Lys
                      470                 475                 480
Tyr Gly Val Val Phe Val Ile Ala Ala Gly Asn Glu Gly Pro Gly
                      485                 490                 495
Ile Asn Ile Val Gly Ser Pro Gly Val Ala Thr Lys Ala Ile Thr
                      500                 505                 510
Val Gly Ala Ala Ala Val Pro Ile Asn Val Gly Val Tyr Val Ser
                      515                 520                 525
Gln Ala Leu Gly Tyr Pro Asp Tyr Tyr Gly Phe Tyr Tyr Phe Pro
                      530                 535                 540
Ala Tyr Thr Asn Val Arg Ile Ala Phe Phe Ser Ser Arg Gly Pro
                      545                 550                 555
Arg Ile Asp Gly Glu Ile Lys Pro Asn Val Val Ala Pro Gly Tyr
                      560                 565                 570
Gly Ile Tyr Ser Ser Leu Pro Met Trp Ile Gly Ala Asp Phe
                      575                 580                 585
Met Ser Gly Thr Ser Met Ala Thr Pro His Val Ser Gly Val Val
                      590                 595                 600
Ala Leu Leu Ile Ser Gly Ala Lys Ala Glu Gly Ile Tyr Tyr Asn
                      605                 610                 615
Pro Asp Ile Ile Lys Lys Val Leu Glu Ser Gly Ala Thr Trp Leu
                      620                 625                 630
```

```
Glu Gly Asp Pro Tyr Thr Gly Gln Lys Tyr Thr Glu Leu Asp Gln
            635                 640                 645

Gly His Gly Leu Val Asn Val Thr Lys Ser Trp Glu Ile Leu Lys
            650                 655                 660

Ala Ile Asn Gly Thr Thr Leu Pro Ile Val Asp His Trp Ala Asp
            665                 670                 675

Lys Ser Tyr Ser Asp Phe Ala Glu Tyr Leu Gly Val Asp Val Ile
            680                 685                 690

Arg Gly Leu Tyr Ala Arg Asn Ser Ile Pro Asp Ile Val Glu Trp
            695                 700                 705

His Ile Lys Tyr Val Gly Asp Thr Glu Tyr Arg Thr Phe Glu Ile
            710                 715                 720

Tyr Ala Thr Glu Pro Trp Ile Lys Pro Phe Val Ser Gly Ser Val
            725                 730                 735

Ile Leu Glu Asn Asn Thr Glu Phe Val Leu Arg Val Lys Tyr Asp
            740                 745                 750

Val Glu Gly Leu Glu Pro Gly Leu Tyr Val Gly Arg Ile Ile Ile
            755                 760                 765

Asp Asp Pro Thr Thr Pro Val Ile Glu Asp Glu Ile Leu Asn Thr
            770                 775                 780

Ile Val Ile Pro Glu Lys Phe Thr Pro Glu Asn Asn Tyr Thr Leu
            785                 790                 795

Thr Trp Tyr Asp Ile Asn Gly Pro Glu Met Val Thr His His Phe
            800                 805                 810

Phe Thr Val Pro Glu Gly Val Asp Val Leu Tyr Ala Met Thr Thr
            815                 820                 825

Tyr Trp Asp Tyr Gly Leu Tyr Arg Pro Asp Gly Met Phe Val Phe
            830                 835                 840

Pro Tyr Gln Leu Asp Tyr Leu Pro Ala Ala Val Ser Asn Pro Met
            845                 850                 855

Pro Gly Asn Trp Glu Leu Val Trp Thr Gly Phe Asn Phe Ala Pro
            860                 865                 870

Leu Tyr Glu Ser Gly Phe Leu Val Arg Ile Tyr Gly Val Glu Ile
            875                 880                 885

Thr Pro Ser Val Trp Tyr Ile Asn Arg Thr Tyr Leu Asp Thr Asn
            890                 895                 900

Thr Glu Phe Ser Ile Glu Phe Asn Ile Thr Asn Ile Tyr Ala Pro
            905                 910                 915

Ile Asn Ala Thr Leu Ile Pro Ile Gly Leu Gly Thr Tyr Asn Ala
            920                 925                 930

Ser Val Glu Ser Val Gly Asp Gly Glu Phe Phe Ile Lys Gly Ile
            935                 940                 945

Glu Val Pro Glu Gly Thr Ala Glu Leu Lys Ile Arg Ile Gly Asn
            950                 955                 960

Pro Ser Val Pro Asn Ser Asp Leu Asp Leu Tyr Leu Tyr Asp Ser
            965                 970                 975

Lys Gly Asn Leu Val Ala Leu Asp Gly Asn Pro Thr Ala Glu Glu
            980                 985                 990

Glu Val Val Val Glu Tyr Pro Lys Pro Gly Val Tyr Ser Ile Val
            995                1000                1005

Val His Gly Tyr Ser Val Arg Asp Glu Asn Gly Asn Pro Thr Thr
           1010                1015                1020
```

```
Thr Thr Phe Asp Leu Val Val Gln Met Thr Leu Asp Asn Gly Asn
                1025                1030                1035

Ile Lys Leu Asp Lys Asp Ser Ile Ile Leu Gly Ser Asn Glu Ser
                1040                1045                1050

Val Val Val Thr Ala Asn Ile Thr Ile Asp Arg Asp His Pro Thr
                1055                1060                1065

Gly Val Tyr Ser Gly Ile Ile Glu Ile Arg Asp Asn Glu Val Tyr
                1070                1075                1080

Gln Asp Thr Asn Thr Ser Ile Ala Lys Ile Pro Ile Thr Leu Val
                1085                1090                1095

Ile Asp Lys Ala Asp Phe Ala Val Gly Leu Thr Pro Ala Glu Gly
                1100                1105                1110

Val Leu Gly Glu Ala Arg Asn Tyr Thr Leu Ile Val Lys His Ala
                1115                1120                1125

Leu Thr Leu Glu Pro Val Pro Asn Ala Thr Val Ile Ile Gly Asn
                1130                1135                1140

Tyr Thr Tyr Leu Thr Asp Glu Asn Gly Thr Val Thr Phe Thr Tyr
                1145                1150                1155

Ala Pro Thr Lys Leu Gly Ser Asp Glu Ile Thr Val Ile Val Lys
                1160                1165                1170

Lys Glu Asn Phe Asn Thr Leu Glu Lys Thr Phe Gln Ile Thr Val
                1175                1180                1185

Ser Glu Pro Glu Ile Thr Glu Glu Asp Ile Asn Glu Pro Lys Leu
                1190                1195                1200

Ala Met Ser Ser Pro Glu Ala Asn Ala Thr Ile Val Ser Val Glu
                1205                1210                1215

Met Glu Ser Glu Gly Gly Val Lys Lys Thr Val Thr Val Glu Ile
                1220                1225                1230

Thr Ile Asn Gly Thr Ala Asn Glu Thr Ala Thr Ile Val Val Pro
                1235                1240                1245

Val Pro Lys Lys Ala Glu Asn Ile Glu Val Ser Gly Asp His Val
                1250                1255                1260

Ile Ser Tyr Ser Ile Glu Glu Gly Glu Tyr Ala Lys Tyr Val Ile
                1265                1270                1275

Ile Thr Val Lys Phe Ala Ser Pro Val Thr Val Thr Val Thr Tyr
                1280                1285                1290

Thr Ile Tyr Ala Gly Pro Arg Val Ser Ile Leu Thr Leu Asn Phe
                1295                1300                1305

Leu Gly Tyr Ser Trp Tyr Arg Leu Tyr Ser Gln Lys Phe Asp Glu
                1310                1315                1320

Leu Tyr Gln Lys Ala Leu Glu Leu Gly Val Asp Asn Glu Thr Leu
                1325                1330                1335

Ala Leu Ala Leu Ser Tyr His Glu Lys Ala Lys Glu Tyr Tyr Glu
                1340                1345                1350

Lys Ala Leu Glu Leu Ser Glu Gly Asn Ile Ile Gln Tyr Leu Gly
                1355                1360                1365

Asp Ile Arg Leu Leu Pro Pro Leu Arg Gln Ala Tyr Ile Asn Glu
                1370                1375                1380

Met Lys Ala Val Lys Ile Leu Glu Lys Ala Ile Glu Glu Leu Glu
                1385                1390                1395

Gly Glu Glu (2) INFORMATION FOR SEQ ID NO: 9:
```

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 9:

GGWWSDRRTG TTRRHGTHGC DGTDMTYGAC ACBGG                          35

(2) INFORMATION FOR SEQ ID NO: 10:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 10:

KSTCACGGAA CTCACGTDGC BGGMACDGTT GC                             32

(2) INFORMATION FOR SEQ ID NO: 11:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 11:

ASCMGCAACH GTKCCVGCHA CGTGAGTTCC GTG                            33

(2) INFORMATION FOR SEQ ID NO: 12:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 12:

CHCCGSYVAC RTGBGGAGWD GCCATBGAVG TDCC                           34

(2) INFORMATION FOR SEQ ID NO: 13:

(i) SEQUENCE CHARACTERISTICS:
        (A) LENGTH: 145 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 13:

A GTT GCG GTA ATT GAC ACG GGT ATA GAC GCG AAC CAC CCC GAT CTG   46
  Val Ala Val Ile Asp Thr Gly Ile Asp Ala Asn His Pro Asp Leu
              5                  10                  15

AAG GGC AAG GTC ATA GGC TGG TAC GAC GCC GTC AAC GGC AGG TCG   91
  Lys Gly Lys Val Ile Gly Trp Tyr Asp Ala Val Asn Gly Arg Ser
          20                  25                  30

```
ACC CCC TAC GAT GAC CAG GGA CAC GGA ACT CAC GTN GCN GGA ACN        136
Thr Pro Tyr Asp Asp Gln Gly His Gly Thr His Val Ala Gly Thr
             35                  40                  45

GTT GCT GGT                                                         145
Val Ala Gly
```

(2) INFORMATION FOR SEQ ID NO: 14:

(i) SEQUENCE CHARACTERISTICS:
        (A) LENGTH: 564 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 14:

```
TCT CAC GGA ACT CAC GTG GCG GGA ACA GTT GCC GGA ACA GGC AGC         45
Ser His Gly Thr His Val Ala Gly Thr Val Ala Gly Thr Gly Ser
              5                  10                  15

GTT AAC TCC CAG TAC ATA GGC GTC GCC CCC GGC GCG AAG CTC GTC         90
Val Asn Ser Gln Tyr Ile Gly Val Ala Pro Gly Ala Lys Leu Val
             20                  25                  30

GGT GTC AAG GTT CTC GGT GCC GAC GGT TCG GGA AGC GTC TCC ACC        135
Gly Val Lys Val Leu Gly Ala Asp Gly Ser Gly Ser Val Ser Thr
             35                  40                  45

ATC ATC GCG GGT GTT GAC TGG GTC GTC CAG AAC AAG GAT AAG TAC        180
Ile Ile Ala Gly Val Asp Trp Val Val Gln Asn Lys Asp Lys Tyr
             50                  55                  60

GGG ATA AGG GTC ATC AAC CTC TCC CTC GGC TCC TCC CAG AGC TCC        225
Gly Ile Arg Val Ile Asn Leu Ser Leu Gly Ser Ser Gln Ser Ser
             65                  70                  75

GAC GGA GCC GAC TCC CTC AGT CAG GCC GTC AAC AAC GCC TGG GAC        270
Asp Gly Ala Asp Ser Leu Ser Gln Ala Val Asn Asn Ala Trp Asp
             80                  85                  90

GCC GGT ATA GTA GTC TGC GTC GCC GCC GGC AAC AGC GGG CCG AAC        315
Ala Gly Ile Val Val Cys Val Ala Ala Gly Asn Ser Gly Pro Asn
             95                 100                 105

ACC TAC ACC GTC GGC TCA CCC GCC GCC GCG AGC AAG GTC ATA ACC        360
Thr Tyr Thr Val Gly Ser Pro Ala Ala Ala Ser Lys Val Ile Thr
            110                 115                 120

GTC GGT GCA GTT GAC AGC AAC GAC AAC ATC GCC AGC TTC TCC AGC        405
Val Gly Ala Val Asp Ser Asn Asp Asn Ile Ala Ser Phe Ser Ser
            125                 130                 135

AGG GGA CCG ACC GCG GAC GGA AGG CTC AAG CCG GAA GTC GTC GCC        450
Arg Gly Pro Thr Ala Asp Gly Arg Leu Lys Pro Glu Val Val Ala
            140                 145                 150

CCC GGC GTT GAC ATC ATA GCC CCG CGC GCC AGC GGA ACC AGC ATG        495
Pro Gly Val Asp Ile Ile Ala Pro Arg Ala Ser Gly Thr Ser Met
            155                 160                 165

GGC ACC CCG ATA AAC GAC TAC TAC ACC AAG GCC TCT GGA ACC TCA        540
Gly Thr Pro Ile Asn Asp Tyr Tyr Thr Lys Ala Ser Gly Thr Ser
            170                 175                 180

ATG GCC ACT CCC CAT GTT ACC GGT                                    564
Met Ala Thr Pro His Val Thr Gly
            185
```

(2) INFORMATION FOR SEQ ID NO: 15:

(i) SEQUENCE CHARACTERISTICS:
        (A) LENGTH: 1859 base pairs
        (B) TYPE: nucleic acid
        (C) STRANDEDNESS: double (D) TOPOLOGY: linear (ii) MOLECULE TYPE: genomic DNA (xi) SEQUENCE DESCRIPTION: SEQ ID NO: 15:

| | | | | | |
|---|---|---|---|---|---|
| GAGCTCCGAC | GGAACCGACT | CCCTCAGTCA | GGCCGTCAAC | AACGCCTGGG | ACGCCGGTAT | 60 |
| AGTAGTCTGC | GTCGCCGCCG | GCAACAGCGG | GCCGAACACC | TACACCGTCG | GCTCACCCGC | 120 |
| CGCCGCGAGC | AAGGTCATAA | CCGTCGGTGC | AGTTGACAGC | AACGACAACA | TCGCCAGCTT | 180 |
| CTCCAGCAGG | GGACCGACCG | CGGACGGAAG | GCTCAAGCCG | GAAGTCGTCG | CCCCCGGCGT | 240 |
| TGACATCATA | GCCCCGCGCG | CCAGCGGAAC | CAGCATGGGC | ACCCCGATAA | ACGACTACTA | 300 |
| CACCAAGGCC | TCTGGAACCA | GCATGGCCAC | CCCGCACGTT | TCGGGCGTTG | GCGCGCTCAT | 360 |
| CCTCCAGGCC | CACCCGAGCT | GGACCCCGGA | CAAGGTGAAG | ACCGCCCTCA | TCGAGACCGC | 420 |
| CGACATAGTC | GCCCCCAAGG | AGATAGCGGA | CATCGCCTAC | GGTGCGGGTA | GGGTGAACGT | 480 |
| CTACAAGGCC | ATCAAGTACG | ACGACTACGC | CAAGCTCACC | TTCACCGGCT | CCGTCGCCGA | 540 |
| CAAGGGAAGC | GCCACCCACA | CCTTCGACGT | CAGCGGCGCC | ACCTTCGTGA | CCGCCACCCT | 600 |
| CTACTGGGAC | ACGGGCTCGA | GCGACATCGA | CCTCTACCTC | TACGACCCCA | ACGGGAACGA | 660 |
| GGTTGACTAC | TCCTACACCG | CCTACTACGG | CTTCGAGAAG | GTCGGCTACT | ACAACCCGAC | 720 |
| CGCCGGAACC | TGGACGGTCA | AGGTCGTCAG | CTACAAGGGC | GCGGCGAACT | ACCAGGTCGA | 780 |
| CGTCGTCAGC | GACGGGAGCC | TCAGCCAGTC | CGGCGGCGGC | AACCCGAATC | CAAACCCCAA | 840 |
| CCCGAACCCA | ACCCCGACCA | CCGACACCCA | GACCTTCACC | GGTTCCGTTA | ACGACTACTG | 900 |
| GGACACCAGC | GACACCTTCA | CCATGAACGT | CAACAGCGGT | GCCACCAAGA | TAACCGGTGA | 960 |
| CCTGACCTTC | GATACTTCCT | ACAACGACCT | CGACCTCTAC | CTCTACGACC | CCAACGGCAA | 1020 |
| CCTCGTTGAC | AGGTCCACGT | CGAGCAACAG | CTACGAGCAC | GTCGAGTACG | CCAACCCCGC | 1080 |
| CCCGGGAACC | TGGACGTTCC | TCGTCTACGC | CTACAGCACC | TACGGCTGGG | CGGACTACCA | 1140 |
| GCTCAAGGCC | GTCGTCTACT | ACGGGTGAAG | GTTTTTAATC | CCCTTTTCTT | TCCCCTTTTG | 1200 |
| AGGTGGTTGG | GATGAAGCGG | GTTCTTGCGG | CGATCCTTGT | AATCATGCTC | ATCGGATTAT | 1260 |
| CATTCCCTGC | CGGAAGTGCT | AAAATCGAGC | CCTACGTTTA | CAGCCCCACC | GTTCCGGATA | 1320 |
| CCGCCTTCGC | GGTTCTCACC | CTGTACAGGA | CCGGGGACTA | CGCCCGGGTT | CTCGAGGGAT | 1380 |
| ACGAGTGGCT | CCTCCAGATG | AGAACTCCCA | TCGATTCGTG | GGGGGTTTCC | CGCGGGGAAA | 1440 |
| CGCACATGGC | CAAGTACACG | GCAATGGCGA | TGCTGGCCCT | CATGCGCGGC | GAGAACGTGG | 1500 |
| CGAGGGGGCG | TTACAGGGAT | GTTCTCAACG | ACGCCGCGTA | CTGGTTAATA | TACAAACAGA | 1560 |
| ACCCGGACGG | CTCGTGGGAG | GACTACACCG | GAACGGCGCT | GGCCGTCATC | GCGCTCGGGG | 1620 |
| AGTTCCTTAA | GGGCGGGTAC | ATCAACGCGA | ACCTGACCGG | CTTCAAAAAG | CAGGTTAAAG | 1680 |
| AGGCCGTAAA | CCGCGGGGAA | GGCTGGCTGA | TGGATGCGGA | CCCAAAAACG | GACGCGGATA | 1740 |
| GAATATTCGG | CTACCTCGCC | CTCGGTAAAA | AGGACGAACT | CAAAAAGATG | AACCCTTCCG | 1800 |
| GTGACCTGAA | GGCCTACCGC | GCCTTTGCAC | TTGCCTACCT | CGGGGAGAGG | GTCGAGCTC | 1859 |

(2) INFORMATION FOR SEQ ID NO: 16:

(i) SEQUENCE CHARACTERISTICS:
          (A) LENGTH: 20 base pairs
          (B) TYPE: nucleic acid
          (C) STRANDEDNESS: double
          (D) TOPOLOGY: linear (ii) MOLECULE TYPE: genomic DNA (xi) SEQUENCE DESCRIPTION: SEQ ID NO: 16:

TGTAGTAGTC GTTTATCGGG                                              20

(2) INFORMATION FOR SEQ ID NO: 17:

(i) SEQUENCE CHARACTERISTICS:
        (A) LENGTH: 1464 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 17:

AAGCTTAACA TCGAGCGCTC CACCTCTAAA GTAGGTGAGT GTGGATACGA AGGTTAGGGC    60

CGCTATGACG ACCTTCAGGA TCCCAACGGC TTCTTTTATG GGGAGCCCGG CGAAGGTGAG   120

AATTGAAAGG ATTACCATAC TCCCTCCGCT CATCATGGAG CCTATGAATC CCCCTCCAAA   180

AGAGAGAAGT GCTATAAGGA GCGTCCTCAT GTTCCATGCT ATGTTTTGGT ATTTAATGCT   240

TTTCCGCTTA ATGTTACACC TCCTCATGAC AATTTCGCGT TTAGGGATGG GGTTAATTGG   300

ACCCCTCCGA GCCACGGGTT GATGTCCATT ATGTCGATAT TCACCATCTT ATCCCCAACT   360

TTGTGGGTTT CAAACATTAC CCTACGTTAT ATTTTTATCG TCCTAATTAA CTGCTGAAAC   420

GGGCGCTTAT CGTTCATCGT TGATGGTTTT GGGTGACCGG GCATTAAGGA ATTGTGTCGT   480

TTGCTGAAAT TTATGAAACG GAGTTGGCTT CTTTATGTTA CATAAAGATG TACATTACTG   540

TAATGTATAT AAATGGAAGA AACACTGTTG CGTAAACTTT TTAATGTATC CAATATCAGT   600

ACTTCGATGT CCCGATATGG GACATGTTGG ATAGGAGGGT ACTGGAATGA AGAGGTTAGG   660

TGCTGTGGTG CTGGCACTGG TGCTCGTGGG TCTTCTGGCC GGAACGGCCC TTGCGGCACC   720

CGTAAAACCG GTTGTCAGGA ACAACGCGGT TCAGCAGAAG AACTACGGAC TGCTGACCCC   780

GGGACTGTTC AAGAAAGTCC AGAGGATGAA CTGGAACCAG GAAGTGGACA CCGTCATAAT   840

GTTCGGGAGC TACGGAGACA GGGACAGGGC GGTTAAGGTA CTGAGGCTCA TGGGCGCCCA   900

GGTCAAGTAC TCCTACAAGA TAATCCCTGC TGTCGCGGTT AAAATAAAGG CCAGGGACCT   960

TCTGCTGATC GCGGGCATGA TAGACACGGG TTACTTCGGT AACACAAGGG TCTCGGGCAT  1020

AAAGTTCATA CAGGAGGATT ACAAGGTTCA GGTTGACGAC GCCACTTCCG TCTCCCAGAT  1080

AGGGGCCGAT ACCGTCTGGA ACTCCCTCGG CTACGACGGA AGCGGTGTGG TGGTTGCCAT  1140

CGTCGATACG GGTATAGACG CGAACCACCC CGATCTGAAG GGCAAGGTCA TAGGCTGGTA  1200

CGACTCCGTC AACGGCAGGT CGACCCCCTA CGATGACCAG GGACACGGAA CCCACGTTGC  1260

GGGTATCGTT GCCGGAACCG GGAGCGTTAA CTCCCAGTAC ATAGGCGTCG GCCCCGGCGC  1320

GAAGCTCGTC GGCGTCAAGG TTCTCGGTTC CGACGGTTCG GGAAGCGTCT CCACCATCAT  1380

CGCGGGTGTT GACTGGAACG TCCAGAACTA GGACAAGTAC GGGATAAGGG TCATCAACCT  1440

CTCCCTCGGC TCCTCCCAGA GCTC                                       1464

(2) INFORMATION FOR SEQ ID NO: 18:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 18:

AAAAGAATTC GGATCCATGA AGAGGTTAGG TGC                                33

(2) INFORMATION FOR SEQ ID NO: 19:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 19:

TTTTATCGAT CAGGCGTCCC AGGCGTTG                                      28

(2) INFORMATION FOR SEQ ID NO: 20:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 20:

CATTATAGGT AAGAGAGGAA TG                                            22

(2) INFORMATION FOR SEQ ID NO: 21:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 21:

GATCCATTCC TCTCTTACCT ATAATGGTAC                                    30

(2) INFORMATION FOR SEQ ID NO: 22:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 22:

TAGCAGTAAT TGACACGGG                                                19

(2) INFORMATION FOR SEQ ID NO: 23:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 23:

TAGCAGTAAT TGACACTGG                                                19

(2) INFORMATION FOR SEQ ID NO: 24:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 24:

```
CTGTTCCAGC TACGTGAGTT CC                                          22
```

(2) INFORMATION FOR SEQ ID NO: 25:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 25:

```
CTGTTCCAGC TACATGAGTT CC                                          22
```

(2) INFORMATION FOR SEQ ID NO: 26:

(i) SEQUENCE CHARACTERISTICS:
        (A) LENGTH: 507 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 26:

```
A CTA GTC ATC TCA GGT TTA ACA GGG GGT AAA GCT AAG CTT TCA GGT        46
  Leu Val Ile Ser Gly Leu Thr Gly Gly Lys Ala Lys Leu Ser Gly
                    5                  10                  15

GTT AGG TTT ATC CAG GAA GAC TAC AAA GTT ACA GTT TCA GCA GAA          91
Val Arg Phe Ile Gln Glu Asp Tyr Lys Val Thr Val Ser Ala Glu
                20                  25                  30

TTA GAA GGA CTG GAT GAG TCT GCA GCT CAA GTT ATG GCA ACT TAC         136
Leu Glu Gly Leu Asp Glu Ser Ala Ala Gln Val Met Ala Thr Tyr
            35                  40                  45

GTT TGG AAC TTG GGA TAT GAT GGT TCT GGA ATC ACA ATA GGA ATA         181
Val Trp Asn Leu Gly Tyr Asp Gly Ser Gly Ile Thr Ile Gly Ile
            50                  55                  60

ATT GAC ACT GGA ATT GAC GCT TCT CAT CCA GAT CTC CAA GGA AAA         226
Ile Asp Thr Gly Ile Asp Ala Ser His Pro Asp Leu Gln Gly Lys
                65                  70                  75

GTA ATT GGG TGG GTA GAT TTT GTC AAT GGT AGG AGT TAT CCA TAC         271
Val Ile Gly Trp Val Asp Phe Val Asn Gly Arg Ser Tyr Pro Tyr
                80                  85                  90

GAT GAC CAT GGA CAT GGA ACT CAT GTA GCT TCA ATA GCA GCT GGT         316
Asp Asp His Gly His Gly Thr His Val Ala Ser Ile Ala Ala Gly
                95                 100                 105

ACT GGA GCA GCA AGT AAT GGC AAG TAC AAG GGA ATG GCT CCA GGA         361
Thr Gly Ala Ala Ser Asn Gly Lys Tyr Lys Gly Met Ala Pro Gly
               110                 115                 120

GCT AAG CTG GCG GGA ATT AAG GTT CTA GGT GCC GAT GGT TCT GGA         406
Ala Lys Leu Ala Gly Ile Lys Val Leu Gly Ala Asp Gly Ser Gly
               125                 130                 135

AGC ATA TCT ACT ATA ATT AAG GGA GTT GAG TGG GCC GTT GAT AAC         451
```

```
Ser Ile Ser Thr Ile Ile Lys Gly Val Glu Trp Ala Val Asp Asn
            140                 145                 150

AAA GAT AAG TAC GGA ATT AAG GTC ATT AAT CTT TCT CTT GGT TCA        496
Lys Asp Lys Tyr Gly Ile Lys Val Ile Asn Leu Ser Leu Gly Ser
            155                 160                 165

AGC CAG AGC TC                                                     507
Ser Gln Ser
```

(2) INFORMATION FOR SEQ ID NO: 27:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 27:

TGACACTGGA ATTGACGCTT CTCATCCAGA                                   30

(2) INFORMATION FOR SEQ ID NO: 28:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 28:

TCTCCAAGGA AAAGTAATTG GGTGGGTAGA                                   30

(2) INFORMATION FOR SEQ ID NO: 29:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 29:

GTTGCCATAA CTTGAGCTGC AGACTCATCC                                   30

(2) INFORMATION FOR SEQ ID NO: 30:

(i) SEQUENCE CHARACTERISTICS:
        (A) LENGTH: 419 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 30:

```
TTTATTAAGC ATAAAATAGC CATGCAACTT TGATCACTAA TGTGCGGTGG TGCAC ATG    58
                                                            Met

AAG GGG CTG AAA GCT CTC ATA TTA GTG ATT TTA GTT CTA GGT TTG     103
    Lys Gly Leu Lys Ala Leu Ile Leu Val Ile Leu Val Leu Gly Leu
                 5                  10                  15

GTA GTA GGG AGC GTA GCG GCA GCT CCA GAG AAG AAA GTT GTT CAA     148
    Val Val Gly Ser Val Ala Ala Ala Pro Glu Lys Lys Val Val Gln
                 20                 25                  30
```

```
GTA AGA AAT GTT GAG AAG AAC TAT GGT CTG CTA ACG CCA GGA CTG        193
Val Arg Asn Val Glu Lys Asn Tyr Gly Leu Leu Thr Pro Gly Leu
             35                  40                  45

TTC AGA AAA ATT CCC AAA TTG GAT CCT AAC GAG GGA ATC AGC ACA        238
Phe Arg Lys Ile Pro Lys Leu Asp Pro Asn Glu Gly Ile Ser Thr
         50                  55                  60

GTA ATT GTA TTT GTT AAC CAT AGG GGA AAA GAA ATT GCA GTA AGA        283
Val Ile Val Phe Val Asn His Arg Gly Lys Glu Ile Ala Val Arg
         65                  70                  75

GTT CTT GAG TTA ATG GGT GCC CAA GTT AGG TAT GTG TAC CAT ATT        328
Val Leu Glu Leu Met Gly Ala Gln Val Arg Tyr Val Tyr His Ile
         80                  85                  90

ATA CCC CCA ATA GCT GCC GAT CTT AAG GTT AGA GAC TTA CTA GTC        373
Ile Pro Pro Ile Ala Ala Asp Leu Lys Val Arg Asp Leu Leu Val
         95                 100                 105

ATC TCA GGT TTA ACA GGG GGT GAA ACT AAG CTT TCA GGT GTT AGG T      419
Ile Ser Gly Leu Thr Gly Gly Glu Thr Lys Leu Ser Gly Val Ar
        110                 115                 120
```

(2) INFORMATION FOR SEQ ID NO: 31:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 31:

```
GCTCTAGACT CTGGGAGGAG TAGTTATACT TGATGAAGCC TATTCTGAGT TTTCGGGAAA      60

AAGCTTCATA CCAAAAATCA GTGAGTATGA AAATTTAGTA ATTCTAAGGA CGTTTTCAAA     120

GGCGTTTGGA CTTGCTGGAA TTAGATGTGG ATATATGATA GCAAATGAAA AGATTATAGA     180
```

(2) INFORMATION FOR SEQ ID NO: 32:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 32:

```
AGAGGGATCC ATGAAGGGGC TGAAAGCT                                         28
```

(2) INFORMATION FOR SEQ ID NO: 33:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 33:

```
AGAGGCATGC GCTCTAGACT CTGGGAGAGT                                       30
```

(2) INFORMATION FOR SEQ ID NO: 34:

(i) SEQUENCE CHARACTERISTICS:
        (A) LENGTH: 1962 base pairs (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 34:

| | | | | | |
|---|---|---|---|---|---|
| ATGAAGGGGC | TGAAAGCTCT | CATATTAGTG | ATTTTAGTTC | TAGGTTTGGT | AGTAGGGAGC | 60 |
| GTAGCGGCAG | CTCCAGAGAA | GAAAGTTGAA | CAAGTAAGAA | ATGTTGAGAA | GAACTATGGT | 120 |
| CTGCTAACGC | CAGGACTGTT | CAGAAAAATT | CAAAAATTGA | ATCCTAACGA | GGAAATCAGC | 180 |
| ACAGTAATTG | TATTTGAAAA | CCATAGGGAA | AAAGAAATTG | CAGTAAGAGT | TCTTGAGTTA | 240 |
| ATGGGTGCAA | AAGTTAGGTA | TGTGTACCAT | ATTATACCCG | CAATAGCTGC | CGATCTTAAG | 300 |
| GTTAGAGACT | TACTAGTCAT | CTCAGGTTTA | ACAGGGGGTA | AAGCTAAGCT | TTCAGGTGTT | 360 |
| AGGTTTATCC | AGGAAGACTA | CAAAGTTACA | GTTTCAGCAG | AATTAGAAGG | ACTGGATGAG | 420 |
| TCTGCAGCTC | AAGTTATGGC | AACTTACGTT | TGGAACTTGG | GATATGATGG | TTCTGGAATC | 480 |
| ACAATAGGAA | TAATTGACAC | TGGAATTGAC | GCTTCTCATC | CAGATCTCCA | AGGAAAAGTA | 540 |
| ATTGGGTGGG | TAGATTTTGT | CAATGGTAGG | AGTTATCCAT | ACGATGACCA | TGGACATGGA | 600 |
| ACTCATGTAG | CTTCAATAGC | AGCTGGTACT | GGAGCAGCAA | GTAATGGCAA | GTACAAGGGA | 660 |
| ATGGCTCCAG | GAGCTAAGCT | GGCGGGAATT | AAGGTTCTAG | GTGCCGATGG | TTCTGGAAGC | 720 |
| ATATCTACTA | TAATTAAGGG | AGTTGAGTGG | GCCGTTGATA | ACAAAGATAA | GTACGGAATT | 780 |
| AAGGTCATTA | ATCTTTCTCT | TGGTTCAAGC | CAGAGCTCAG | ATGGTACTGA | CGCTCTAAGT | 840 |
| CAGGCTGTTA | ATGCAGCGTG | GGATGCTGGA | TTAGTTGTTG | TGGTTGCCGC | TGGAAACAGT | 900 |
| GGACCTAACA | AGTATACAAT | CGGTTCTCCA | GCAGCTGCAA | GCAAAGTTAT | TACAGTTGGA | 960 |
| GCCGTTGACA | AGTATGATGT | TATAACAAGC | TTCTCAAGCA | GAGGGCCAAC | TGCAGACGGC | 1020 |
| AGGCTTAAGC | CTGAGGTTGT | TGCTCCAGGA | AACTGGATAA | TTGCTGCCAG | AGCAAGTGGA | 1080 |
| ACTAGCATGG | GTCAACCAAT | TAATGACTAT | TACACAGCAG | CTCCTGGGAC | ATCAATGGCA | 1140 |
| ACTCCTCACG | TAGCTGGTAT | TGCAGCCCTC | TTGCTCCAAG | CACACCCGAG | CTGGACTCCA | 1200 |
| GACAAAGTAA | AAACAGCCCT | CATAGAAACT | GCTGATATCG | TAAAGCCAGA | TGAAATAGCC | 1260 |
| GATATAGCCT | ACGGTGCAGG | TAGGGTTAAT | GCATACAAGG | CTATAAACTA | CGATAACTAT | 1320 |
| GCAAAGCTAG | TGTTCACTGG | ATATGTTGCC | AACAAAGGCA | GCCAAACTCA | CCAGTTCGTT | 1380 |
| ATTAGCGGAG | CTTCGTTCGT | AACTGCCACA | TTATACTGGG | ACAATGCCAA | TAGCGACCTT | 1440 |
| GATCTTTACC | TCTACGATCC | CAATGGAAAC | CAGGTTGACT | ACTCTTACAC | CGCCTACTAT | 1500 |
| GGATTCGAAA | AGGTTGGTTA | TTACAACCCA | ACTGATGGAA | CATGGACAAT | TAAGGTTGTA | 1560 |
| AGCTACAGCG | GAAGTGCAAA | CTATCAAGTA | GATGTGGTAA | GTGATGGTTC | CCTTTCACAG | 1620 |
| CCTGGAAGTT | CACCATCTCC | ACAACCAGAA | CCAACAGTAG | ACGCAAAGAC | GTTCCAAGGA | 1680 |
| TCCGATCACT | ACTACTATGA | CAGGAGCGAC | ACCTTTACAA | TGACCGTTAA | CTCTGGGGCT | 1740 |
| ACAAAGATTA | CTGGAGACCT | AGTGTTTGAC | ACAAGCTACC | ATGATCTTGA | CCTTTACCTC | 1800 |
| TACGATCCTA | ACCAGAAGCT | TGTAGATAGA | TCGGAGAGTC | CCAACAGCTA | CGAACACGTA | 1860 |
| GAATACTTAA | CCCCCGCCCC | AGGAACCTGG | TACTTCCTAG | TATATGCCTA | CTACACTTAC | 1920 |
| GGTTGGGCTT | ACTACGAGCT | GACGGCTAAA | GTTTATTATG | GC | | 1962 |

(2) INFORMATION FOR SEQ ID NO: 35:

(i) SEQUENCE CHARACTERISTICS:
        (A) LENGTH: 654 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO: 35:

```
Met Lys Gly Leu Lys Ala Leu Ile Leu Val Ile Leu Val Leu Gly
                 5                  10                  15
Leu Val Val Gly Ser Val Ala Ala Ala Pro Glu Lys Lys Val Glu
                20                  25                  30
Gln Val Arg Asn Val Glu Lys Asn Tyr Gly Leu Leu Thr Pro Gly
                35                  40                  45
Leu Phe Arg Lys Ile Gln Lys Leu Asn Pro Asn Glu Glu Ile Ser
                50                  55                  60
Thr Val Ile Val Phe Glu Asn His Arg Glu Lys Glu Ile Ala Val
                65                  70                  75
Arg Val Leu Glu Leu Met Gly Ala Lys Val Arg Tyr Val Tyr His
                80                  85                  90
Ile Ile Pro Ala Ile Ala Ala Asp Leu Lys Val Arg Asp Leu Leu
                95                 100                 105
Val Ile Ser Gly Leu Thr Gly Gly Lys Ala Lys Leu Ser Gly Val
               110                 115                 120
Arg Phe Ile Gln Glu Asp Tyr Lys Val Thr Val Ser Ala Glu Leu
               125                 130                 135
Glu Gly Leu Asp Glu Ser Ala Ala Gln Val Met Ala Thr Tyr Val
               140                 145                 150
Trp Asn Leu Gly Tyr Asp Gly Ser Gly Ile Thr Ile Gly Ile Ile
               155                 160                 165
Asp Thr Gly Ile Asp Ala Ser His Pro Asp Leu Gln Gly Lys Val
               170                 175                 180
Ile Gly Trp Val Asp Phe Val Asn Gly Arg Ser Tyr Pro Tyr Asp
               185                 190                 195
Asp His Gly His Gly Thr His Val Ala Ser Ile Ala Ala Gly Thr
               200                 205                 210
Gly Ala Ala Ser Asn Gly Lys Tyr Lys Gly Met Ala Pro Gly Ala
               215                 220                 225
Lys Leu Ala Gly Ile Lys Val Leu Gly Ala Asp Gly Ser Gly Ser
               230                 235                 240
Ile Ser Thr Ile Ile Lys Gly Val Glu Trp Ala Val Asp Asn Lys
               245                 250                 255
Asp Lys Tyr Gly Ile Lys Val Ile Asn Leu Ser Leu Gly Ser Ser
               260                 265                 270
Gln Ser Ser Asp Gly Thr Asp Ala Leu Ser Gln Ala Val Asn Ala
               275                 280                 285
Ala Trp Asp Ala Gly Leu Val Val Val Ala Ala Gly Asn Ser
               290                 295                 300
Gly Pro Asn Lys Tyr Thr Ile Gly Ser Pro Ala Ala Ala Ser Lys
               305                 310                 315
Val Ile Thr Val Gly Ala Val Asp Lys Tyr Asp Val Ile Thr Ser
               320                 325                 330
Phe Ser Ser Arg Gly Pro Thr Ala Asp Gly Arg Leu Lys Pro Glu
               335                 340                 345
Val Val Ala Pro Gly Asn Trp Ile Ile Ala Ala Arg Ala Ser Gly
               350                 355                 360
```

Thr Ser Met Gly Gln Pro Ile Asn Asp Tyr Tyr Thr Ala Ala Pro
            365                 370                 375

Gly Thr Ser Met Ala Thr Pro His Val Ala Gly Ile Ala Ala Leu
            380                 385                 390

Leu Leu Gln Ala His Pro Ser Trp Thr Pro Asp Lys Val Lys Thr
            395                 400                 405

Ala Leu Ile Glu Thr Ala Asp Ile Val Lys Pro Asp Glu Ile Ala
            410                 415                 420

Asp Ile Ala Tyr Gly Ala Gly Arg Val Asn Ala Tyr Lys Ala Ile
            425                 430                 435

Asn Tyr Asp Asn Tyr Ala Lys Leu Val Phe Thr Gly Tyr Val Ala
            440                 445                 450

Asn Lys Gly Ser Gln Thr His Gln Phe Val Ile Ser Gly Ala Ser
            455                 460                 465

Phe Val Thr Ala Thr Leu Tyr Trp Asp Asn Ala Asn Ser Asp Leu
            470                 475                 480

Asp Leu Tyr Leu Tyr Asp Pro Asn Gly Asn Gln Val Asp Tyr Ser
            485                 490                 495

Tyr Thr Ala Tyr Gly Phe Glu Lys Val Gly Tyr Tyr Asn Pro
            500                 505                 510

Thr Asp Gly Thr Trp Thr Ile Lys Val Ser Tyr Ser Gly Ser
            515                 520                 525

Ala Asn Tyr Gln Val Asp Val Val Ser Asp Gly Ser Leu Ser Gln
            530                 535                 540

Pro Gly Ser Ser Pro Ser Pro Gln Pro Glu Pro Thr Val Asp Ala
            545                 550                 555

Lys Thr Phe Gln Gly Ser Asp His Tyr Tyr Asp Arg Ser Asp
            560                 565                 570

Thr Phe Thr Met Thr Val Asn Ser Gly Ala Thr Lys Ile Thr Gly
            575                 580                 585

Asp Leu Val Phe Asp Thr Ser Tyr His Asp Leu Asp Leu Tyr Leu
            590                 595                 600

Tyr Asp Pro Asn Gln Lys Leu Val Asp Arg Ser Glu Ser Pro Asn
            605                 610                 615

Ser Tyr Glu His Val Glu Tyr Leu Thr Pro Ala Pro Gly Thr Trp
            620                 625                 630

Tyr Phe Leu Val Tyr Ala Tyr Tyr Thr Tyr Gly Trp Ala Tyr Tyr
            635                 640                 645

Glu Leu Thr Ala Lys Val Tyr Tyr Gly
            650

(2) INFORMATION FOR SEQ ID NO: 36:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 36:

TCTGAATTCG TTCTTTTCTG TATGG                         25

(2) INFORMATION FOR SEQ ID NO: 37:

(i) SEQUENCE CHARACTERISTICS:
           (A) LENGTH: 20 base pairs
           (B) TYPE: nucleic acid
           (C) STRANDEDNESS: double
           (D) TOPOLOGY: linear (ii) MOLECULE TYPE: genomic DNA (xi) SEQUENCE DESCRIPTION: SEQ ID NO: 37:

TGTACTGCTG GATCCGGCAG                                                  20

(2) INFORMATION FOR SEQ ID NO: 38:

(i) SEQUENCE CHARACTERISTICS:
           (A) LENGTH: 80 base pairs
           (B) TYPE: nucleic acid
           (C) STRANDEDNESS: double
           (D) TOPOLOGY: linear (ii) MOLECULE TYPE: genomic DNA (xi) SEQUENCE DESCRIPTION: SEQ ID NO: 38:

GGATCCATCA GATTTTTGAG TGTAGATCAA CCAGTATGCT GCATTTGTAA TTGTGAGATA      60

ATATCTCCCG CGGGTAAGGT                                                  80

(2) INFORMATION FOR SEQ ID NO: 39:

(i) SEQUENCE CHARACTERISTICS:
           (A) LENGTH: 30 base pairs
           (B) TYPE: nucleic acid
           (C) STRANDEDNESS: double
           (D) TOPOLOGY: linear (ii) MOLECULE TYPE: genomic DNA (xi) SEQUENCE DESCRIPTION: SEQ ID NO: 39:

AGAGGCATGC GTATCCATCA GATTTTTGAG                                       30

(2) INFORMATION FOR SEQ ID NO: 40:

(i) SEQUENCE CHARACTERISTICS:
           (A) LENGTH: 20 base pairs
           (B) TYPE: nucleic acid
           (C) STRANDEDNESS: double
           (D) TOPOLOGY: linear (ii) MOLECULE TYPE: genomic DNA (xi) SEQUENCE DESCRIPTION: SEQ ID NO: 40:

AGTGAACGGA TACTTGGAAC                                                  20

(2) INFORMATION FOR SEQ ID NO: 41:

(i) SEQUENCE CHARACTERISTICS:
           (A) LENGTH: 20 base pairs
           (B) TYPE: nucleic acid
           (C) STRANDEDNESS: double
           (D) TOPOLOGY: linear (ii) MOLECULE TYPE: genomic DNA (xi) SEQUENCE DESCRIPTION: SEQ ID NO: 41:

GTTCCAAGTA TCCGTTCACT                                                  20

(2) INFORMATION FOR SEQ ID NO: 42:

(i) SEQUENCE CHARACTERISTICS:
           (A) LENGTH: 12 amino acids

```
         (B) TYPE: amino acids
         (C) STRANDEDNESS: double
         (D) TOPOLOGY: linear (ii) MOLECULE TYPE: genomic DNA (xi) SEQUENCE DESCRIPTION: SEQ ID NO: 42:

Ala Glu Leu Glu Gly Leu Asp Glu Ser Ala Ala Gln
                 5                   10
```